(12) United States Patent
Solomon et al.

(10) Patent No.: US 9,068,628 B2
(45) Date of Patent: Jun. 30, 2015

(54) ROBOTIC ARMS WITH STRAP DRIVE TRAINS

(71) Applicant: INTUITIVE SURGICAL OPERATIONS, INC., Sunnyvale, CA (US)

(72) Inventors: Todd R. Solomon, San Jose, CA (US); Thomas G. Cooper, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 13/890,233

(22) Filed: May 8, 2013

(65) Prior Publication Data
US 2013/0239735 A1    Sep. 19, 2013

Related U.S. Application Data

(60) Division of application No. 11/611,849, filed on Dec. 15, 2006, and a continuation-in-part of application No. 10/957,077, filed on Sep. 30, 2004, now Pat. No. 7,594,912.

(60) Provisional application No. 60/752,514, filed on Dec. 20, 2005, provisional application No. 60/752,788, filed on Dec. 21, 2005.

(51) Int. Cl.
*B25J 18/00* (2006.01)
*F16H 7/20* (2006.01)
(Continued)

(52) U.S. Cl.
CPC ............. *F16H 7/20* (2013.01); *Y10T 29/49826* (2013.01); *Y10T 29/49455* (2013.01);
(Continued)

(58) Field of Classification Search
USPC ............... 74/490.01, 490.04, 490.05, 490.06, 74/89.2, 89.22; 901/15, 19, 21, 27, 28, 29; 606/1, 130; 24/68 A, 68 D, 68 R, 32; 254/208, 226, 242, 280, 284, 312, 325, 254/334, 359, 385, 390
See application file for complete search history.

(56) References Cited

U.S. PATENT DOCUMENTS 369,023 A * 8/1887 Newell ............................... 24/32
586,731 A * 7/1897 Monroe ........................ 74/89.22
(Continued)

FOREIGN PATENT DOCUMENTS

| CH | 482439 | 12/1969 |
| DE | 2819976 | 11/1979 |

(Continued)

OTHER PUBLICATIONS

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

(Continued)

*Primary Examiner* — Justin Krause
*Assistant Examiner* — Gregory Prather

(57) ABSTRACT

In one embodiment of the invention, a robotic arm is provided including a linkage assembly and a strap drive train. The linkage assembly includes first, second, third, and fourth links pivotally coupled in series together at first, second, and third joints to define a parallelogram with an insertion axis. The strap drive train includes first and second sets of straps coupled to the linkage assembly. As the linkage assembly is moved about a pitch axis, the first set of straps ensures the third link maintains the same angle relative to the first link, and the first and second set of straps ensures the fourth link maintains the same angle relative to the second link.

5 Claims, 33 Drawing Sheets

(51) Int. Cl.
*A61B 19/00* (2006.01)
*B25J 9/10* (2006.01)

(52) U.S. Cl.
CPC ..... Y10T 74/20323 (2013.01); Y10T 74/20305 (2013.01); *A61B 19/2203* (2013.01); A61B 19/5212 (2013.01); A61B 2019/2223 (2013.01); A61B 2019/2234 (2013.01); A61B 2019/2242 (2013.01); A61B 2019/2246 (2013.01); *B25J 9/1045* (2013.01); B25J 18/00 (2013.01); Y10S 901/21 (2013.01)

(56) References Cited

U.S. PATENT DOCUMENTS

| | | | |
|---|---|---|---|
| 669,393 A * | 3/1901 | Jent | 74/89.22 |
| 1,515,335 A * | 11/1924 | Bosco | 24/25 |
| 1,597,152 A * | 8/1926 | Heintz | 74/89.22 |
| 1,700,468 A * | 1/1929 | Clutter et al. | 74/25 |
| 2,027,275 A * | 1/1936 | Foster | 74/89.22 |
| D134,917 S | 1/1943 | Eubanks | |
| 2,331,382 A | 10/1943 | Eubanks | |
| 2,815,697 A | 12/1957 | Saunders-Singer | |
| 3,011,034 A * | 11/1961 | Laviana et al. | 200/38 R |
| 3,025,647 A * | 3/1962 | Moody | 451/411 |
| 3,193,633 A * | 7/1965 | Netzel et al. | 200/50.24 |
| 3,463,329 A | 8/1969 | Gartner | |
| 3,500,692 A * | 3/1970 | Parker et al. | 74/89.22 |
| 3,695,215 A * | 10/1972 | Lambiris | 116/28.1 |
| 3,736,056 A | 5/1973 | Burnet et al. | |
| 3,739,649 A * | 6/1973 | Pacini et al. | 74/89.22 |
| 3,872,960 A * | 3/1975 | Gabor | 400/335 |
| 3,954,282 A | 5/1976 | Hege | |
| 4,143,445 A * | 3/1979 | Fougman | 24/68 R |
| 4,260,319 A | 4/1981 | Motoda et al. | |
| 4,312,432 A * | 1/1982 | Sugawa | 192/225 |
| 4,362,525 A * | 12/1982 | Sproul | 474/117 |
| 4,396,919 A * | 8/1983 | Speicher | 343/765 |
| 4,486,183 A * | 12/1984 | Posiviata et al. | 474/94 |
| 4,537,084 A * | 8/1985 | Passemard et al. | 74/89.22 |
| 4,543,033 A | 9/1985 | Czermak et al. | |
| 4,696,501 A | 9/1987 | Webb | |
| 4,697,467 A * | 10/1987 | Ando | 74/89.2 |
| 4,728,252 A | 3/1988 | Lada et al. | |
| 4,897,015 A | 1/1990 | Abbe et al. | |
| 4,921,393 A | 5/1990 | Andeen et al. | |
| 5,060,532 A | 10/1991 | Barker | |
| 5,074,539 A * | 12/1991 | Wells et al. | 271/12 |
| 5,078,140 A | 1/1992 | Kwoh | |
| 5,103,263 A | 4/1992 | Moore et al. | |
| 5,129,911 A | 7/1992 | Siczek et al. | |
| 5,149,057 A * | 9/1992 | Meurer | 254/276 |
| 5,157,980 A * | 10/1992 | Chezzi | 74/89.22 |
| 5,184,601 A | 2/1993 | Putman | |
| 5,209,747 A | 5/1993 | Knoepfler | |
| 5,217,003 A | 6/1993 | Wilk | |
| 5,217,453 A | 6/1993 | Wilk | |
| 5,219,351 A | 6/1993 | Teubner et al. | |
| 5,222,409 A | 6/1993 | Dalakian | |
| 5,257,998 A | 11/1993 | Ota et al. | |
| 5,273,039 A | 12/1993 | Fujiwara et al. | |
| 5,279,309 A | 1/1994 | Taylor et al. | |
| 5,333,986 A * | 8/1994 | Mizukami et al. | 414/217 |
| 5,339,799 A | 8/1994 | Kami et al. | |
| 5,339,929 A * | 8/1994 | Chern | 188/24.16 |
| 5,343,385 A | 8/1994 | Joskowicz et al. | |
| 5,353,202 A | 10/1994 | Ansell et al. | |
| 5,368,015 A | 11/1994 | Wilk | |
| 5,397,323 A | 3/1995 | Taylor et al. | |
| 5,402,801 A | 4/1995 | Taylor | |
| 5,417,210 A | 5/1995 | Funda et al. | |
| 5,445,166 A | 8/1995 | Taylor | |
| 5,458,479 A * | 10/1995 | Minghetti | 425/503 |
| 5,479,929 A | 1/1996 | Cooper et al. | |
| 5,572,999 A | 11/1996 | Funda et al. | |
| 5,599,268 A * | 2/1997 | Andersson et al. | 493/184 |
| 5,630,431 A | 5/1997 | Taylor | |
| 5,682,795 A | 11/1997 | Solomon et al. | |
| 5,695,500 A | 12/1997 | Taylor et al. | |
| 5,697,939 A | 12/1997 | Kubota et al. | |
| 5,749,362 A | 5/1998 | Funda et al. | |
| 5,762,458 A | 6/1998 | Wang et al. | |
| 5,778,730 A | 7/1998 | Solomon et al. | |
| 5,792,135 A | 8/1998 | Madhani et al. | |
| 5,794,487 A | 8/1998 | Solomon et al. | |
| 5,800,423 A | 9/1998 | Jensen | |
| 5,808,665 A | 9/1998 | Green | |
| 5,813,282 A * | 9/1998 | Azuma | 74/89.22 |
| 5,815,640 A | 9/1998 | Wang et al. | |
| 5,817,084 A | 10/1998 | Jensen | |
| 5,841,950 A | 11/1998 | Wang et al. | |
| 5,855,583 A | 1/1999 | Wang et al. | |
| 5,876,325 A | 3/1999 | Mizuno et al. | |
| 5,878,193 A | 3/1999 | Wang et al. | |
| 5,879,001 A * | 3/1999 | Perego | 271/10.07 |
| 5,907,664 A | 5/1999 | Wang et al. | |
| 5,931,832 A | 8/1999 | Jensen | |
| 5,967,112 A * | 10/1999 | Haga et al. | 123/196 W |
| 6,001,108 A | 12/1999 | Wang et al. | |
| 6,007,550 A | 12/1999 | Wang et al. | |
| 6,106,511 A | 8/2000 | Jensen | |
| 6,116,197 A * | 9/2000 | Tsunoda et al. | 123/41.82 R |
| 6,132,368 A | 10/2000 | Cooper | |
| 6,167,686 B1 * | 1/2001 | Becker et al. | 56/17.3 |
| 6,220,106 B1 * | 4/2001 | Hayashi | 74/89.22 |
| 6,246,200 B1 | 6/2001 | Blumenkranz et al. | |
| 6,346,072 B1 | 2/2002 | Cooper | |
| 6,367,608 B1 * | 4/2002 | Franceschi | 198/335 |
| 6,371,952 B1 | 4/2002 | Madhani et al. | |
| 6,394,998 B1 | 5/2002 | Wallace et al. | |
| 6,406,472 B1 | 6/2002 | Jensen | |
| 6,428,266 B1 | 8/2002 | Solomon et al. | |
| 6,441,577 B2 | 8/2002 | Blumenkranz et al. | |
| 6,451,027 B1 | 9/2002 | Cooper et al. | |
| 6,594,552 B1 | 7/2003 | Moll et al. | |
| 6,659,939 B2 | 12/2003 | Moll et al. | |
| 6,676,669 B2 | 1/2004 | Charles et al. | |
| 6,699,235 B2 | 3/2004 | Wallace et al. | |
| 6,702,805 B1 | 3/2004 | Stuart | |
| 6,737,826 B2 * | 5/2004 | Gilchrist | 318/568.21 |
| 6,758,843 B2 | 7/2004 | Jensen | |
| 6,788,018 B1 | 9/2004 | Blumenkranz | |
| 6,871,643 B2 * | 3/2005 | Cooper et al. | 124/25.6 |
| 6,969,385 B2 * | 11/2005 | Moreyra | 606/1 |
| 7,021,173 B2 | 4/2006 | Stoianovici et al. | |
| 7,101,363 B2 | 9/2006 | Nishizawa et al. | |
| 7,108,688 B2 | 9/2006 | Jensen | |
| 7,124,657 B2 * | 10/2006 | Nagai et al. | 74/89.2 |
| 7,316,681 B2 | 1/2008 | Madhani et al. | |
| 7,395,606 B2 | 7/2008 | Crampton | |
| 7,594,912 B2 | 9/2009 | Cooper et al. | |
| 7,644,906 B2 * | 1/2010 | Rodrigue | 254/242 |
| 7,865,266 B2 | 1/2011 | Moll et al. | |
| 8,062,288 B2 | 11/2011 | Cooper et al. | |
| 8,256,319 B2 | 9/2012 | Cooper et al. | |
| 8,562,594 B2 | 10/2013 | Cooper et al. | |
| 2002/0091374 A1 | 7/2002 | Cooper | |
| 2002/0169440 A1 * | 11/2002 | Jensen | 606/1 |
| 2005/0043718 A1 | 2/2005 | Madhani et al. | |
| 2005/0241236 A1 * | 11/2005 | Smith | 49/352 |
| 2007/0089557 A1 | 4/2007 | Solomon et al. | |
| 2007/0142969 A1 | 6/2007 | Devengenzo et al. | |
| 2008/0021440 A1 | 1/2008 | Solomon | |
| 2008/0087871 A1 * | 4/2008 | Schena | 254/226 |
| 2009/0229388 A1 * | 9/2009 | Lee et al. | 74/89.22 |
| 2011/0137322 A1 | 6/2011 | Moll et al. | |
| 2013/0239392 A1 | 9/2013 | Solomon et al. | |
| 2013/0244820 A1 | 9/2013 | Solomon et al. | |
| 2014/0094824 A1 | 4/2014 | Cooper et al. | |

FOREIGN PATENT DOCUMENTS

| | | |
|---|---|---|
| EP | 239409 | 9/1987 |
| EP | 0291292 | 11/1988 |

(56) References Cited

FOREIGN PATENT DOCUMENTS

| EP | 0595291 A1 | 5/1994 |
|---|---|---|
| FR | 2460762 | 1/1981 |
| FR | 2593106 A1 | 7/1987 |
| FR | 2845889 A1 | 4/2004 |
| GB | 2117732 A | 10/1983 |
| JP | 7059788 A2 | 3/1995 |
| JP | 7136173 A2 | 5/1995 |
| WO | WO-9501757 | 1/1995 |

OTHER PUBLICATIONS

Belt Technologies, "Belt Technologies, Inc. Design Guide and Engineer's Reference for Metal Belts," 1999, 24 pages.

Ben Gayed, M. et al., "An Advanced Control Micromanipulator for Surgical Applications," Systems Science, 1987, pp. 123-134, vol. 13.

Extended European Search Report for Application No. EP10175702, mailed on Jun. 13, 2013, 8 pages.

Extended European Search Report for Application No. EP10175715, mailed on May 24, 2012, 7 pages.

Guerrouad, Aicha et al., "SMOS: Stereotaxical Microtelemanipulator for Ocular Surgery," IEEE Engineering in Medicine & Biology Society 11th annual international conference, Nov. 9-12, 1989, pp. 879-880, vol. 3, IEEE.

Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.

PCT/US05/32488 International Search Report, mailed May 9, 2006, 4 pages.

PCT/US05/32488 Written Opinion of the International Search Authority, received May 10, 2006, 7 pages.

PCT/US06/62377 International Search Report and Written Opinion of the International Searching Authority, mailed Jul. 16, 2008, 6 pages.

Rininsland, Hermann; "ARTEMIS: A telemanipulator for cardiac surgery," European Journal of Cardio-Thoracic Surgery, vol. 16, Supplement 2, pp. S106-S111, Nov. 1999.

Rosheim, Mark E., "Robot Evolution: Development of Anthrobotics," Pub. John Wiley & Sons, Inc., New York, 1994, Chapter 2, pp. 37-156

Vertut, Jean and Phillipe Coiffet, Robot Technology: Teleoperation and Robotics Evolution and Development, English translation, Prentice Hall, Inc., Inglewood Cliffs, NJ, USA 1986, volume 3A, 332 pages.

\* cited by examiner

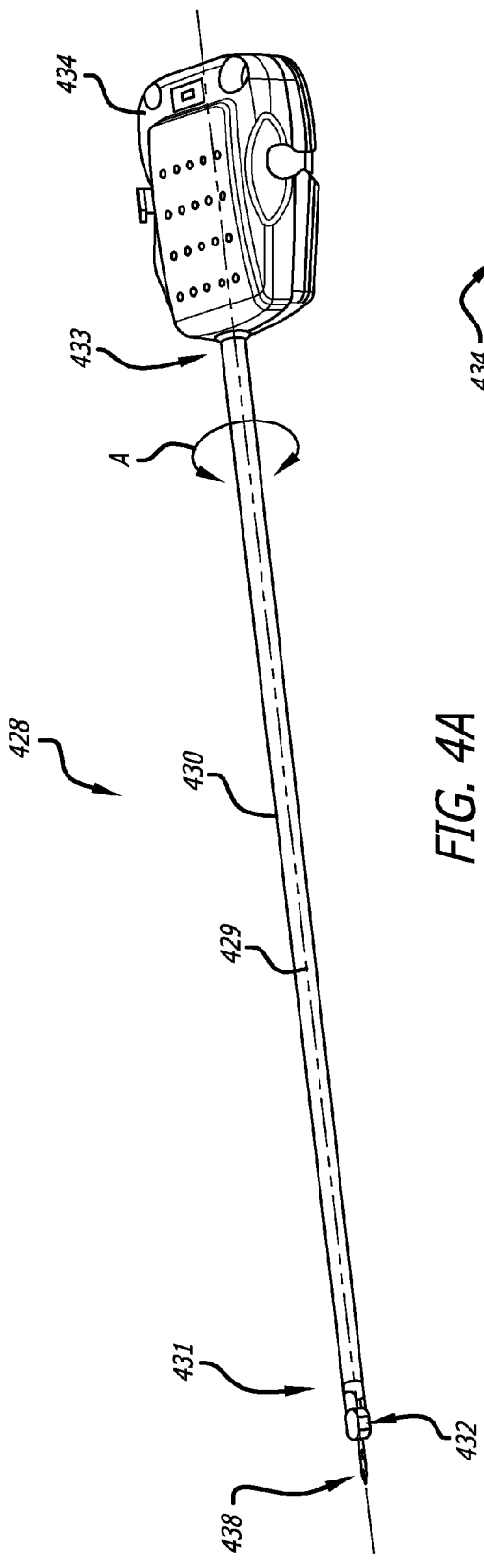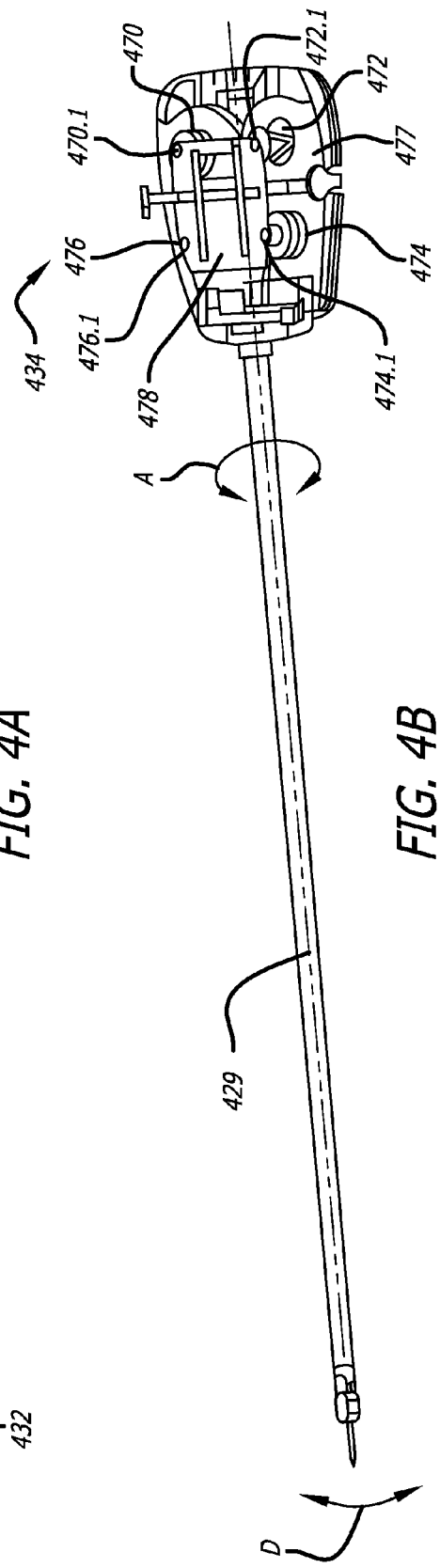
FIG. 4A
FIG. 4B

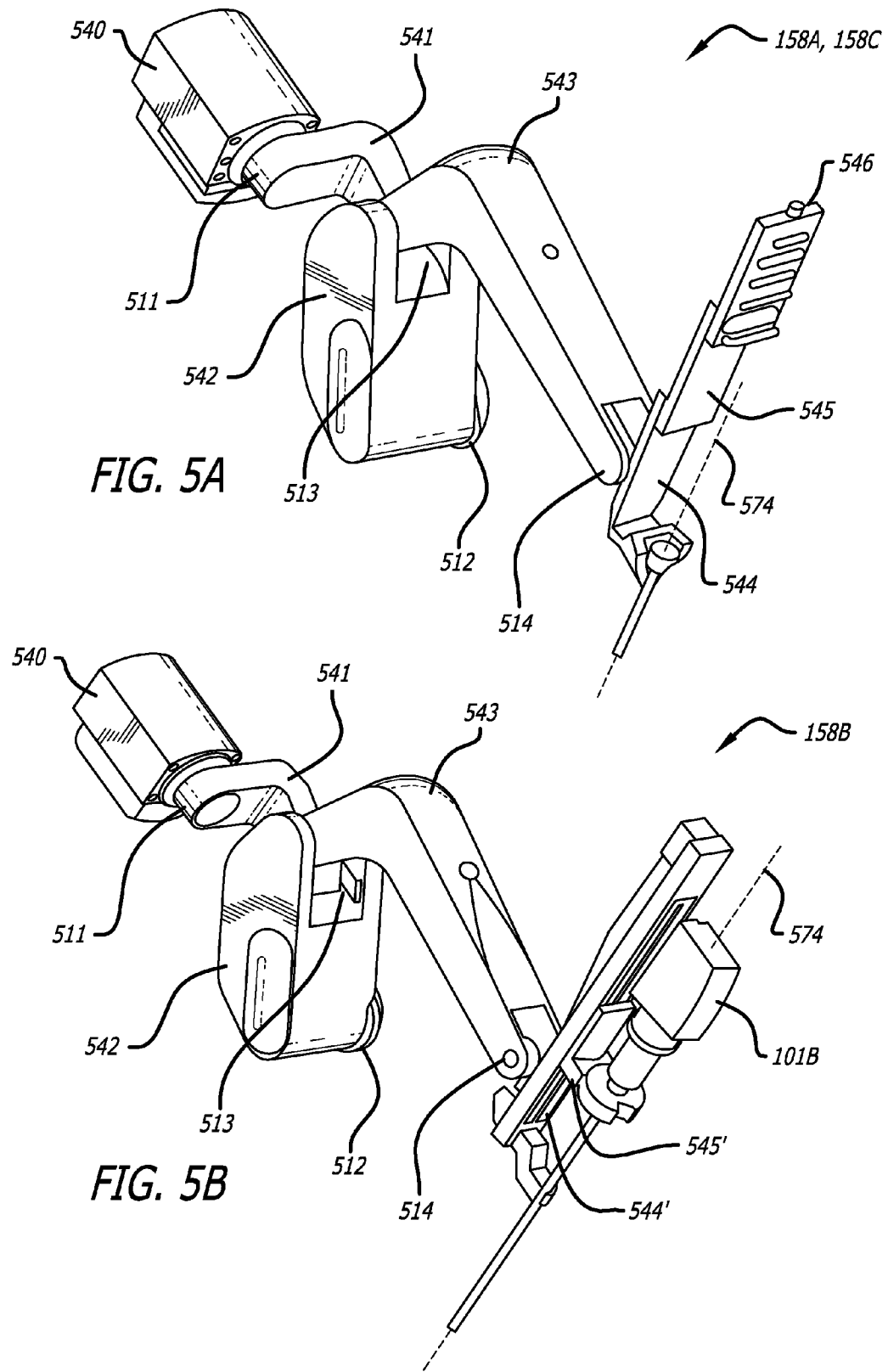

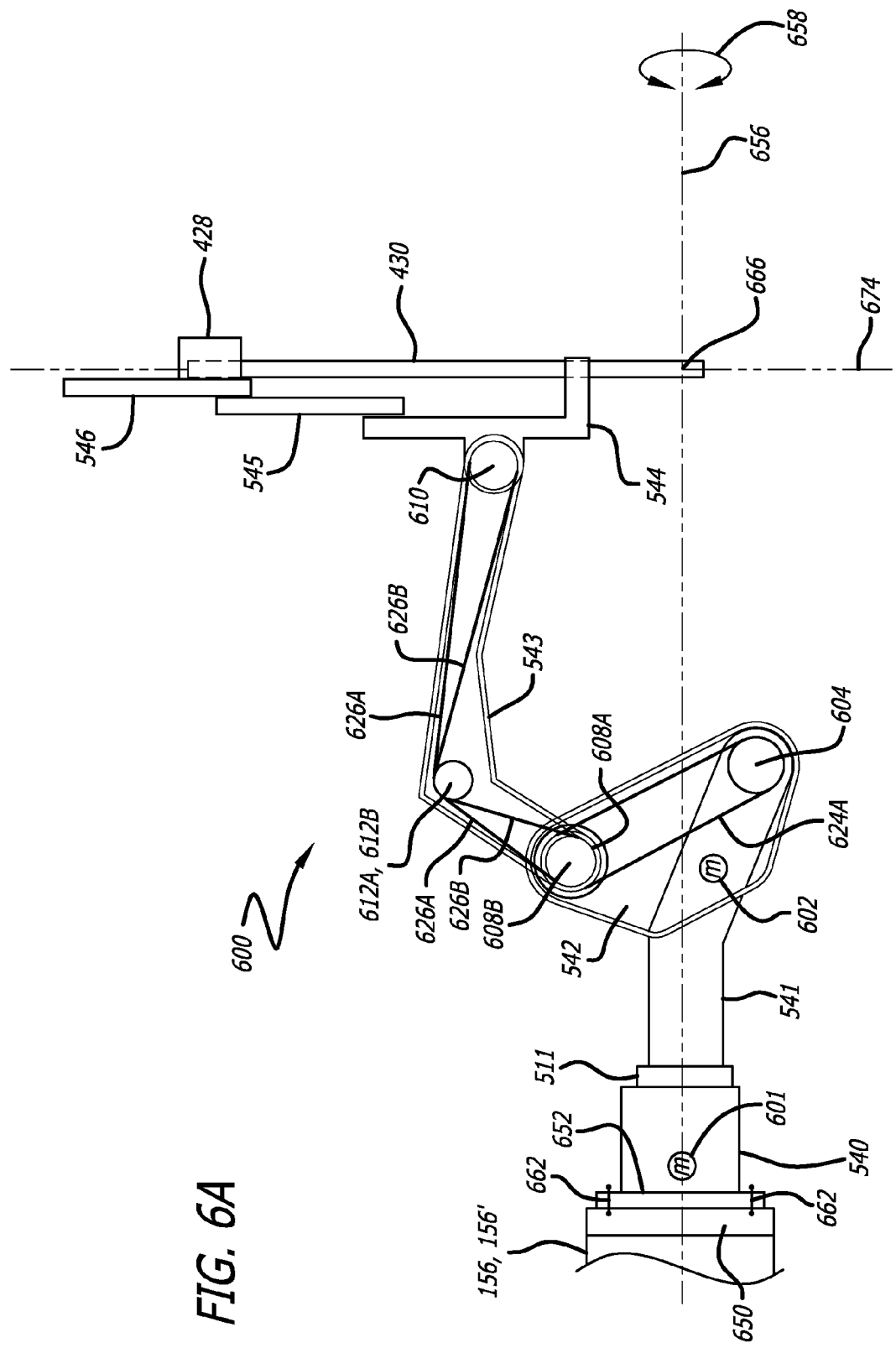

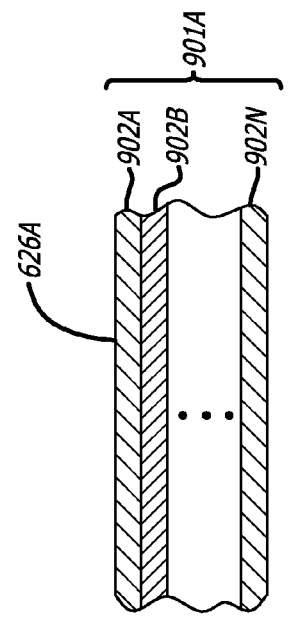
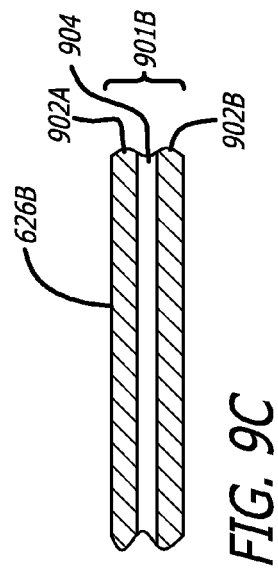
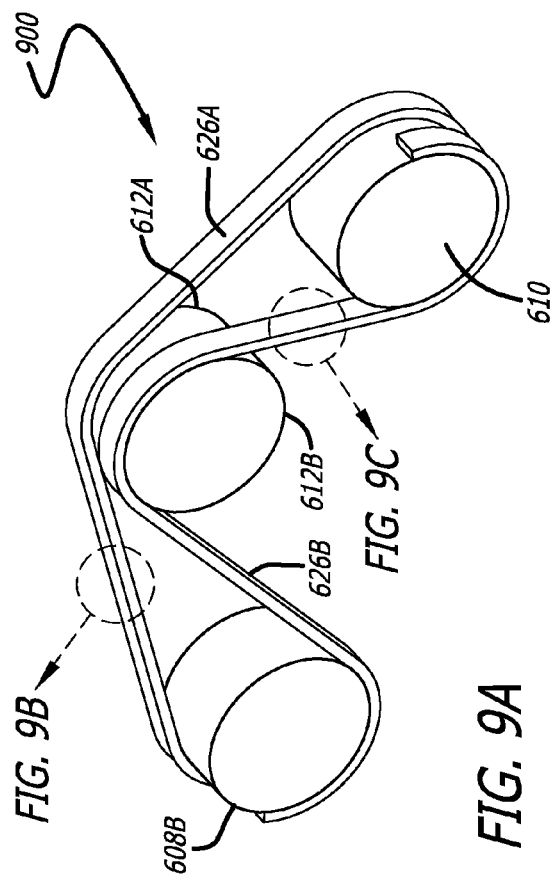
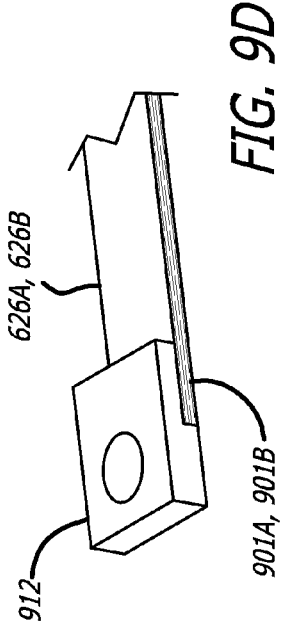
FIG. 9B
FIG. 9C
FIG. 9A
FIG. 9D

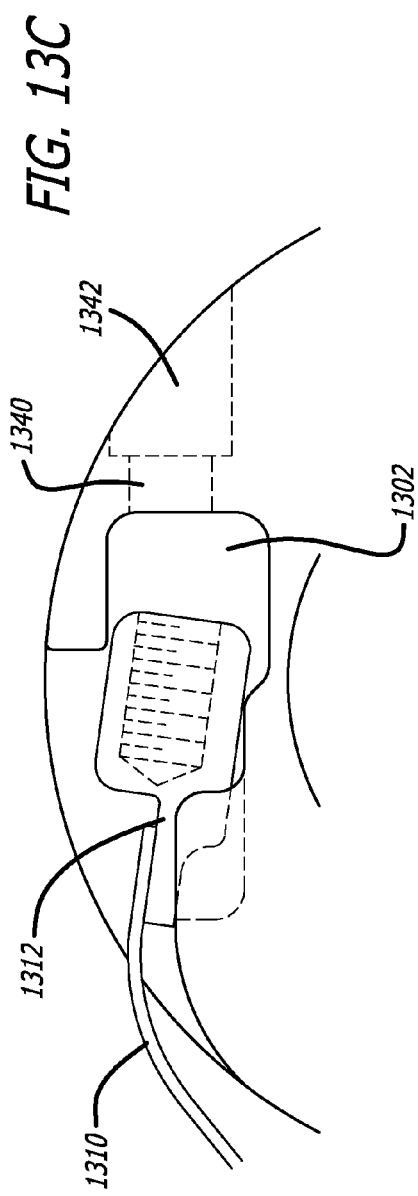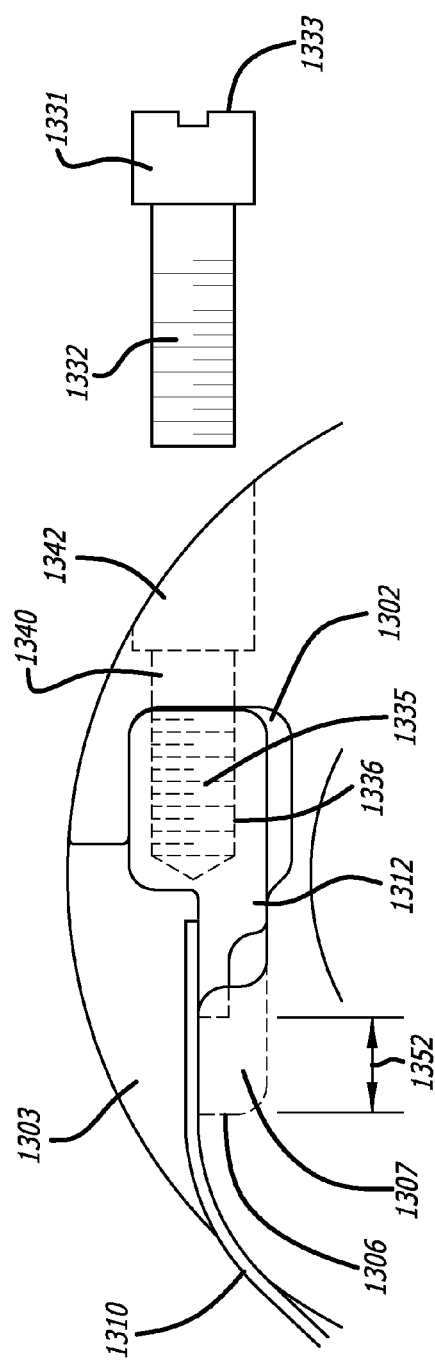

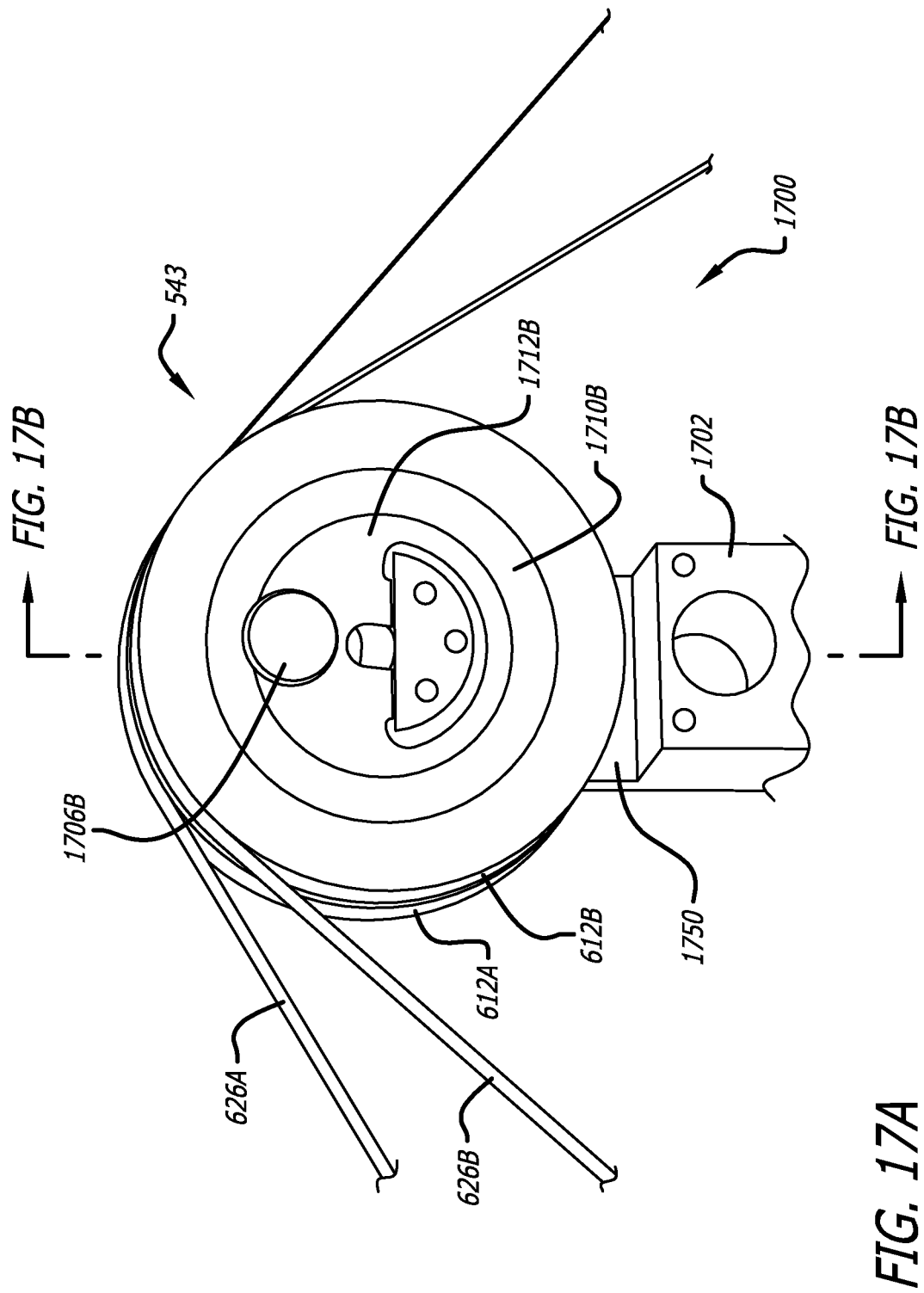

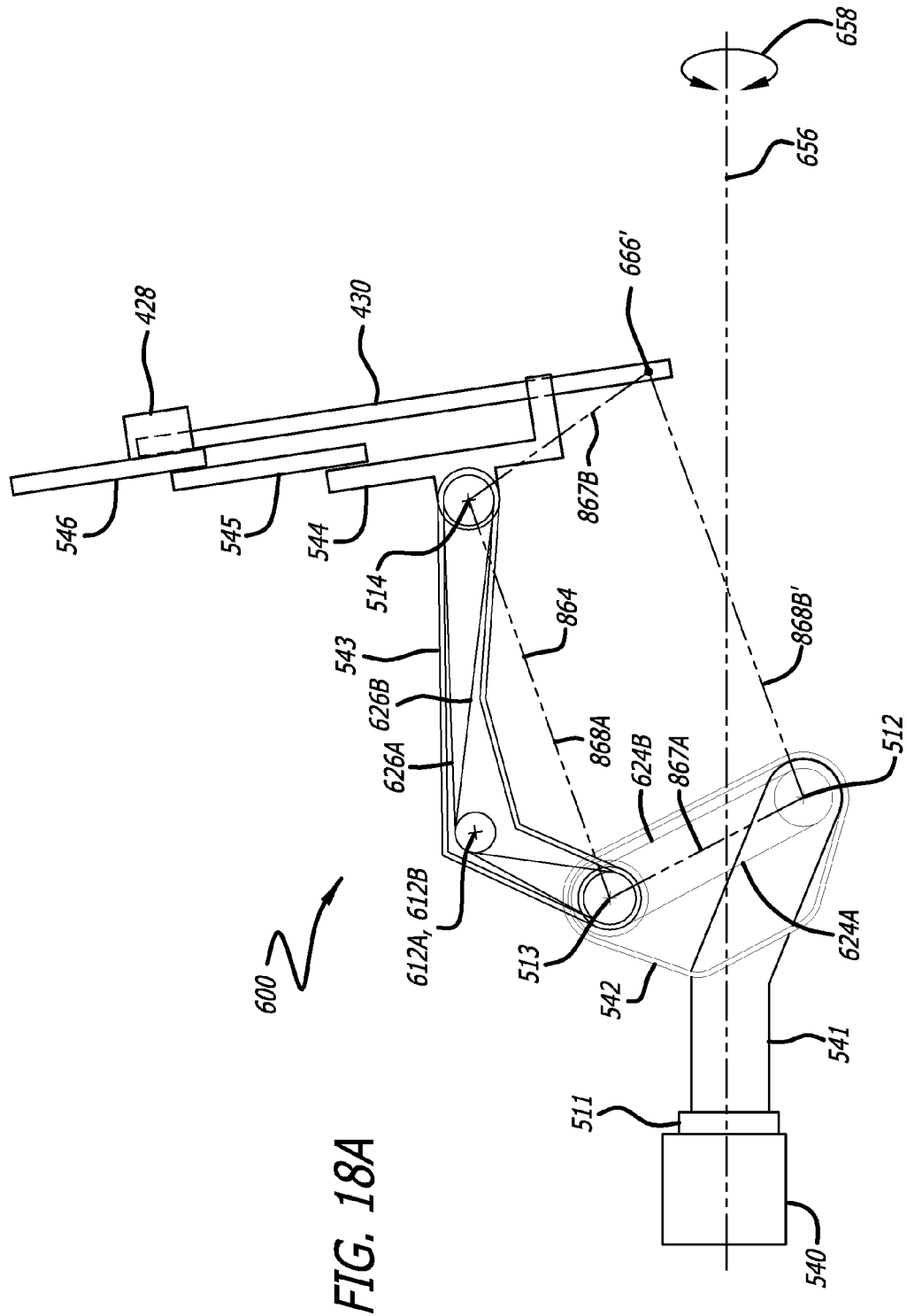

ROBOTIC ARMS WITH STRAP DRIVE TRAINS

CROSS REFERENCE TO RELATED APPLICATION

This non-provisional patent application is a divisional application claiming the benefit of U.S. patent application Ser. No. 11/611,849 entitled MULTI-PLY STRAP DRIVE TRAINS FOR ROBOTIC ARMS, filed by Todd R. Solomon et al on Dec. 6, 2006 pending. U.S. patent application Ser. No. 11/611,849 claims the benefit of provisional patent application No. 60/752,514, entitled MULTI-PLY STRAP DRIVE TRAIN FOR ROBOTIC SURGICAL ARM filed by Todd R. Solomon et al on Dec. 20, 2005, incorporated herein by reference, and provisional U.S. patent application Ser. No. 60/752,788 entitled FLAT ELECTRICAL CONDUCTORS OVER PULLEYS IN A STRAP DRIVE-TRAIN OF A ROBOTIC SURGICAL ARM, filed on Dec. 21, 2005, by Todd R. Solomon. U.S. patent application Ser. No. 11/611, 849 is further a continuation in part (CIP) and claims the benefit of U.S. patent application Ser. No. 10/957,077, entitled OFFSET REMOTE CENTER MANIPULATOR FOR ROBOTIC SURGERY, filed on Sep. 30, 2004 by Thomas G. Cooper and Todd R. Solomon.

FIELD

The embodiments of the invention relate generally to robotic surgical systems. More particularly, the embodiments of the invention relate to robotic surgical arms.

BACKGROUND

Typical robotic surgical arms include a number of joints and links to provide a range of motion to form a work envelope for an end effector coupled thereto. It is desirable to improve the range of motion of robotic surgical arms to increase the work envelope of the end effectors coupled thereto to perform a wider variety of robotic surgical procedures.

Typical robotic surgical arms further include a plurality of metal control cables routed therein which are moved to mechanically control the motion of the links about the joints and the motion in the end effector. The use of the plurality of metal control cables is expensive and complicates the maintenance of the robotic surgical arms. It is desirable to reduce the manufacturing and maintenance costs of robotic surgical arms while at the same time improving its range of motion.

BRIEF SUMMARY

The embodiments of the invention are summarized by the claims that follow below.

BRIEF DESCRIPTIONS OF THE DRAWINGS

FIG. 1 is a block diagram of a robotic surgery system to perform minimally invasive robotic surgical procedures using one or more robotic surgical arms with a strap drive train.

FIG. 2 a perspective view of the robotic patient-side system of FIG. 1 with the one or more robotic surgical arms having the strap drive train.

FIGS. 4A-4B is a perspective view of an robotic surgical tool to couple to the one or more robotic surgical arms having the strap drive train.

FIGS. 5A-5B are perspective views of a patient side manipulator or robotic surgical arm and an endoscopic camera manipulator or robotic surgical arm.

FIGS. 6A-6B are schematic side views of a first multi-strap drive train having a two-strap system in a third link.

FIGS. 9A-9D are views of an exemplary two-strap system with multi-layer and multi-ply straps that may be used in the third link.

FIGS. 13A-13D illustrate magnified views of the first tensioning system that may be used to couple and tension the straps to the pulleys in the links of the robotic surgical arm.

FIGS. 17A-17E illustrate views of a camber adjustment system and its elements that may be used in the alternate to track straps onto idler pulleys FIGS. 18A-18C illustrate schematic views of adjusting an offset robotic surgical arm to remote center.

DETAILED DESCRIPTION

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention include methods, apparatus and systems for a robotic surgical system. In one embodiment of the invention a robotic surgical system is provided including one or more robotic surgical arms under the control of at least one multi-layer or multi-ply control strap.

Robotic Surgical System

Figure 1:
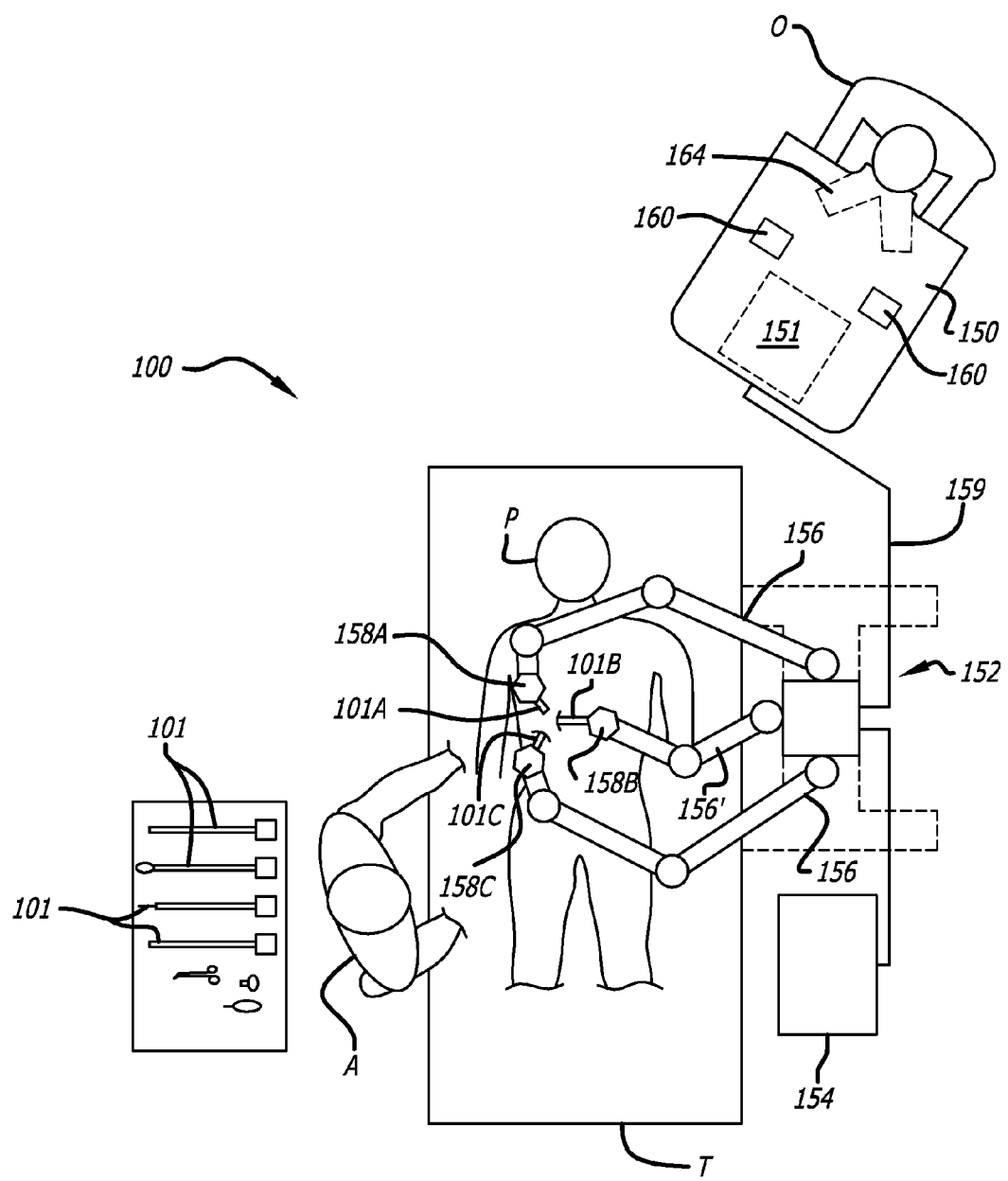

Referring now to FIG. 1, a block diagram of a robotic surgery system 100 is illustrated to perform minimally invasive robotic surgical procedures using one or more robotic arms with strap drive. Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). At least one of the robotic manipulator arms (e.g., the center robotic manipulator arm 158B) is used to support a stereo or three dimensional surgical image capture device 110 such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

A user or operator O (generally a surgeon) performs a minimally invasive surgical procedure on patient P by manipulating control input devices 160 at a master control console 150. A computer 151 of the console 150 directs movement of robotically controlled endoscopic surgical instruments 101A-101C by means of one or more control cables 159, effecting movement of the instruments using a robotic patient-side system 152 (also referred to as a patient-side cart). The robotic patient-side system 152 has one or more robotic arms 158 with the strap drive. Typically, the robotic patient-side system 152 includes at least three robotic manipulator arms 158A-158C supported by linkages 156, 156', with a central robotic arm 158B supporting an endoscopic camera 101B and the robotic arms 158A,158C to left and right of center supporting tissue manipulation tools 101A,101C.

Generally, the robotic patient-side system 152 includes a positioning portion and a driven portion. The positioning portion of the robotic patient-side system 152 remains in a fixed configuration during surgery while manipulating tissue. The driven portion of the robotic patient-side system 152 is actively articulated under the direction of the operator O generating control signals at the surgeon's console 150 during surgery. The actively driven portion of the robotic patient-side system 152 is generally referred to herein as the robotic arms or alternatively to robotic surgical manipulators. The positioning portion of the robotic patient-side system 152 that is in a fixed configuration during surgery may be referred to as "set up arms" 156, 156' with positioning linkage and/or "set-up joints". In an alternate embodiment of the invention, the robotic patient-side system 152 may be replaced by set up arms that couple at one end to left and right sides of the operating table T. The three robotic manipulator arms 158A-158C may then be coupled to the opposite end of the set-up arms to ground to the table T.

For convenience in terminology, manipulators such as robotic surgical arms 158A, 158C actuating the tissue affecting surgical tools 101A,101C are generally referred to herein as a PSM (patient-side manipulator), and a robotic surgical arm 158B controlling an image capture or data acquisition device, such as the endoscopic camera 101B, is generally referred to herein as a ECM (endoscopic-camera manipulator), it being noted that such telesurgical robotic manipulators may optionally actuate, maneuver and control a wide variety of instruments, tools and devices useful in surgery.

An assistant A may assist in pre-positioning of the robotic patient-side system 152 relative to patient P as well as swapping tools or instruments 101 for alternative tool structures, and the like, while viewing the internal surgical site via an assistant's display 154.

Figure 2:
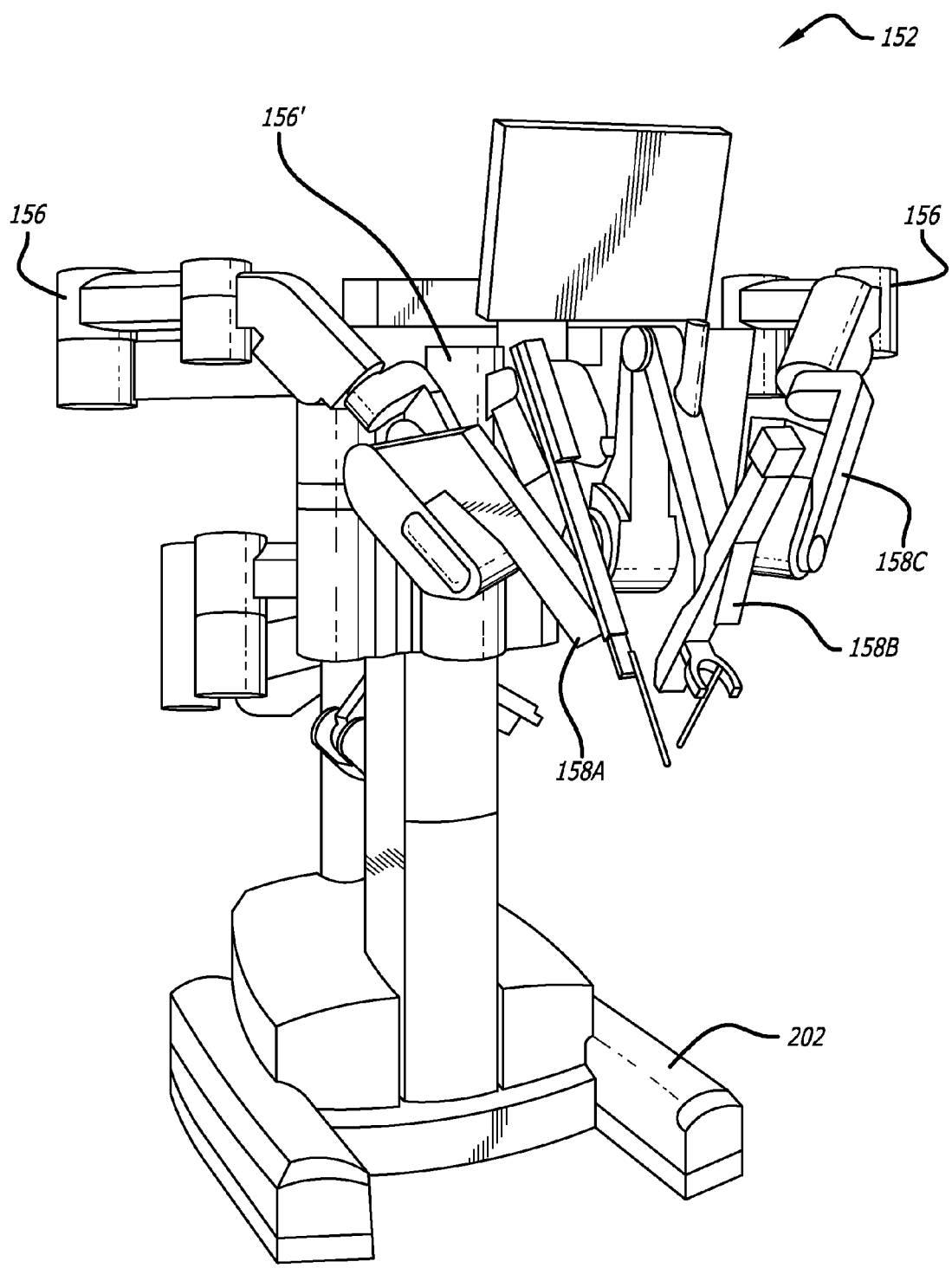

Referring now to FIG. 2, a perspective view of the robotic patient-side system 152 is illustrated. The robotic patient-side system 152 has one or more robotic surgical arms (a.k.a., robotic surgical manipulators) 158A-185C with the strap drive system. The robotic surgical arms 158A,158C are for coupling to robotic surgical tools 101A,101C. The robotic surgical arm 158B is for coupling to an endoscopic camera 101B. The robotic patient-side system 152 further includes a base 202 from which the robotic surgical instruments 101 may be supported. More specifically, the robotic surgical instruments 101 are each supported by the positioning linkage 156 and the robotic surgical arms 158. The linkage structures may optionally be covered by protective covers or not to minimize the inertia that is manipulated by the servomechanism and the overall weight of robotic patient-side system 152.

The robotic patient-side system 152 generally has dimensions suitable for transporting between operating rooms. It typically can fit through standard operating room doors and onto standard hospital elevators. The robotic patient-side system 152 may have a weight and a wheel (or other transportation) system that allows the cart to be positioned adjacent an operating table by a single attendant. The robotic patient-side system 152 may be sufficiently stable during transport to avoid tipping, and to easily withstand overturning moments that may be imposed at the ends of the robotic arms during use.

Figure 3:
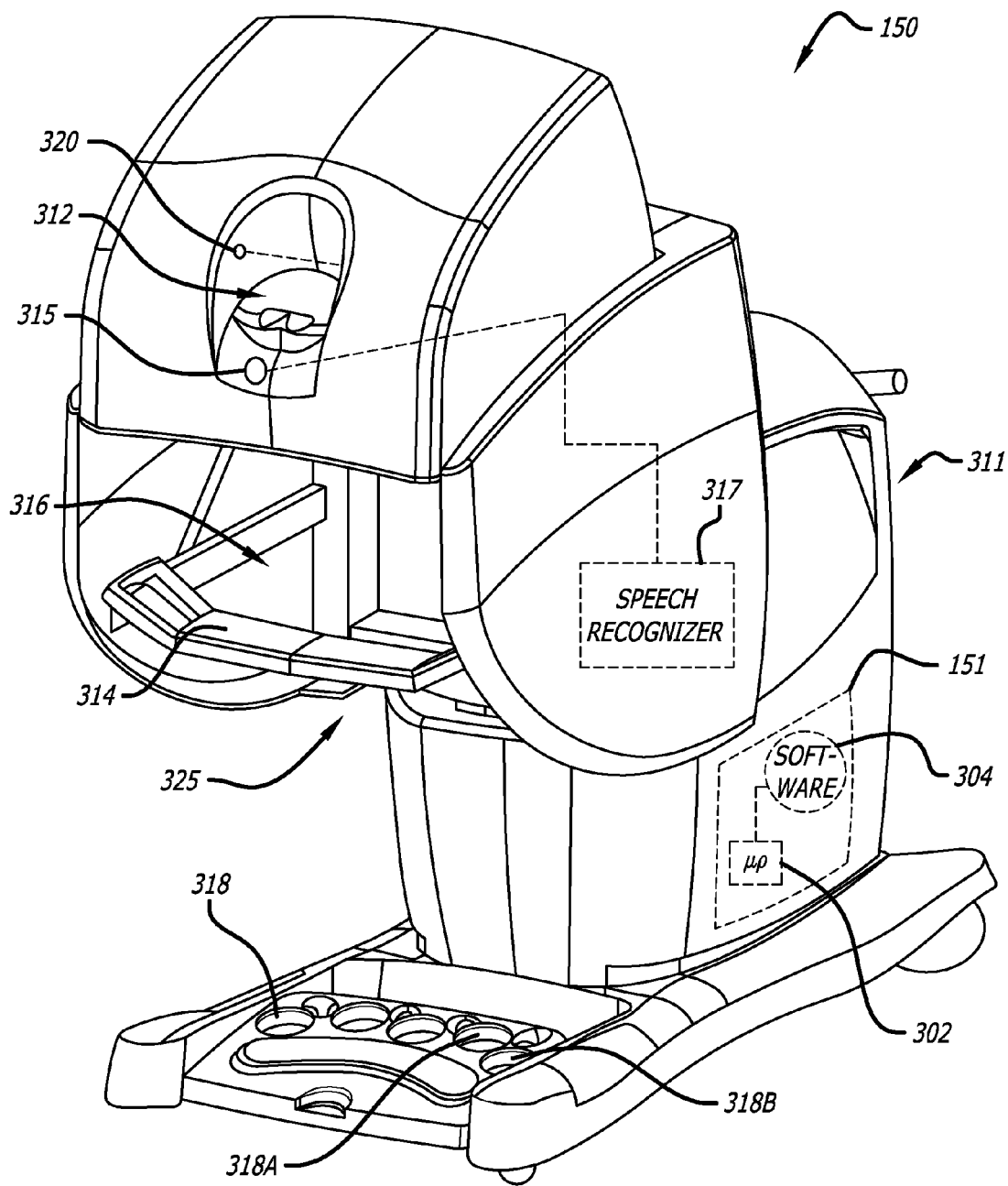
FIG. 3 is a perspective view of the robotic surgical master control console of FIG. 1 that is used to control the one or more robotic surgical arms with the strap drive train.

Referring now to FIG. 3, a perspective view of the robotic surgical master control console 150 is illustrated. The master control console 150 of the robotic surgical system 100 may include the computer 151, a binocular or stereo viewer 312, an arm support 314, a pair of control inputs (control input wrists and control input arms) 160 in a workspace 316, foot pedals 318 (including foot pedals 318A-318B), and a viewing sensor 320.

The stereo viewer 312 has two displays where stereo three-dimensional images of the surgical site may be viewed to perform minimally invasive surgery. When using the master control console, the operator O typically sits in a chair, moves his or her head into alignment with the stereo viewer 312 to view the three-dimensional images of the surgical site. To ensure that the operator is viewing the surgical site when controlling the robotic surgical tools 101, the master control console 150 may include the viewing sensor 320 disposed adjacent the binocular display 312. When the system operator aligns his or her eyes with the binocular eye pieces of the display 312 to view a stereoscopic image of the surgical worksite, the operator's head sets off the viewing sensor 320 to enable the control of the robotic surgical tools 101. When the operator's head is removed the area of the display 312, the viewing sensor 320 can disable or stop generating new control signals in response to movements of the touch sensitive handles in order to hold the state of the robotic surgical tools.

The arm support 314 can be used to rest the elbows or forearms of the operator O (typically a surgeon) while gripping touch sensitive handles of the control input 160, one in each hand, in the workspace 316 to generate control signals. The touch sensitive handles are positioned in the workspace 316 disposed beyond the arm support 314 and below the viewer 312. This allows the touch sensitive handles to be moved easily in the control space 316 in both position and orientation to generate control signals. Additionally, the operator O can use his feet to control the foot-pedals 318 to change the configuration of the surgical system and generate additional control signals to control the robotic surgical instruments.

The computer 151 may include one or microprocessors 302 to execute instructions and a storage device 304 to store software with executable instructions that may be used to generate control signals to control the robotic surgical system 100. The computer 151 with its microprocessors 302 interprets movements and actuation of the touch sensitive handles (and other inputs from the operator O or other personnel) to generate control signals to control the robotic surgical instruments 101 in the surgical worksite. In one embodiment of the invention, the computer 151 and the stereo viewer 312 map the surgical worksite into the controller workspace 316 so it feels and appears to the operator that the touch sensitive handles are working over the surgical worksite.

Surgical instruments 101A,101C on the robotic surgical arms 158A,158C with the strap drive typically include elongated shafts, with proximal and distal ends. End effectors are generally mounted on wrist-like mechanisms pivotally mounted on the distal ends of the shafts, for enabling the instruments to perform one or more surgical tasks. Generally, the elongated shafts of surgical instruments allow the end effectors to be inserted through entry ports in a patient's body so as to access the internal surgical site. Movement of the end effectors is generally controlled via master controls on the control console 150.

Referring now to FIG. 4A, surgical instrument 428 generally includes an elongated shaft 430 having a proximal end 433 and a distal end 431, a pivot 432, an end effector 438 disposed at the distal end, and an instrument base 434 disposed at the proximal end. Base 434 is generally configured to releasably engage an interface member of the robotic surgical system, such as robotic surgical system 110 in FIG. 1. In general, instrument 428 is engaged with the system via base 434 such that instrument 428 is releasably mountable on a carriage which can be driven to translate along an insertion axis.

With reference to FIGS. 4A-4B, shaft 430 is rotatably mounted on base 434 for rotation about an axis 429 extending longitudinally along the shaft 430 as indicated by the arrows A. Thus, when mounted on a surgical manipulator or robotic surgical arm assembly 158A,158C; an end effector 438 may have a plurality of degrees of freedom of movement relative to manipulator arm 158A,158C, in addition to actuation movement of the end effector itself. The instrument may be translated along an insertion axis. Typically, the instrument degrees of freedom include rotation about the axis 429 as indicated by arrows A, and in the case of instruments 428 including pivots 432, angular displacement as a whole about pivot 432 as indicated by arrows D. Alternatively, the distal pivoting degree of freedom may be omitted. A single pivot wrist, a multi-pivot wrist, a distal roll joint mechanism, or other joints or wrist-like mechanisms may be included to provide additional operational degrees of freedom to the end effector. Movement of end effector 438 relative to manipulator arm 158A,158C controlled by appropriately positioned actuators, such as electric motors, or the like, which respond to inputs from an associated master control at the control station 150, so as to drive the end effector 438 to a required orientation as dictated by movement of the associated master control.

Referring now to FIG. 4B, base 434 of surgical instrument 428 suitably includes transmission members 470, 472, 474, and 476, which include spools secured on shafts 470.1, 472.1, 474.1, and 476.1. Ends of shafts 470.1, 472.1, 474.1, 476.1 generally extend from a side 477 of base 434 to a mounting plate 478 within base 434 and are configured to rotate. Generally, the ends of shafts 470.1, 472.1, 474.1, 476.1 at side 477 of base 434 extend through side 477, to an outer surface of side 477 (not shown). At the outer surface, each shaft 470.1, 472.1, 474.1, 476.1 includes an engaging member (not shown) configured to releasably couple with a complementary engaging member (not shown) rotatably mounted on the carriage of a robotic arm assembly 158A,158C. The engaging members on carriage are generally coupled to actuators (not shown), such as electric motors or the like, to cause selective angular displacement of each engaging member on the carriage in response to actuation of its associated actuator. Thus, selective actuation of the actuators is transmitted through the engaging members on the carriage, to the engaging members on the opposed ends of the shafts 470.1, 472.1, 474.1, 476.1 to cause selective angular displacement of the spools 470, 472, 474, 476. Where more or fewer degrees of freedom are desired, the number of spools may be decreased or increased.

Robotic Surgical Arms with Multiple Control Straps

Referring now to FIG. 5A, a perspective view of the robotic surgical arm 158A,158C is illustrated. As discussed previously, the robotic surgical arms 158A,158C are for coupling to robotic surgical tools 101A,101C such as the robotic surgical tool 428 illustrated in FIGS. 4A-4B. The robotic surgical arm 158A,158C includes serial links 541-544 pivotally coupled in series at joints 512-514 near respective ends of the links. The first link (Link 1) 541 is pivotally coupled to a drive mount 540 at a first joint 511 near a first end and the second link (Link 2) 542 at the second joint 512 near a second end. The third link (Link 3) 543 is pivotally coupled to the second link 542 near a first end and pivotally coupled to the fourth link (Link 4) 544 near a second end. Generally, the fourth link is substantially in parallel to the insertion axis 574 of the robotic surgical tool. A fifth link (Link 5) 545 is slidingly coupled to the fourth link 544. A sixth link (Link 6) 546 is slidingly coupled to the fifth link 545. Various types of surgical tools 428 couple to the sixth link 546.

The robotic surgical arms 158A,158C further include a mounting base 540 that allows them to be mounted and supported by set-up arms/joints of a cart mount, ceiling mount, floor/pedestal mount, or other mounting surface of a patient side system. The mounting base 540 is pivotally coupled to the first link 541 to yaw the serial linkage of the robotic surgical arm about a yaw axis.

Figure 8A:
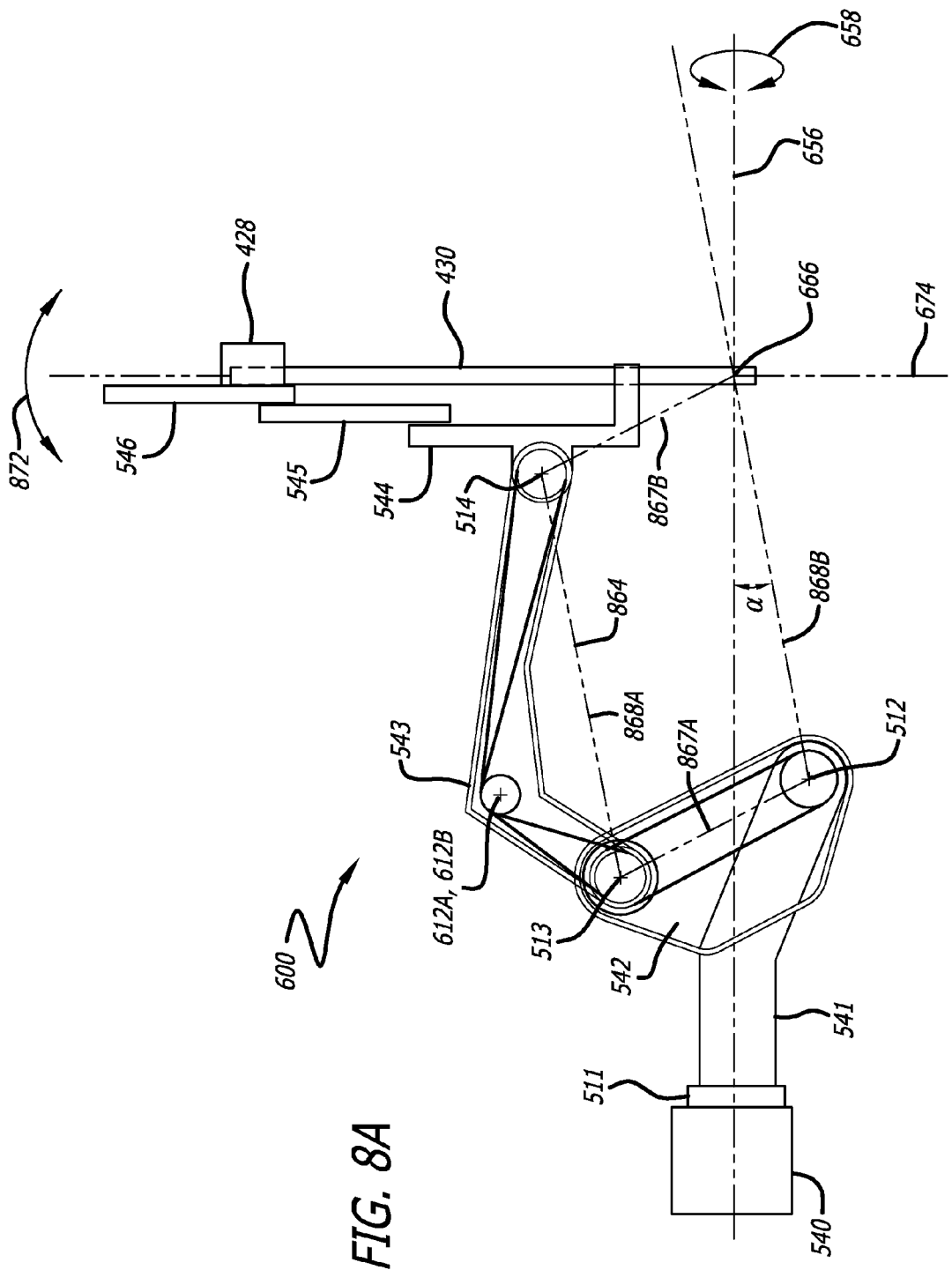
FIGS. 8A-8C are side views of the first multi-strap drive train to illustrate the range of pitch motion in the robotic surgical arm about the remote center.
Figure 8B:
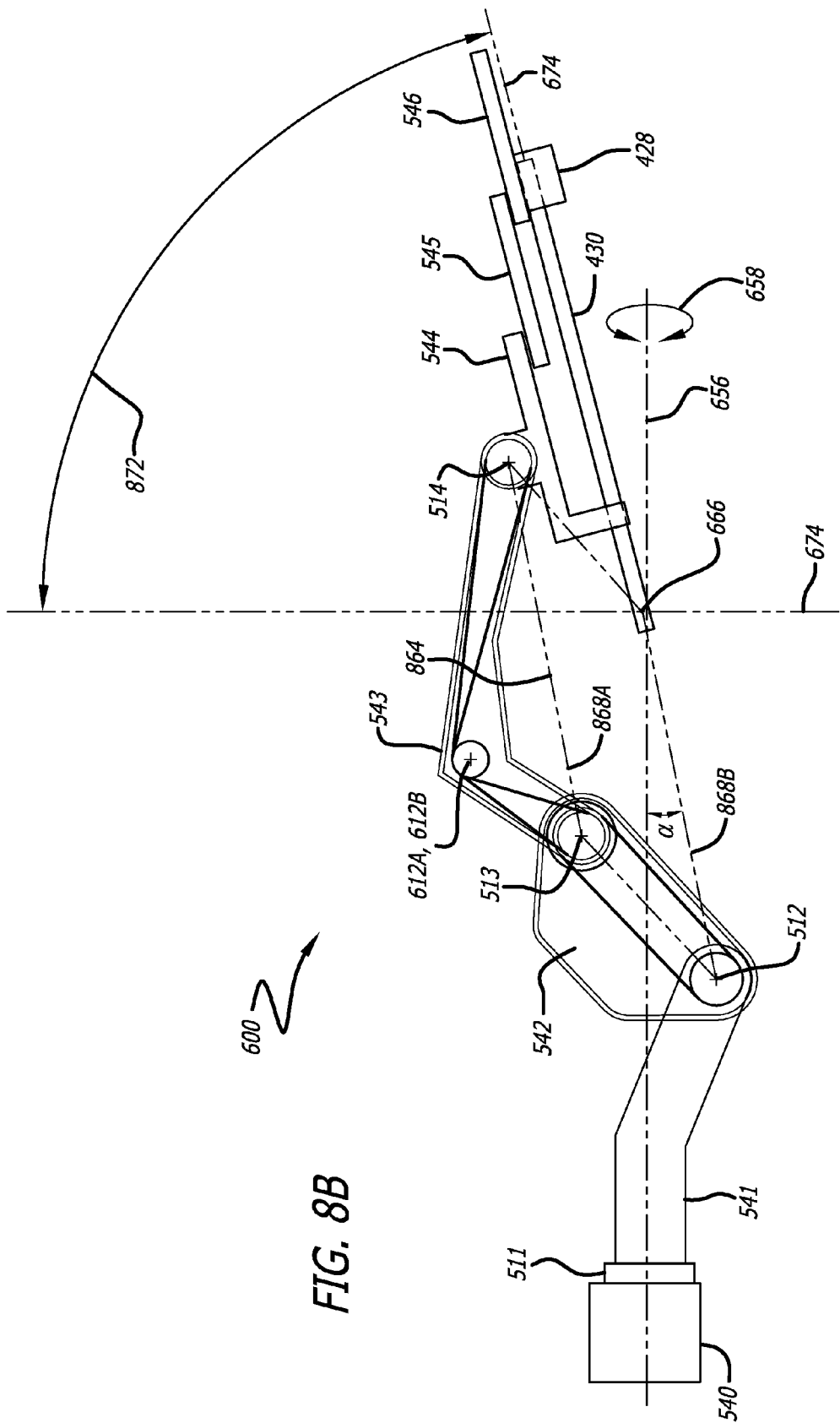
Figure 8C:
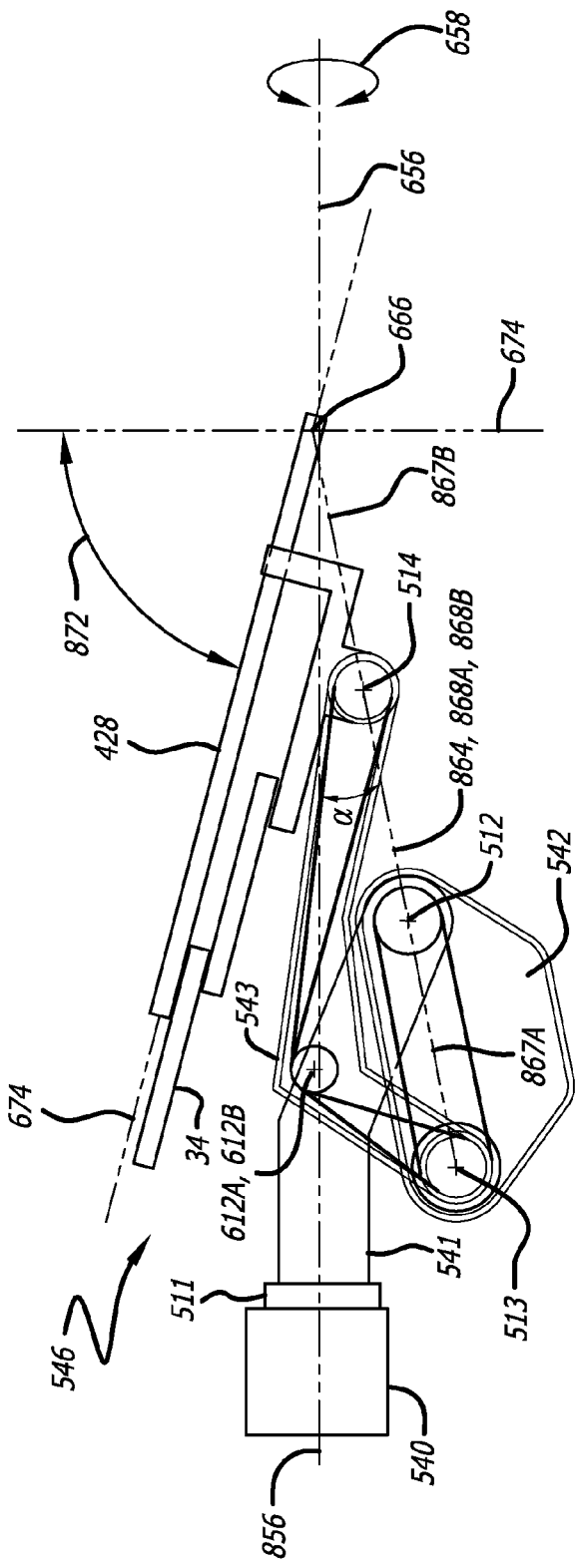

The third link 543 has a bend with respect to the pitch axis that is offset from center. The bend in the third link allows the links 542-544 to be brought more closely together and provide a greater range of pitch in the robotic arm, as is illustrated in FIGS. 8A-8C. The bend may be formed at different angles depending upon the lengths and shapes of the other links. With the bend, the third link is shaped somewhat like a hockey stick. Thus, the third link 543 may alternately be referred to as a bent link, the main bent link, or a hockey stick shaped link. The first link 541 is shaped to be offset from the yaw axis and also has a bend with respect to the pitch axis as is illustrated by FIGS. 5A-5B and 6A. With no yaw, the second link 542 provides a vertical motion in the third link 543. Additionally, the second link 542 may house the motor to drive the linkage of the arm. Thus, the second link 542 may also be referred to as the vertical link or the drive link. As the fourth link 544,544' typically slidingly holds the robotic surgical tool or the endoscopic camera through the fifth and sixth links, the fourth link may also be referred to as the instrument holder link.

Referring now to FIG. 5B, a perspective view of the robotic surgical arm 158B is illustrated. As discussed previously, the robotic surgical arm 158B is for coupling to an endoscopic camera 101B. The robotic surgical arm 158B is of a simpler design in that it may have fewer links as illustrated. Additionally, an endoscopic camera does not have an end effector that is controlled so that fewer motors, cables, and pulleys may be employed. However for the purposes of overall movement (i.e., pitch and yaw) to which the embodiments of the invention pertain, the elements of the robotic surgical arm 158B are similar to the elements of the robotic surgical arms 158A, 158C. The robotic surgical arm 158B includes serial links 541-543,544' pivotally coupled in series at joints 512-514 near respective ends of the links. The links 541-543 and joints 512-514 are generally described previously with respect to FIG. 5A and not repeated here for brevity. The third link (Link 3) 543 is pivotally coupled to the second link 542 near a first end and pivotally coupled to the fourth link (Link 4) 544' near a second end. Generally, the fourth link 544' is substantially in parallel to the insertion and optical axes 574 of the endoscopic camera 101B. A fifth link (Link 5) 545' is slidingly coupled to the fourth link 544'. The endoscopic camera 101B mounts to the fifth link 545' as shown in FIG. 5B.

As discussed previously, alternate terms may be applied to the links 541-542 herein. The first link 541 may be referred to as an offset yaw link 541 or a parallelogram linkage base 541. The second link 542 may be referred to as a lowered vertical link 542 or drive link 542. The third link 543 may be referred to as the main bent link 543. The fourth link 544 may be referred to as the instrument holder link 544. Links 541-543 may also be referred to as rigid links. Additionally, the term "joint" may be used interchangeably herein with the term "pivot".

In robotic surgical systems for minimally invasive surgery, it is desirable to move and constrain a robotic surgical tool substantially at a single fixed remote center point 666. Typically the fixed remote center point 666 is near the point of insertion of the surgical tool into the patient P. The center of rotation 666 may be aligned with the incision point to the internal surgical site, for example, by a trocar or cannula at an abdominal or thoracic wall during laparoscopic or thorascopic surgery. As the fixed remote center point 666 is on an insertion axis 574 of the surgical tool and the robotic camera and is offset and remote from ground, the embodiments of the robotic surgical arm may also be referred as an offset remote center manipulator instead of robotic surgical arm or surgical manipulator.

The robotic surgical arms 158A-158C have a strap and pulley drive train system to control the pivoting of the links about the joints 512-514. The term "strap" may be used interchangeably with the terms "belt" and "band" herein to mean a segment of one or more material layers that are not formed in a continuous loop. If a continuous loop of one or more material layers is to be referenced herein, the phrase "continuous belt" or loop may be used. As the links of the robotic surgical arms 158A-158C do not rotate more than three hundred sixty degrees about the joints 512-514, instead pivoting less than three hundred sixty degrees about the joints 512-514, straps may be used to couple to the pulleys of the drive train system.

Figure 6B:
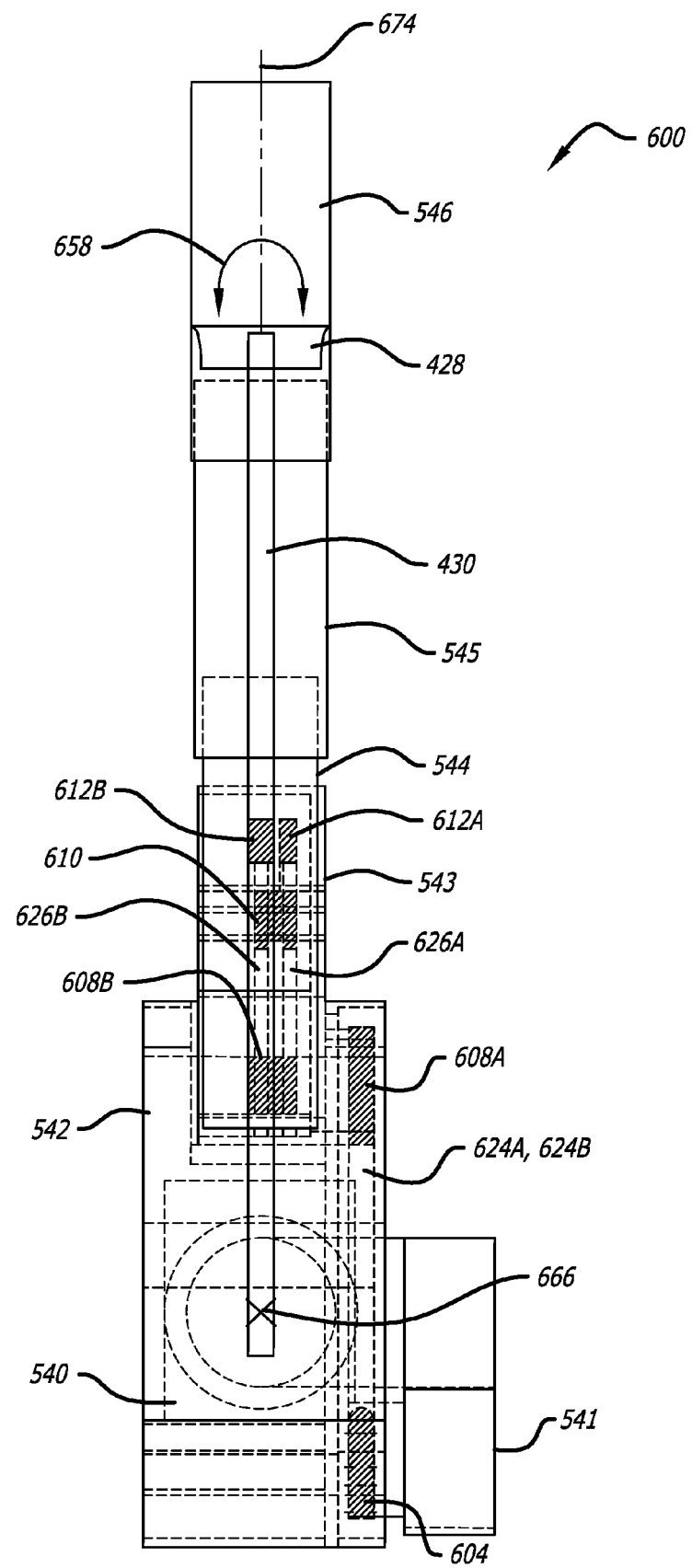
Figure 6C:
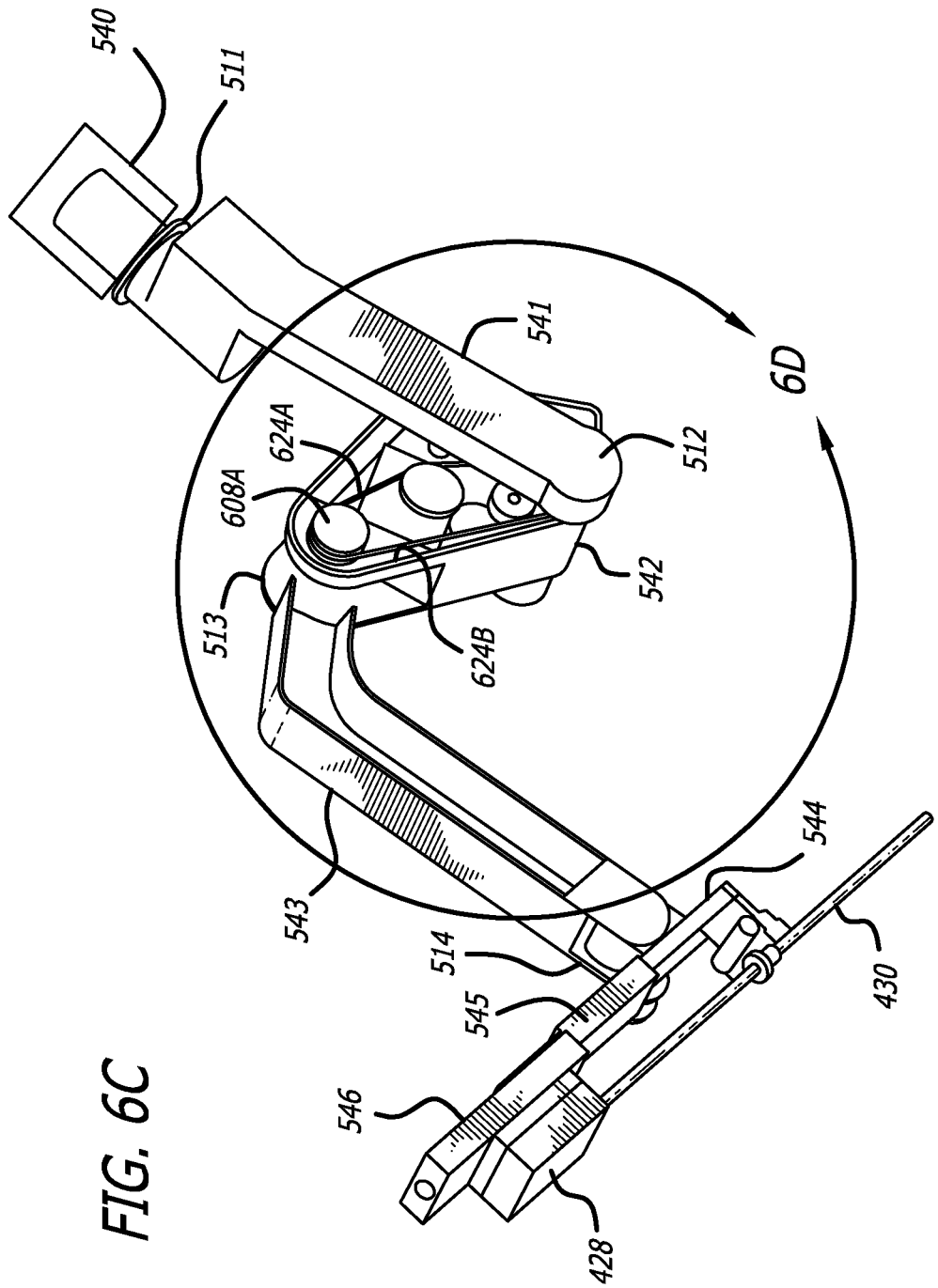
FIGS. 6C-6E are various perspective views of the linkages in the robotic surgical arm with panels removed to reveal the first multi-strap drive train.
Figure 6D:
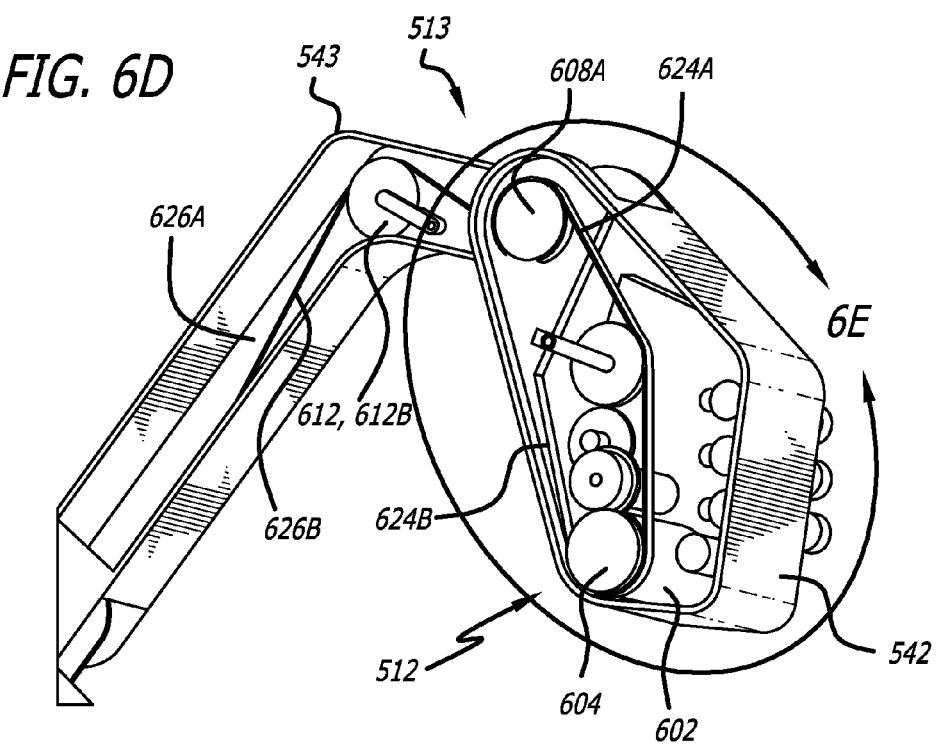

Referring now to FIGS. 6A-6B, a schematic diagram of the strap drive train of a first embodiment of a robotic surgical arm 600 is illustrated. Perspective views of the robotic surgical arm 600 including the strap drive train are illustrated in FIGS. 6C6-6D. The strap drive train of the robotic surgical arm 600 may be used in the structure of the arms 158A-158C illustrated in FIGS. 1, 2, 5A-5B in one embodiment of the invention. The strap drive train of the robotic surgical arm 600 drives the weight or load of the robotic arm itself from the links, joints, pulleys, cables, straps, etc. and the load that may be placed on it by the surgical tool in the surgical site. Without the strap drive train, the robotic arm would collapse and a remote center point 666 would not be maintained.

While the robotic surgical arm 600 includes links and joints as described herein, the strap drive train of the robotic surgical arm 600 includes six pulleys 604, 608A, 608B, 610, 612A, 612B and four straps 624A, 624B, 626A, 626B in one embodiment of the invention. The six pulleys 604, 608A, 608B, 610, 612A, 612B and four straps 624A, 624B, 626A, 626B are configured with the links and joints or the robotic surgical arm 600 to constrain the motion of the shaft 430 of the surgical tool or endoscopic camera relative to the center of rotation 666.

In the second link 542, straps 624A-624B are coupled between pulleys 604 and 608A. In the third link 543, the straps 626A-626B are coupled between pulleys 608B,610 and ride over the idler pulleys 612A,612B, respectively, in one embodiment of the invention. At the second joint, pulley 604 is rigidly coupled to the first link 541. At the third joint 513 as is illustrated in the FIGS. 6A-6B and 7A-7B, pulleys 608A and 608B are concentric but have a separation that allows them to freely rotate independent of each. However at the third joint 513, pulley 608A is rigidly coupled to the third link 543 and pulley 608B is rigidly coupled to the second link 542. At the fourth joint 514, pulley 610 is rigidly coupled to the fourth link 544.

Figure 6E:
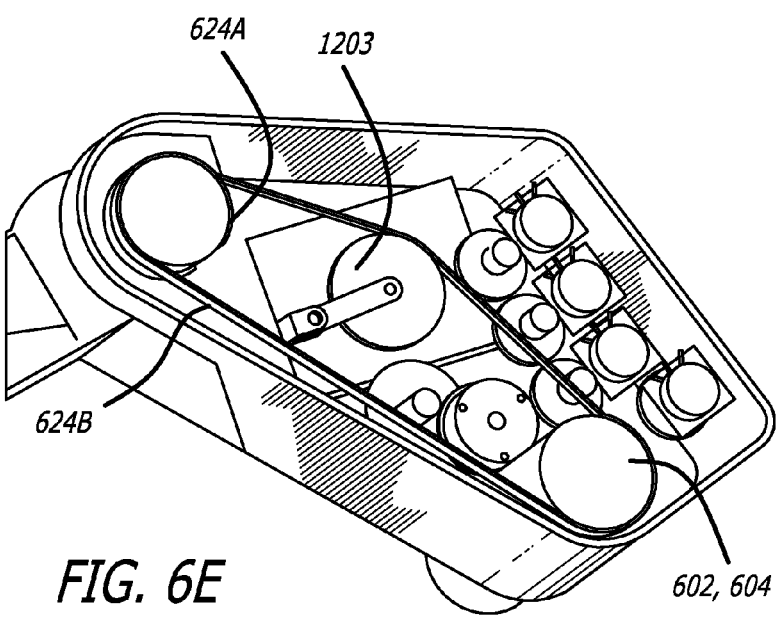

As illustrated better in FIGS. 6C-6E, the first link may have a hollow solid body to route electrical cabling for power, ground, and control signaling. The second link 542 has a housing that is somewhat "D" shaped to support a plurality of motors in a compact structure. Panels of the housing may be removed to gain access to the motors and the drive straps for assembly and maintenance purposes. As discussed further herein, the third link 543 has a housing shaped like a hockey stick with a bend to support the increased motion of the robotic surgical arm as is further described herein. The housing of the third link also has panels on top and to the sides that may be removed to gain access to the drive straps and the pulleys.

Figure 7A:
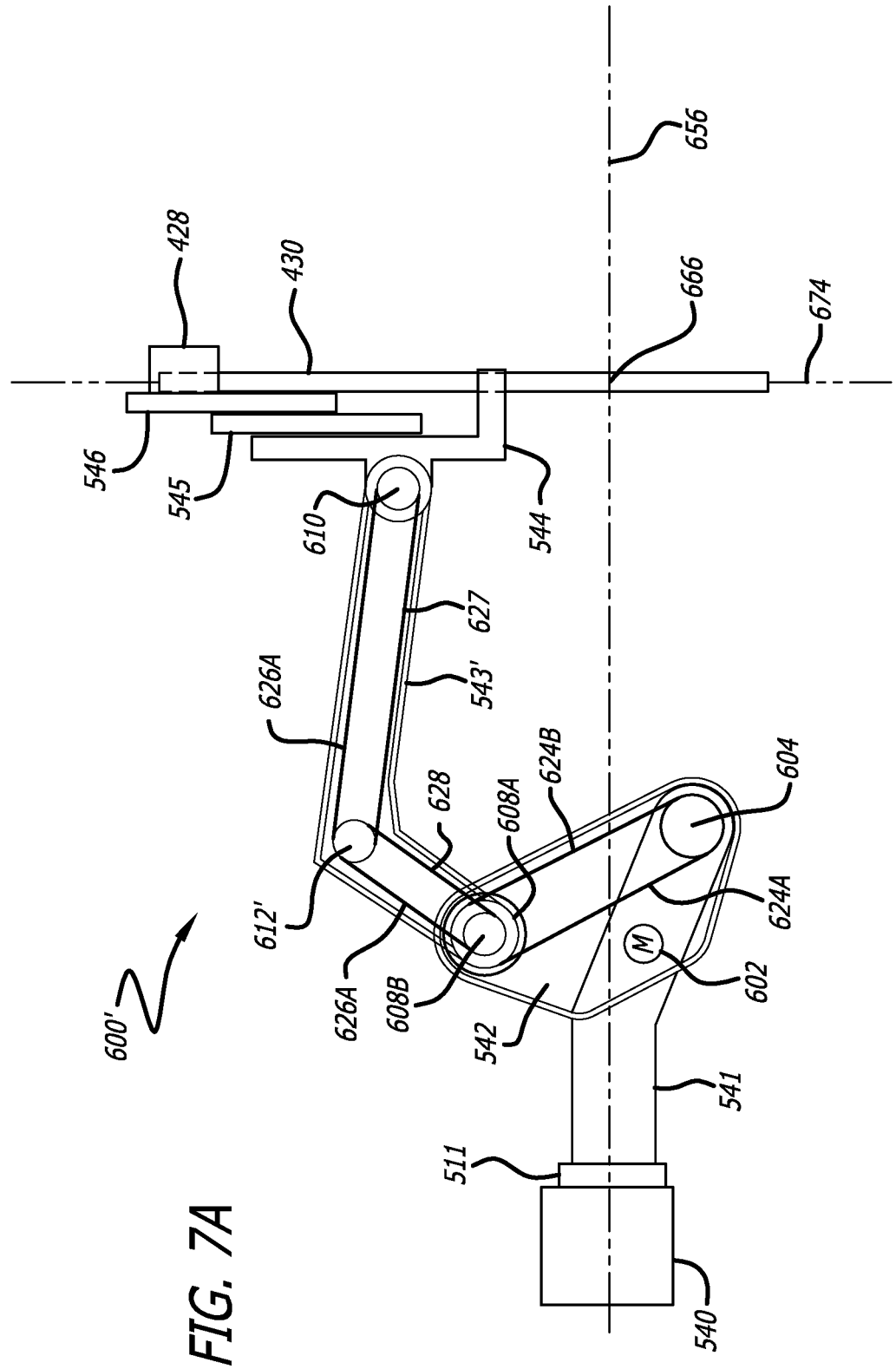
FIGS. 7A-7B are schematic side views of a second multi-strap drive train having a three-strap system in a third link.
Figure 7B:
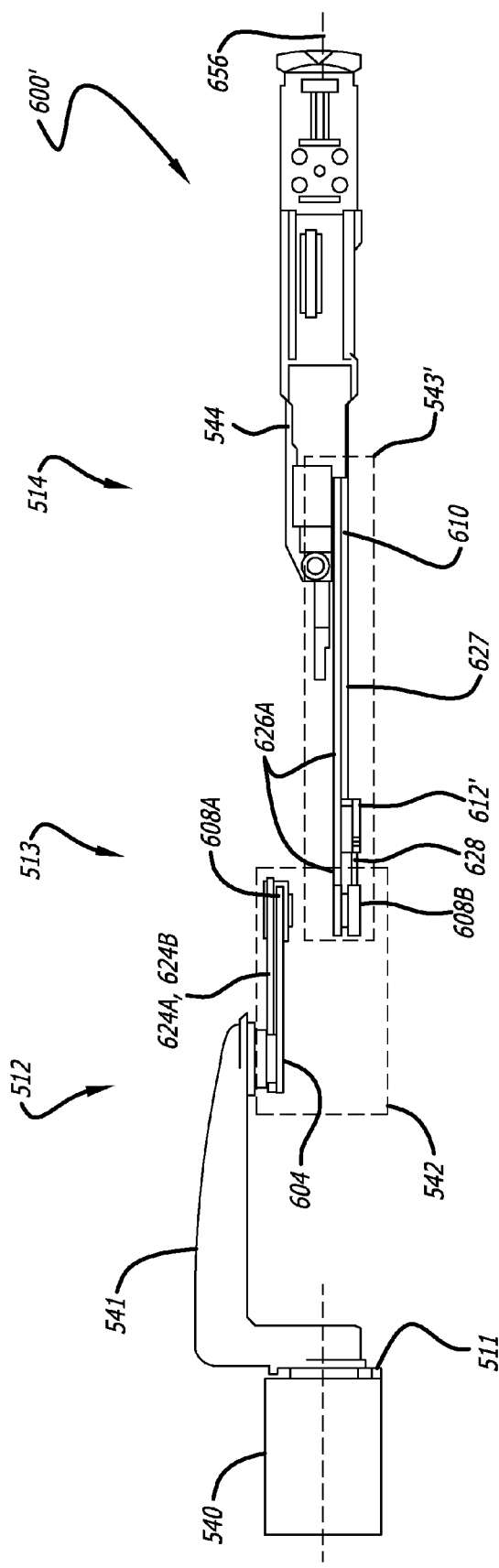

Referring now to FIGS. 7A-7B, a robotic surgical arm 600' is illustrated as a preferred embodiment of the invention. FIG. 7B illustrates a top view of the robotic surgical arm 600' in a fully pitched position to better see the strap drive train. While the robotic surgical arm 600' includes links and joints of the surgical arm 600 as described herein, the strap drive train differs in the third link 543' in that it includes three straps. The differences in the third link 543 and 543' are better seen in the illustrations of FIGS. 9A-9B and 10A-10B and understood by the description thereof that is found herein.

The strap drive train of the robotic surgical arm 600' includes five pulleys 604, 608A, 608B, 610, 612' and five straps 624A, 624B, 626A, 627, 628 in one embodiment of the invention. The five pulleys 604, 608A, 608B, 610, 612' and five straps 624A, 624B, 626A, 627,628 are configured with the links and joints of the robotic surgical arm 600' to constrain the motion of the shaft 430 of the surgical tool or endoscopic camera relative to the center of rotation 666.

In the second link 542, straps 624A-624B are coupled between pulleys 604 and 608A. In the third link 543', a single idler pulley 612' may be used. In the third link 543', the strap 626A is coupled between pulleys 608B, 610 and rides over the idler pulley 612'; the strap 627 is coupled between pulleys 612', 610; and strap 628 is coupled between pulleys 608B, 612', in this embodiment of the invention. At the third joint 513 the separation between pulleys 608A and 608B allows them to freely rotate about each other even though pulley 608A is rigidly coupled to the third link 543' and pulley 608B is rigidly coupled to the second link 542. As is illustrated in FIGS. 7A-7B, pulleys 608A-608B are concentric, independently pivoting about the same center axis. At the second joint 512, it can be better seen in FIG. 7B that the pulley 604 is rigidly coupled to the first link 541. At the fourth joint 514, pulley 610 is rigidly coupled to the fourth link 544.

With the exception of the third link 543' and the straps and pulleys therein, the robotic surgical arm 600' is substantially similar to the robotic surgical arm 600 and its description is incorporated here by reference as the same reference numbers are used, The straps 624A, 624B, 626A, 626B in the robotic surgical arms 600 and the straps 624A, 624B, 626A, 627,628 in robotic surgical arm 600' may also be referred to as flexible elements and may include straps, belts, chains, or cables connected around the pulleys 604, 608A, 608B, 610, and 612A, 612B or 612'. As described in greater detail with reference to FIGS. 9B,10B, the straps comprise multiple layers of multiple plies of metal. In one embodiment of the invention, the multiple plies of metal are formed out of stainless steel belts having a breaking strength of approximately 800 lbs or more and being about a quarter inch wide. The belts are preferably multi-layered utilizing at least two or three plies, preferably five or six plies to be strong enough to carry an adequate tension load yet sufficiently thin enough to not fatigue when repeatedly bent around the pulleys.

As the straps 624A, 624B and 626A, 626B or 626A,627, 628 are only segments and are offset from each other, they provide stress reduction, particularly at the attachment points, thus minimizing failures. Further, the straps allow for convenient tension and position adjustments as is further described below. It will further be appreciated that straps 624A, 624B as well as straps 626A, 626B may each optionally comprise a continuous single belt. Additionally, the metal straps may be loosely coupled to flat flex cables that carry electrical signals along the manipulator arm as further described in U.S. provisional patent application No. 60/752,788. Moreover, while the straps are preferably formed of multiple plies of metal, multi-ply belts of other materials, single-ply belts of other materials, mechanical cables, multiple mechanical cables, timing belts with teeth, or other types of drive straps may be used.

Pulleys 604 and 608A have approximately the same diameter, e.g., 2.2 inches. Smaller pulleys 608B and 610 have approximately the same diameter, e.g., 1.8 inches. In one embodiment of the invention, there are two idler pulleys 612A, 612B at the bend of the main link 543 to facilitate running of straps 626A, 626B in opposite directions so as to allow for attachment of the belts ends to be more robust. In another embodiment there is one idler pulley 612' at the bend of the main link 543' as the straps 626A,627,628 turn the pulley 612' in the same direction even though the midspans of the straps 626A,627,628 may be moving in opposite directions. However, as the three straps 626A,627,628 ride on or wrap around the idler pulley 612', it is wider at the bend than the two idler pulleys 612A,612B. It will be appreciated that the term pulley 604, 608A, 608B, 610, 612A, 612B, 612' can include wheels, gears, sprockets, pulleys with bullnose pins, and the like.

Besides straps/belts/bands and pulleys there are other drive train means that may be used in the robotic surgical arm such as a continuous toothed timing belt with a timing gear, mechanical cables (one or more in parallel together) with shouldered pulleys, chains with sprockets, continuous perforated metal tapes around pulleys with bull nose pins, as well as other like drive train.

As discussed previously, the robotic surgical manipulator or robotic surgical arm 600 includes a plurality of links 541-544 coupled together through a series of joints 511-514. The first link 541 also referred to as the parallelogram linkage base 541 supports the instrument holder link 546 through the rigid links 542, 543 coupled together by the rotational pivot joints 512, 513, 514.

Using alternate terminology, the links of the robotic surgical arm include an offset yaw link 541, a lowered vertical link 542, and a main bent link 543. The main link 543 is bent at an angle so as to provide clearance for the vertical link 542 to rest on the main bent link 543. This clearance prevents inter-linkage collisions between the vertical link 542 and the main bent link 543. For example, the main link 543 may be bent at an angle of about twenty-two degrees to allow clearance over a pitch dive 872 as shown in FIG. 8C. In such an embodiment, the main bent link 543 and the vertical link 542 as well as the instrument holder 546 are located in the same plane. It will be appreciated however that the main link 543 and the vertical link 542 may alternatively be offset in different planes (i.e., placed side by side) to reduce inter-linkage collisions in lieu of bending main link 543. The vertical link 542 pivot 512 is lower relative to the yaw axis 656 so as to provide the offset parallelogram 864 arrangement discussed further below. The yaw link 541 is offset from links 542, 543. That is, the yaw link 541 and links 542, 543 are not in the same plane, but are rather offset side by side so as to reduce the possibility of inter-linkage collisions between link 541 and links 542, 543.

At the center of rotation 666, three axes intersect and may be defined for the robotic arm 600. A yaw axis 656 about which the robotic arm rotates, a pitch axis (which is perpendicular to the page) about which the robotic arm pitches, and an insertion axis 674 along which the shaft 430 is moved intersect with each other at the remote center 666.

The surgical tool 428 can be pivotally rotated though desired yaw angles 658 around the yaw axis 656 and pivotally rotated though desired pitch angles 872 around the pitch axis (see FIGS. 8A-8C), while the remote center of rotation 666 remains at a fixed point in space relative to the mounting base 540 and set up arm 156,156'. The links and joints of the entire manipulator 600 are generally moved by the strap drive train to maintain and re-position the remote center 666 while the surgical tool 428 is being pitched and yawed. It will further be appreciated that the surgical tool 428 still has further degrees of freedom supported by the robotic arm 600, including a sliding motion of the surgical tool along the insertion axis 674.

Referring now momentarily to FIGS. 8A-8C, for the robotic surgical arm 600 to move the shaft 430 of the robotic surgical tool 428 about the single fixed remote center point 666 during minimally invasive robotic surgery, an offset remote center parallelogram manipulator linkage assembly (links 541-544 and joints 511-514) is provided. In conjunction with the strap drive train, the offset remote center parallelogram manipulator linkage assembly (links 541-544 and joints 511-514) defines a parallelogram 864 (illustrated in FIG. 8A-8C) so as to constrain the elongated shaft 430 of the instrument 428 relative to the center of rotation 666 when the instrument 428 is mounted to the instrument holder 546 and the shaft 430 is moved along a plane of the parallelogram 864.

A top long side 868A of the parallelogram 864 is defined as the distance between axes of rotation at joints 513 and 514 generally defined by the third link 543. A left short side 867A of the parallelogram is defined as the distance between axes of rotation at joints 512 and 513 generally defined by the second link 542. The strap drive train is assembled in the robotic arm with the pulleys in proper positions in order to define the bottom long side 868B and the right short side 867B of the parallelogram.

Note that the yaw axis 656 and the parallelogram 864 intersect the insertion axis 674 of the shaft 430 at the remote center of rotation 666. Also note that the parallelogram 864 is angularly offset from the yaw axis 656 by an angle Alpha. That is, the robotic arm 600 offsets or decouples the first joint 512 and the first side 868B of the parallelogram 864 from the yaw axis 656 by the angle Alpha. The angle Alpha may be in a range from about two degrees to about forty five degrees and preferably falls in a range from about two degrees to about thirty five degrees. This offset enhances the range of motion in the instrument 428 about the remote center point 666 relative to the pitch axis, as indicated by arrow 872. The manipulator 600 further allows for an enhanced range of motion relative to the yaw axis 656, as indicated by arrow 658. An improved pivot range of motion along pitch and yaw axes in turn enhances the efficiency and ease of use of the robotic surgical arm in a robotic surgical system.

As FIGS. 8A-8C illustrate, when the robotic surgical arm 600 is pitched, the first link 541 and the third link 543 are kept from rotating relative to each other by the straps 624A, 624B coupled between the two pulleys 604, 608A and by the pulley 604 being rigidly fixed to the first link 541 and pulley 608A being rigidly fixed to the third link 543. That is, the third link 543 can be translated by the second link 542, but the angular orientation of third link 543 with respect to first link 541 is substantially the same.

The second link 542 and the fourth link 544 are likewise kept from rotating relative to each other. In one embodiment of the invention, this is accomplished by the straps 626A, 626B coupled between pulleys 608B and 610 and running over the idler pulleys 612A, 612B; and by pulley 608B being rigidly fixed to the second link 542 and by the pulley 610 being rigidly fixed to the fourth link 544. In another embodiment of the invention, this is accomplished by the strap 626A coupled between pulleys 608B and 610 running over the idler pulley 612'; and strap 628 coupled between pulleys 608B, 612' and strap 627 coupled between pulleys 612',610; with pulley 608B being rigidly fixed to the second link 542 and pulley 610 being rigidly fixed to the fourth link 544.

Hence, links 541 and 543 can translate but not rotate relative to each other to maintain the parallelogram shape 864. Likewise, links 542 and 544 can translate but not rotate relative to each other to maintain the parallelogram shape 864.

The mounting base 540 includes a motor 601 illustrated in FIG. 6A to yaw the robotic arm 600 about the axis 656 as illustrated by the arrow 658 in FIGS. 6A, 6B, and FIGS. 8A-8C. The mounting base 540 includes electrical and mechanical connectors 652 to mate with electrical and mechanical connectors 650 in a base support coupled to the set up arm 156,156'. Additionally, fasteners 662 (such as bolts) may be used to rigidly couple the robotic surgical arm 600 to the set up arm 156,156'. Alternatively, a lever arm may be used to lock and unlock the arm 600 from the arms 156, 156' to quickly mount and dismount the robotic surgical arm from the patient side system.

The second link 542 includes a motor 602 coupled to the pulley 604 to pitch the robotic arm 600 as illustrated in FIGS. 8A-8C. The motor may couple to the pulley through spur gears and a harmonic drive. The motor 602 in the second link 542 pivots the second link at the shaft and axis of the pulley 604 at the second joint 512 that in conjunction with the other elements, causes the robotic arm 600 to pitch. The motor 602 actively moves the linkage of the arm 600 in response to commands from a computer processor 151 generated by the control input 160 at the console 150. Additional motors (shown in FIG. 6E) are mounted in the links of the robotic arm 600 to articulate a wrist 431 at the distal end of the tool 428 about at least one, and often two, degrees of freedom. An addition motor (shown in FIG. 6E) can be used to actuate an articulatable end effector 438 of the tool 428 for grasping tissues in the jaws of a forceps or the like. Control cables may be used to couple the motors to the controllable features of the tool 428, as more fully described in U.S. Pat. No. 5,792,135, the full disclosure of which is incorporated herein by reference.

At least one of the rigid links 541, 542, 543 coupled together by rotational pivot joints 512, 513, 514 are not completely balanced, relative to gravity, in at least one degree of freedom. As such, a brake system may be coupled to the articulate linkage assembly 600. The brake system releasably inhibits articulation of at least one of the joints 512, 513, 514. It will be appreciated that the offset remote center manipulator 600 may comprise a lighter system as the linkage is free of any counter-balancing weights. As such, the links 541, 542, 543 will preferably comprise sufficiently rigid and stiff structures so as to support any vibration issues associated with a lighter surgical manipulator 600. It will further be appreciated that the offset remote center manipulator 600 may optionally be balanced by the use of weights, tension springs, gas springs, torsion springs, compression springs, air or hydraulic cylinders, torque motors, or combinations thereof.

Multi-Ply Straps

The straps in each link, drive the pitch axis of the robotic surgical arm. The first set of straps 624A-624B in the second link 542 are used to connect pulley 604 to pulley 608A in a 1:1 ratio (i.e., pulleys are of the same diameter). As discussed previously, joint pulley 604 is rigidly connected to the first link (Link 1) 541 and joint pulley 608A is rigidly connect to the third link (Link 3) 543. Thus, one unit of rotation of the second link (Link 2) about the second joint 512 in one direction (e.g., clockwise) causes one unit of rotation of the third link (Link 3) about the third joint 513 in an opposite direction (e.g., counter clockwise). Thus, the first set of straps ensures that the third link 543 maintains the same angle relative to the first link 541, as the robotic surgical arm's pitch axis is moved.

The second set of straps in the third link 543 are used to connect joint pulley 608B to joint pulley 610 in a 1:1 ratio. Joint pulleys 608A and 608B are free to rotate about each other at the third joint 513. As discussed previously, pulley 608B is rigidly connected to the second link (Link 2) 542 and pulley 610 is rigidly connected to the fourth link (Link 4) 544. One unit of rotation of the second link (Link 2) about the second joint 512 causes one unit of rotation of the fourth link (Link 4) about the fourth joint 514. Thus, the first and second set of straps ensures that the fourth link (Link 4) 544 maintains the same angle relative to the second link (Link 2) 542, as the robotic surgical arm's pitch axis is moved.

To provide a strap drive system linking pulleys at the joints of the bent third link 543 (the hockey stick shaped link), a pair of idler pulleys are provided near the bend in the link in one embodiment of the invention. The pair of idler pulleys direct one or more of the straps of the strap drive system in the link housing from one end to the other through the bend of the link. Thus, one or more of the straps may bend around the idler pulleys of the third link 543 to facilitate the hockey-stick shape and provide the proper kinematics and range of motion for the robotic surgical arm. As discussed previously, a two-strap drive system is used for connecting pulleys in the third link 543 in one embodiment of the invention. Alternatively, a three-strap drive system is used for connecting pulleys in the third link 543 in another embodiment of the invention.

Referring now to FIG. 9A, a perspective view of a two-strap drive system 900 used in a third link is illustrated. The system 900 includes the two straps 626A-626B, the joint pulleys 608B, 610, and the idler pulleys 612A-612B for each respective strap 626A-626B. Each of the straps partially wraps around each pulley side-by-side over a wrap angle with the ends of the straps being rigidly coupled to the joint pulleys 608B,610 so that no backlash occurs. The two straps 626A-626B are partially wrapped around the joint pulleys so as to move in opposite directions when the links are moved. That is, the ends of strap 626A are wrapped around each joint pulley in an opposite direction than how the ends of strap 626B are wrapped. Even though the two straps 626A-626B are routed side by side in the link housing, effectively they act as one continuous loop between the joint pulleys. However, the straps may be used as the pulleys pivot less than three hundred sixty degrees.

Because the third link (Link 3) 543 has a bend in it (e.g., the third link may be referred to being hockey-stick shaped), each strap 626A-626B wraps around it's own respective idler pulley 612A-612B, because the belts rotate in opposite directions about them. The idler pulleys 612A, 612B allow the straps 626A, 626B to navigate around the bend in the third link 543. In one embodiment of the invention, the idler pulleys are also used to tension the straps as discussed further below. Otherwise, the idler pulleys are passive idlers.

The system 900 may be advantageous for single-ply straps or cables, as it requires only two straps. However in a number of embodiments of the invention, the straps are formed of a plurality of layers or plies of material. In a preferred embodiment of the invention, each of the straps includes a plurality of metal layers or plies. The plurality of layers or plies provides a safety redundancy over that of a single cable or single ply strap or belt. If any single ply breaks in a multi-ply strap due to a manufacturing defect, fatigue, or overload for example, the remaining plies prevent the robotic surgical arm from collapsing.

Referring now to FIG. 9B, a cut-away side view of strap 626A is illustrated. Strap 626A includes a plurality of metal layers or plies 902A-902N each having the same width and thickness. The plurality of metal layers or plies 902A-902N are stacked one on top of the other and may jointly be referred by reference number 901A. In one embodiment of the invention, each metal layer 902A-902B is steel. Alternatively, other types of metal, alloy, or other materials can be used. There is no adhesive between the metal layers so they are allowed to freely move over each other at midspan and over the idler pulley. This helps to reduce the stress in the layers of the belt while the plurality of layers provides a high stiffness and strength. Instead, the multiple metal layers or plies 901A are only joined together at their ends such as by a tab 912 as illustrated in FIG. 9D. The layers may be joined to the tab 912 by welding in one embodiment of the invention. Other devices may be used to join one or both ends of the multiple metal layers or plies together, such as a hooked tab or tensioning block, as is described further below.

In the two belt system, strap 626B is reverse bent over the idler pulley in comparison with how it wraps around the joint pulleys. That is, one side of the strap wraps around the joint pulleys while the opposite side wraps around the idler pulley. This can cause increased fatigue in the strap 626B unless alleviated by its design.

Referring now to FIG. 9C, a cut-away side view of strap 626B is illustrated. Strap 626B includes a plurality material layers 901B. The plurality of material layers 901B includes metal layers 902A-902B sandwiching a layer 904 of antifriction material such as a layer of Teflon, carbon, grease, oil or other type of dry or wet lubricant. The antifriction material layer 904 allows the metal layers 902A-902B to more freely slide against each other as the strap is reverse bent over the idler pulley. Additional pairs of antifriction material layer 904 and metal layers 902 may be stacked on top of the prior metal layer to provide additional strength for the strap. The metal layers or plies 902A-902B each have the same width and thickness. Similar to strap 626A, the material layers 901B are only joined together at the ends of the strap a tab 912 as illustrated in FIG. 9D. The metal layers may be joined to the tab 912 by laser welding in one embodiment of the invention.

The multi-ply metal straps are an enabling technology for the robotic surgical arm due to their high stiffness and strength, zero backlash, low hysteresis, low friction, compact packaging, and redundant construction for safety. Their ability to bend around idler pulleys in third link (Link 3) 543 also enables the hockey-stick shape for proper kinematics and range of motion.

In a preferred embodiment of the invention, three straps are used in the third link to couple between the joint pulleys to avoid use of an antifriction layer between plies of the strap 626B.

Figures 10A, 10B:
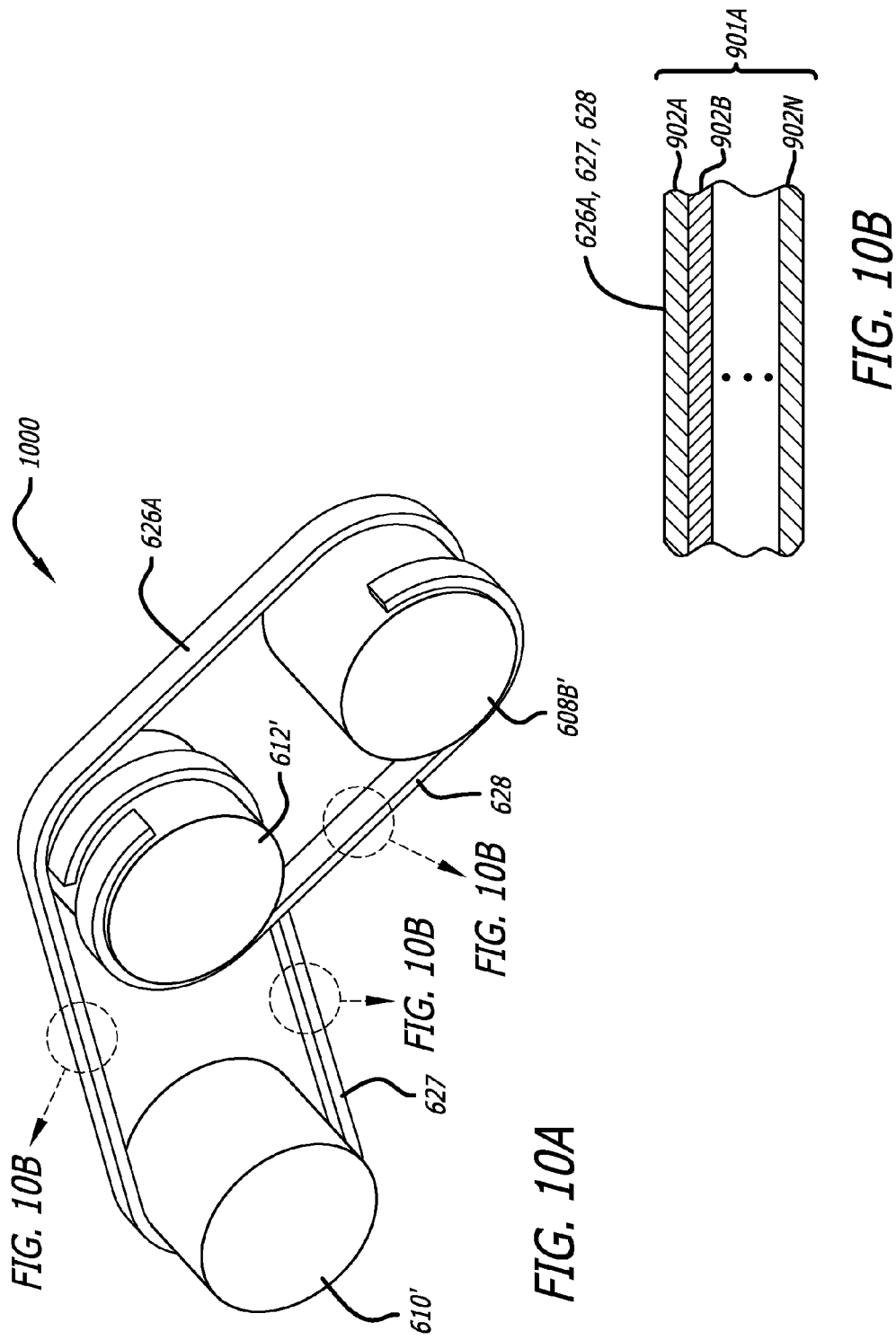
FIGS. 10A-10B are views of an exemplary three-strap system with multi-ply straps that may be used in the third link.

Referring now to FIG. 10A, a perspective view of a three-strap drive system 1000 used in a third link is illustrated. The system 1000 includes the three straps 626A,627-628; joint pulleys 608B, 610; and idler pulley 612'. Alternatively, two idler pulleys could be used; one for strap 626A, and another for straps 627, 628. In the preferred embodiment, each of the straps partially wraps around each pulley side-by-side over a wrap angle with first ends of straps 627-628 and two ends of strap 626A being rigidly coupled to the respective joint pulleys 608B, 610 and second ends coupled to the idler pulley 612' so that no backlash occurs. The straps 626A, 628 are partially wrapped around the joint pulley 608B so they will also move in opposite directions when the links are moved. The straps 626A, 627 are partially wrapped around the joint pulley 610 so they will also move in opposite directions when the links are moved. That is, the ends of strap 626A,628 are wrapped around joint pulley 608B in opposite directions and the ends of straps 626A,627 are wrapped around joint pulley 610 in opposite directions. However, while the ends of straps 627,628 are wrapped around idler pulley 612' in opposite directions, they move in the same direction (e.g., from left to right or right to left) as the links are moved. Even though the three straps are routed side by side in the link housing, effectively they act as one continuous loop between the joint pulleys. Straps may be used instead of a continuous belt as the pulleys pivot less than three hundred sixty degrees.

The idler pulley 612' is used in the system 1000 to negotiate the bend in the third link (Link 3) 543 (i.e.—hockey-stick shaped link). In one embodiment of the invention, one end of the straps may be used to generate tension in each strap between the pulleys. In another embodiment of the invention, the idler pulley 612' may be used to tension the straps. In this case, the idler pulley 612' is a passive idler.

Referring now to FIG. 10B, a cut-away side view of straps 626A,627-628 is illustrated. Without the reverse bend in the three strap system, the antifriction layer can be avoided between the layers of metal. Thus, each strap may be formed of the same layers including a plurality of metal layers or plies 902A-902N each having the same width and thickness. The plurality of metal layers or plies 902A-902N are stacked one on top of the other and may jointly be referred by reference number 901A. In one embodiment of the invention, each metal layer 902A-902B is steel. Alternatively, other types of metal, alloy, or other materials can be used. There is no adhesive between the metal layers so they are allowed to freely move over each other at midspan over the idler pulley. This helps to reduce the stress in the layers of the belt while the plurality of layers provides a high stiffness and strength. Instead, the multiple metal layers or plies 901A are only joined together at their ends by a tab 912 as illustrated in FIG. 9D. The layers may be joined to the tab 912 by welding in one embodiment of the invention.

As alluded to previously, the three strap system 1000 has some advantages. For any strap or cable (single ply or multi ply), the three-strap configuration eliminates reverse bending, to avoid fatigue caused by alternating stresses. In the case of multiple plies or layers, the three strap system eliminates pinching and stretching of plies at the idler pulley due to reverse bending, further allowing the anti-friction layer to be avoided in the formation of the straps. Another advantage of the three strap system is that a single idler pulley may be used, since all straps are being rotated in the same direction at the idler pulley 612'. Moreover, a single idler pulley may be used to tension all three straps in the system 1000.

Additionally, multi-layer or multi-ply metal straps in the drive train of the robotic surgical arm has a number of advantages over using metal mechanical cables. The multi-ply straps are more reliable, have a greater stiffness, have an excellent ability to maintain tension, and have superior strength than cables. Moreover, using conductive metal or alloy materials for the plies or layers of the metal straps assists in grounding the robotic surgical arm since they are electrically conductive.

Strap End Tabs

Figure 11A:
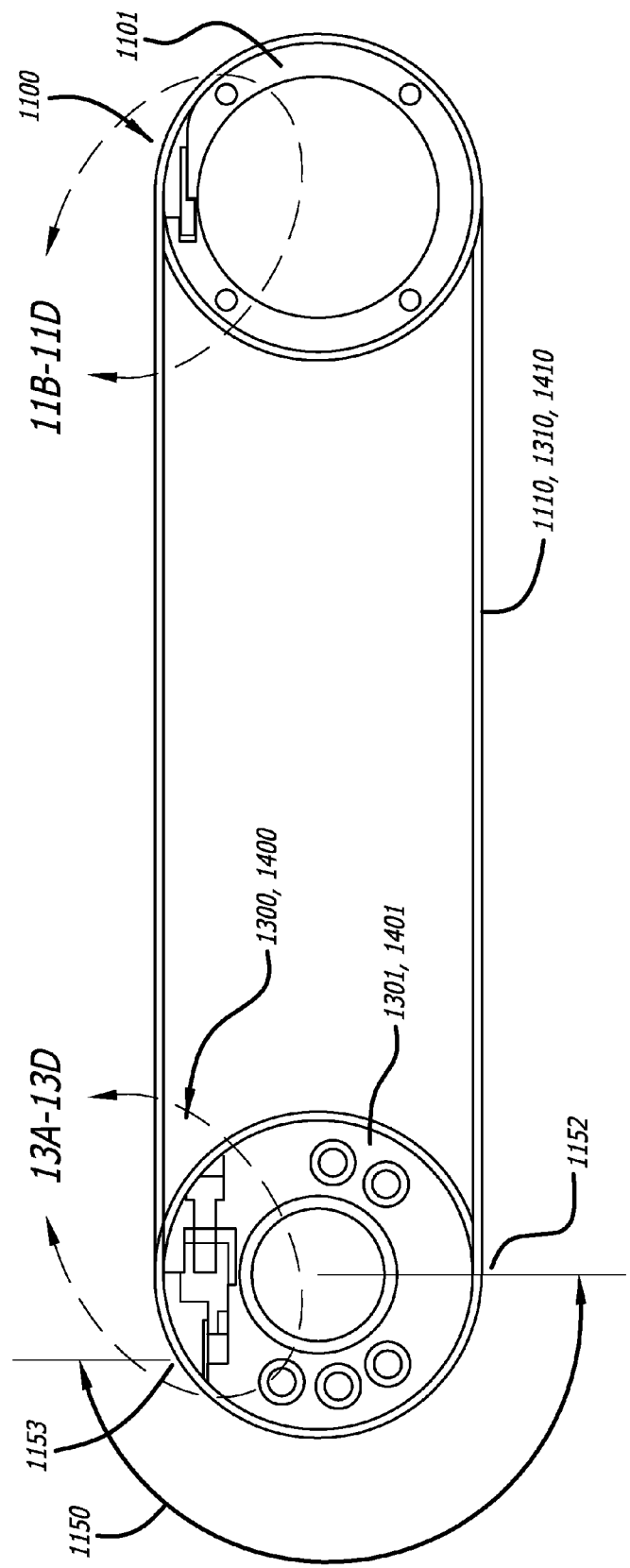
FIG. 11A illustrates an exemplary two-strap system that may be used in the second link including a hooking system and a first tensioning system to couple each end of the straps to the pulleys in the links of the robotic surgical arm.

Referring now to FIG. 11A, the straps of the robotic surgical arm may be coupled to the pulleys without use of a fastener, such as a bolt or rivet. Instead, a hooking system 1100 is used to couple one or both ends of the straps to the pulleys 1101. A tensioning system 1300,1400 may be used to couple the opposite end of the straps to the opposite pulleys 1301,1401. Use of the hooking system is advantageous in that it makes it faster and easier to replace and assemble the straps in the robotic surgical arm. Furthermore, without using fasteners, a possible failure mode is eliminated such that the hooking system is safer. Additionally, the hooking system can provide further safety by avoiding being unhooked in the event of slacking of the strap.

Figure 11B:
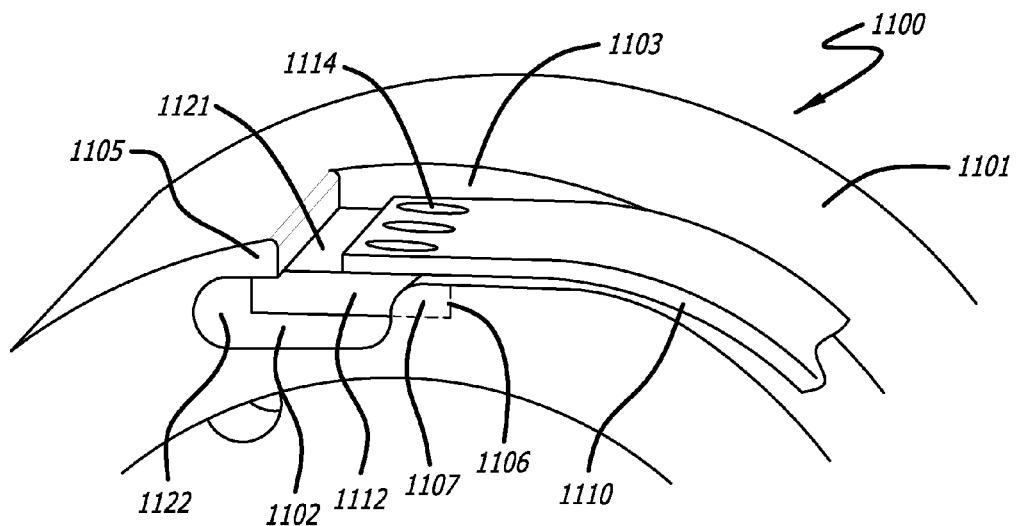
FIGS. 11B-11D illustrate magnified views of the hooking system that may be used to couple the straps to the pulleys in the links of the robotic surgical arm.
Figure 11C:
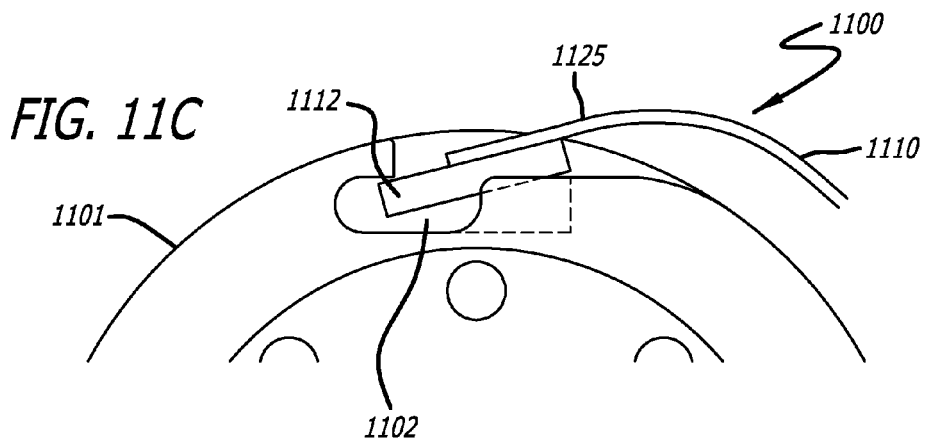
Figure 11D:
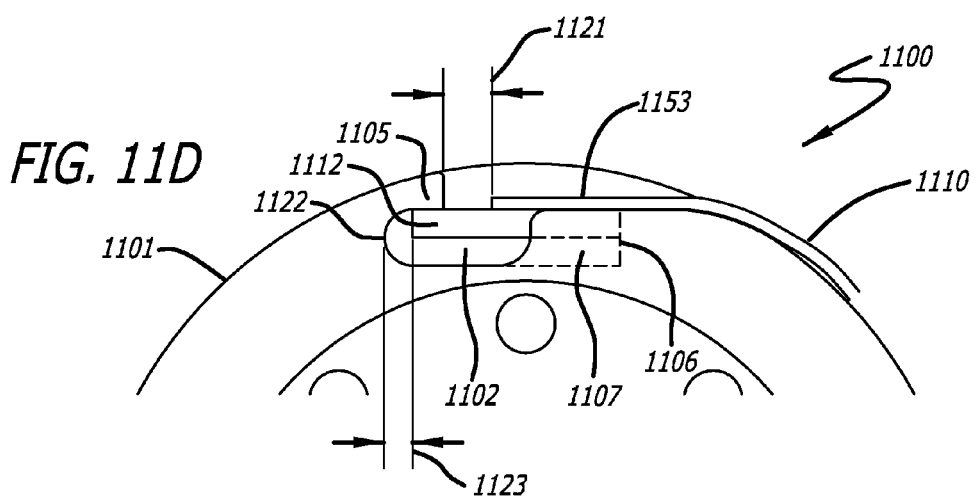

Referring now to FIGS. 11B-11D, the strap hooking system 1100 is now described. The strap hooking system 1100 includes a pulley 1101 having a pocket 1102 and a strap 1110 with an end tab 1112 coupled at an end.

To receive the end of the strap 1110, the pulley 1101 further includes a recess 1103 in its circumference that is at least as wide as the strap 1110. The recess 1103 becomes progressively deeper until it joins with the pocket 1102. The recess ends at the lip 1105.

The tab 1112 is a rectangularly shaped geometric solid (e.g., rectangular prism) in one embodiment of the invention including a front side, a back side, and left and right sides formed by a thickness of the tab. The tab 1112 further includes a bottom surface and an opposing top surface to couple to a bottom surface of the strap 1110. The width of the tab may be substantially similar to the width of the strap.

In a preferred embodiment of the invention, the strap 1110 is a metal strap having one or more layers or plies as discussed previously with reference to FIGS. 9B and 10B. In which case, the tab 1102 is preferably a metal tab and the strap 1110 may be coupled to the tab 1102 by welding as illustrated by the welds 1114. In other embodiments of the invention, the strap and tab may be coupled together by other means.

The pocket in the pulley is shaped to receive the tab 1112. The pocket 1102 includes a lip 1105 at the back of the pocket to retain the tab therein. The strap is sufficiently stiff enough to behave as a beam, which is relaxed when it is straight. When the strap is deformed around the circumference of the pulley and the tab 1112 is inserted into the pocket, the lip 1105 exerts a force on the tab to retain it in the pocket. In the strap's deformed state, it wants to straighten and exerts a load on the tab that attempts to rotate the tab clockwise with reference to the view of FIG. 11C. These loads on the tab keep it locked in place, so that it cannot be readily unhooked, even when the strap is slackened. Referring momentarily to FIG. 6A, if a sufficiently high force is applied along the insertion axis 674 in a downward direction, strap 624A inside the second link (Link 2) 542 will stretch and strap 624B will slacken. In this case, removal of the tab 1112 from the pocket is avoided so that the robotic surgical arm does not completely collapse and wildly move a surgical tool and injure a patient. Referring back to FIGS. 11B-11D, he pocket further includes a stop 1106 at the front of the pocket 1102 to couple to a front side of the tab 1112. The stop 1106 is where significant forces from the strap on the tab 1112 meet the pulley. The pocket 1102 further includes a side restraining protrusion 1107 extending from the stop 1106 to retain the tab therein against side forces that may be placed on the strap 1110.

The tab 1112 and strap 1110 hook into and unhook from the pocket 1102 around the circumference of the pulley 1101, in contrast to being slid out through a side of the pulley. This allows easier replacement of the belts where sides of the pulley are constrained to a limited area.

With the tab 1112 in the pocket 1122 and the strap under tension, there is a first gap 1121 between an edge of the lip 1105 and the end of the strap 1110 and a second gap 1123 between a back stop of the pocket 1102 and the tab 1112 as illustrated best by FIG. 11D. The first and second gaps 1121, 1123 allow a maintenance person to hook and unhook the strap to the pulley. To unhook the strap from the pulley, the maintenance person first slackens the strap and slides it and the tab backward away from the stop 1106, and tilts the back side of the tab downward in the pocket, as illustrated in FIG. 11C by lifting the strap upward at a point away from the end, such as strap portion 1125 shown in FIG. 11C. To assemble the strap to the pulley, the back side of the tab is inserted into the recess and down into the pocket. The tab and strap are pushed forward toward the back stop of the pocket. Then a person pushes down on the strap at a point away from the end, such as strap portion 1125, to flex the end of the strap and front side of the tab down into the pocket so that the lip 1105 is engaged by the back side of the tab.

Strap Wrap Angle Around Pulleys

As illustrated in FIG. 11A, the straps are wrapped around the pulleys at a strap wrap angle 1150 from a point of tangency 1152 making first pulley contact to a point 1153 normal to the strap end at the tab as shown. Because the straps are wrapped around the pulleys at the wrap angle 1150, the amount of load seen by the ends of the straps is less than the load seen at the straight portion of the straps between pulleys (e.g., midspan). The reduced load seen at the ends of the straps is due to the friction between the straps and pulleys over the wrap angle 1150. Thus, the wrap angle 1150 may be increased to reduce the load seen at joint between the tab and strap, which is typically the weakest segment of the strap.

As discussed previously, the straps 1110 in the robotic surgical arm are metal straps having one or more layers or plies in a preferred embodiment of the invention and may be coupled to the tab 1102 by welding as illustrated by the welds 1114. The welds 1114 form a heat-affected zone that locally reduce the strap's material strength. That is, the "heat affected zone" surrounding the welds is weaker than the as-rolled condition of the portion of the straps sufficiently away from the welds.

A reliable and safe design for the straps calls for a breaking load at the straight portion of the strap between pulleys (e.g., midspan) to be less than or equal to the breaking load at the end tabs. Because the strength of the welds 1114 have more variation at the ends of the strap than at the midspan of the strap, a sensible design to consider for the wrap angle of the straps is one where the straps nearly always break not at the welds 1114 but well away from the welds (at midspan, for example). In the embodiments of the invention, the wrap angle was increased to sufficiently meet this criteria in a majority of the cases.

Testing on sample lots of straps wrapped around pulleys at each end with a worst case wrap angle indicates that a vast majority of ultimate failures occur not at but away from the welds 1114 so as to have a safe and reliable design. Theoretical calculations have also been made and show that a minimum wrap angle (worst case) of one hundred six degrees (1.85 radians) is sufficient for five or six ply metal belts with welded tabs/blocks to withstand 2025 pounds of force in the straight portion between pulleys.

Strap Tensioners

In one embodiment of the invention, an idler pulley is pivotally coupled to a swing arm tensioner to automatically set and maintain the correct tension in the straps. In another embodiment of the invention, a strap tensioner is part of a pin, tab, or block coupling the strap to a pulley and includes a manually adjustable screw.

Figure 12A:
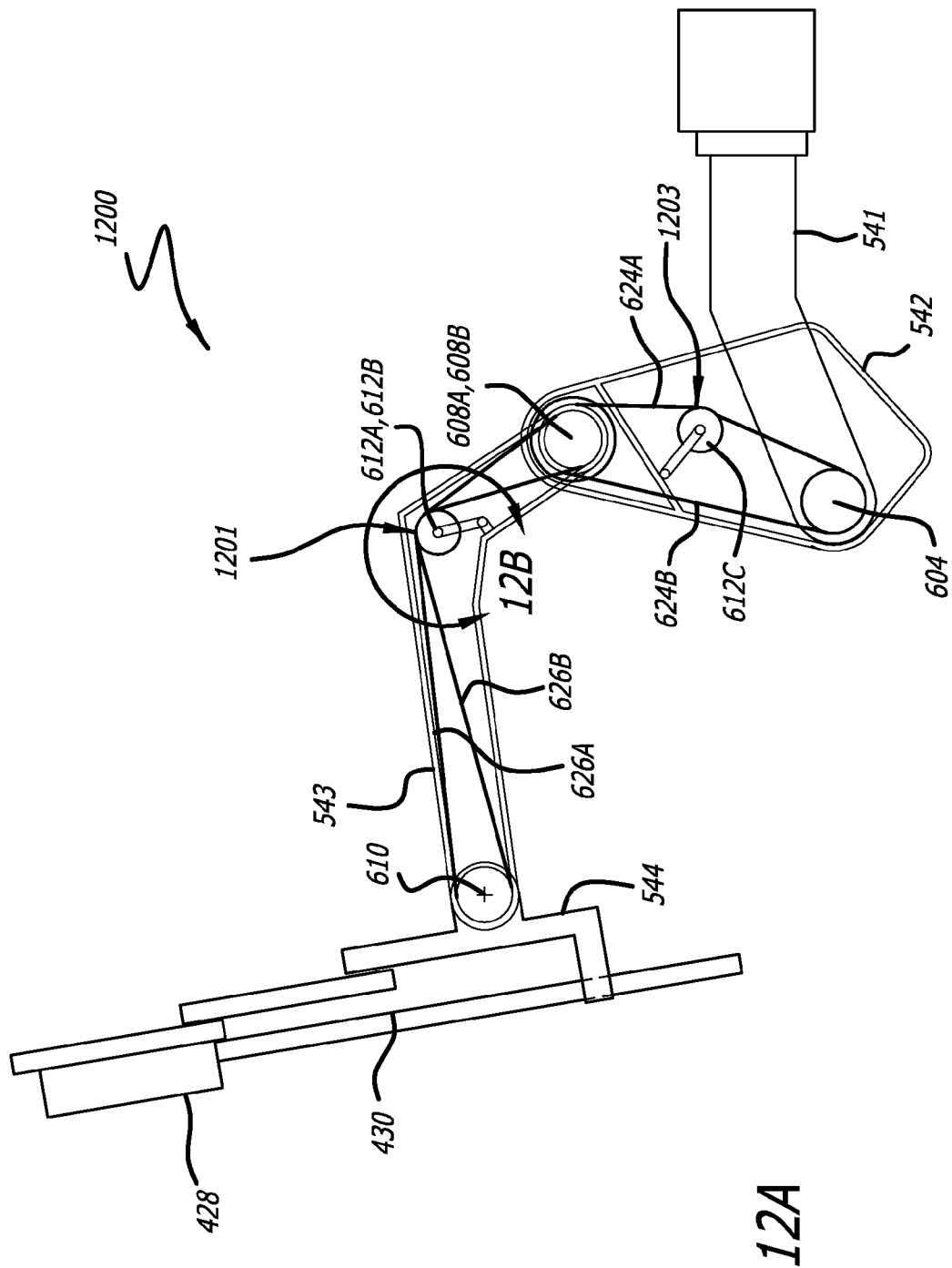
FIG. 12A illustrates a schematic view of a drive train of a robotic surgical arm with a second tensioning system that may be used to tension the straps in the second and third links.

Referring now to FIG. 12A, a schematic side view 1200 of the robotic surgical arm 600 is illustrated including swing arm tensioners 1201, 1203. The swing arm tensioner 1201 may be used to tension the straps 626A-626b in the third link 543. In the third link 543, the idler pulleys 612A-612B are pivotally coupled to the swing arm tensioner 1201. The idler pulleys 612A-612B can pivot about the pulley axis independent of each other. The swing tensioner 1203 may be used to tension both straps 624A-624B in the second link 542. In the second link 542, an idler pulley 612C is pivotally coupled to the swing arm tensioner 1203. The swing arm tensioners can automatically adjust the tension in the straps. Thus, the swing arm tensioners may also be referred to as auto-tensioners, self-adjusting tensioners, or idler-pulley swing arm tensioners.

Figure 12B:
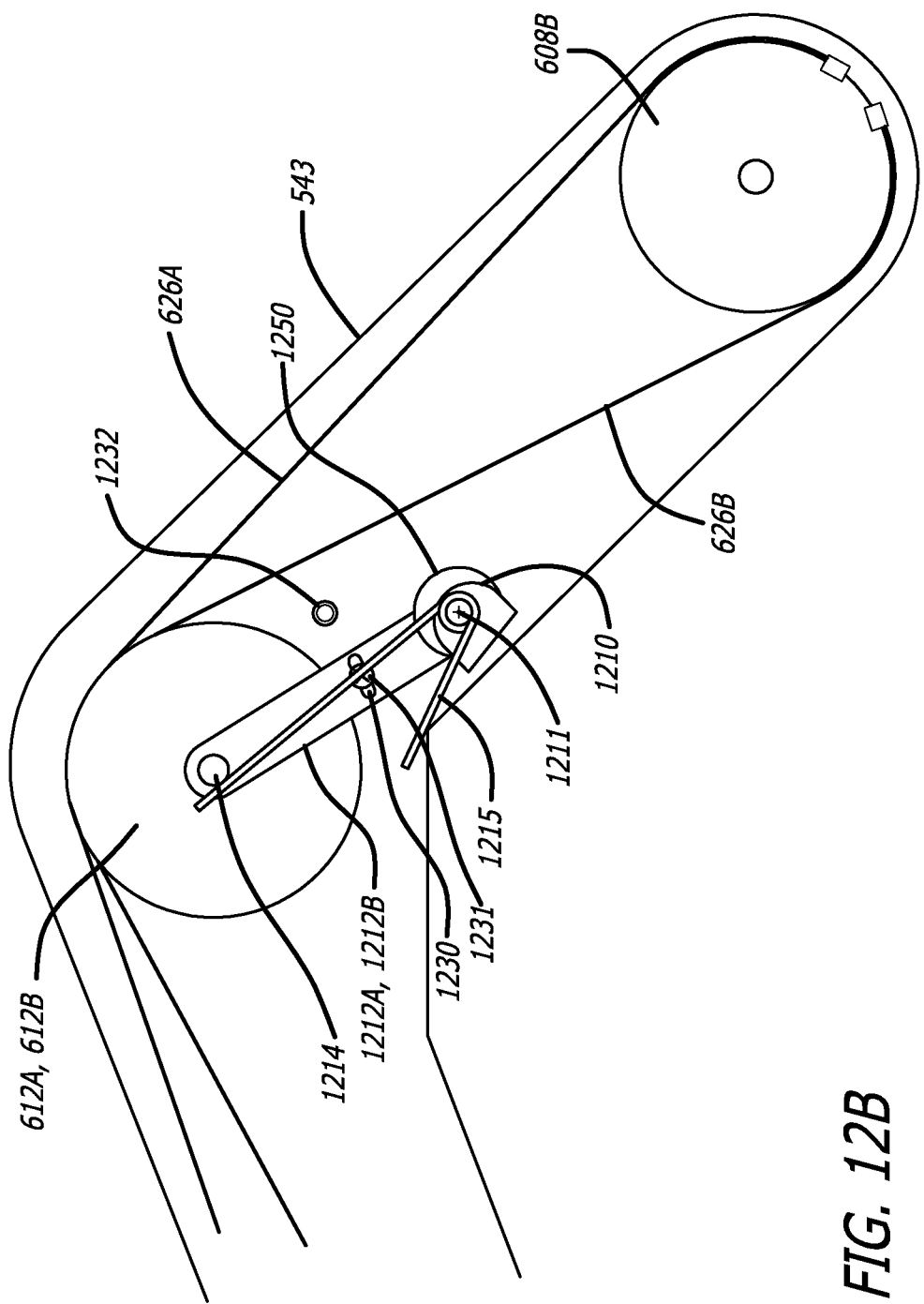
FIGS. 12B-12C illustrate magnified views of the second tensioning system that may be used in the links of the robotic surgical arm.
Figure 12C:
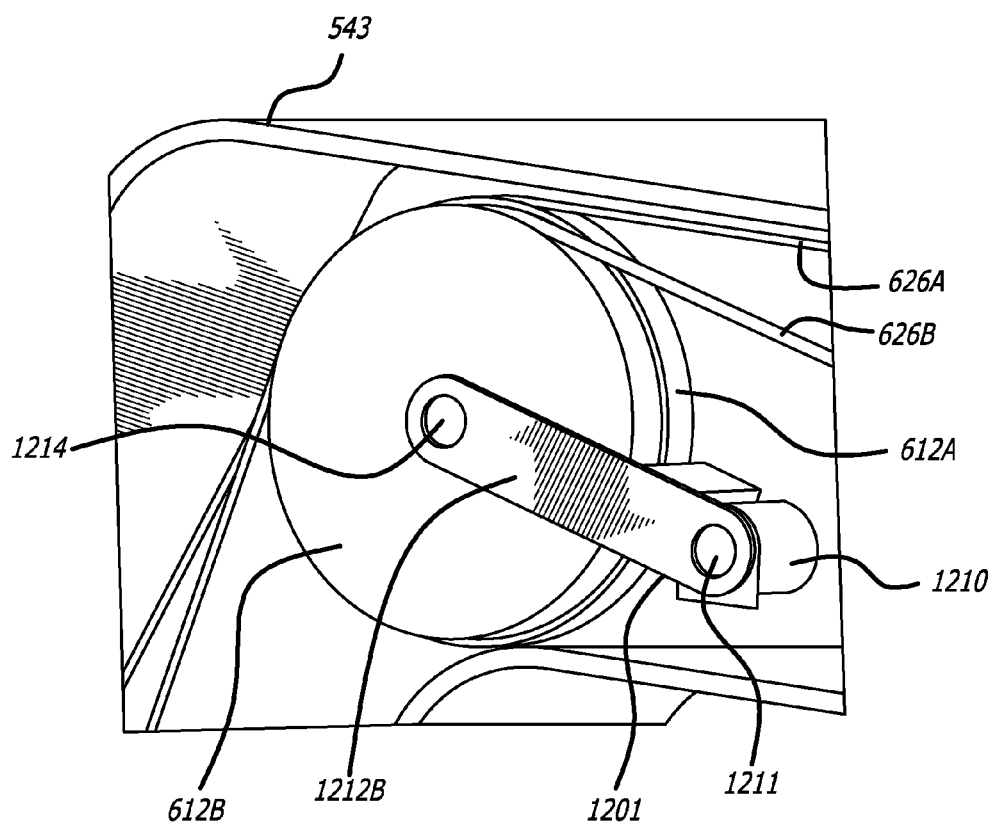

Referring now to FIGS. 12B-12C, magnified side and perspective views of the tensioner 1201 in the third link are illustrated. The swing arm tensioner 1201 may include a mounting base 1210, a pivotable shaft 1211 pivotably coupled to the mounting base, an arm 1212 having a proximal end pivotally coupled to the shaft, a torsional spring 1215 coupled at one end to the base 1210 and an opposite end to the arm 1212, a pulley shaft 1214 coupled near a distal end of the arms, and one or more idler pulleys 612A-612B, 612' pivotally coupled to the pulley shaft. In the case of the two strap system in the third link, the two idler pulleys 612A-612B are used so the straps 626A-626B may move in opposite directions. In the case of the three-strap system in the third link, a single idler pulley sufficiently wide enough to accommodate three straps in parallel may be used as the straps 626A,627, 628 are wrapped or unwrapped by the pulley rotating in the same direction.

The base 1210 of the tensioner couples to the housing or frame of the link for support in order to apply a force against the one or more straps.

The swing-arm tensioner automatically sets and maintains correct tension in bands when assembly is completed. The tension T in the straps is set by torsional spring 1215 and provides for automatic adjustment of the tension in the straps. The torsional spring 1215 is selected with a spring constant to set the desired tension in the straps at a given idler pulley or pulleys. With the tension being automatically set by the torsional spring, there is no need for tension calibration by a service person and thus no risk of an incorrect tension adjustment. Alternatively, a tension spring, compression spring, leaf spring, or other means of applying a force could be used in place of the torsional spring 1215.

However in one embodiment of the invention, the arm of the tensioner may be locked in place by a fastener, such as a screw 1231, so that the torsional spring does not adjust tension during normal operation. The screw 1231 would pass through a slot 1230 in arm 1212, and screw into a threaded hole in third link 543, thus locking the arm. Instead, the tension on the straps may be periodically recalibrated in the field. The fastener can lock the position of the arm 1212 relative to the base 1210 after the strap system is assembled together. To recalibrate the tension on the straps in the field, the fastener is simply removed or loosened to free the arms to swing and allow the spring to adjust the tension and then replaced or retightened. In the case of a screw, it may be unscrewed to release and then screwed in to retighten after automatic adjustment of the tension by the torsional spring. The advantage of locking the tensioner in place is that the compliance of the tensioner spring 1215 then does not affect the stiffness of the strap drivetrain. A stiffer drivetrain results in improved performance, due to less vibration of the robot.

In an alternative embodiment of the invention, an electrically engagable brake 1250 that locks the pivotal axis through the pivotable shaft 1211 so that the torsional spring does not adjust tension during normal operation. The brake 1250 may be periodically unlocked by computer 151, to allow the tension in the strap to be automatically reset. The brake 1250 is locked during surgery. The electrically engagable brake 1250 may reduce maintenance costs in that a maintenance person would not be required to periodically release a fastener to adjust tension as it is automatically performed by the computer 151. In other embodiments of the invention, the brake 1250 is not an electrically engagable brake but a brake that is pneumatically, hydraulically, or engaged by other means.

In the example geometry above, the reaction force "R" that acts between the pulley and the straps is congruent to two and one half times the tension "T" on the straps. Changes in geometry will alter the amount of reaction force and/or tension. However because both straps 626A,626B are automatically tensioned on the parallel idler pulleys 612A,612B, "slack" that develops in the straps and system will be taken up approximately by both straps being self-adjusted for tension by the tensioner 1201. Thus, the tensioner 1201 minimizes the rotation of the pulleys at the ends of the link as slack develops. Minimizing the rotation of pulleys in response to slackening minimizes error in the position of the remote center of motion (RCM) 666 in comparison with one idler pulley tensioner being used to tension a single strap in the link.

The swing arm tensioners may further include one or more swing arm sensors to quickly detect if a strap slackens indicating fatigue or if the strap fails or breaks. In this manner, the swing arm sensors provide a safety mechanism to protect a patient from harm. Sensor 1232 is a through-beam sensor, and it's beam would be broken if arm 1212 moved to block it's line-of-sight. Alternatively, other types of sensors to detect position of arm 1212 could be used.

Referring now to FIGS. 13A-13D and 14, embodiments of a strap tensioner including a tensioning block coupling the strap to a pulley are now described. Previously with reference to FIGS. 11A-11D, a strap hooking system 1100 was described with elements for strapping an end of a strap to a pulley 1101. The strap hooking system 1100 has elements somewhat similar to the embodiments of the strap tensioning systems 1300 and 1400 now described.

In the preferred embodiment of the invention, FIGS. 13A-13D illustrate the strap tensioning system 1300 that generally includes a pulley 1301 having a pocket 1302 and a strap 1310 with a tensioning block 1312 coupled at an end of the strap. But for a continuous belt, links of the robotic surgical arm having at least one strap may include at least one tensioning block 1312 to couple to a pulley 1301.

The pocket 1302 in the pulley 1301 is shaped to receive the tensioning block 1312. The tensioning block 1312 hooks into the pocket 1302. The pocket 1302 includes a lip 1305 at a back thereof to retain the tensioning block 1312 therein against longitudinal forces (i.e., the tension) placed on the strap. Additionally when no tension is being applied, a spring force in the metal strap 1310 keeps the block 1312 locked in place within the pocket so that it cannot be readily unhooked. In the event that a strap is slackened, removal of the block 1312 from the pocket is avoided so that the robotic surgical arm does not completely collapse and wildly move a surgical tool and injure a patient. The pocket further includes a stop 1306 at the front of the pocket 1302. The pocket 1302 further includes a side restraining protrusion 1307 extending from the stop 1306 to retain the front portion of the block therein against side forces that may be placed on the strap 1310.

To tension the strap 1310, the strap tensioning system 1300 further includes a fastener 1331. The fastener 1331 has significant forces applied to it from tensioning and coupling the strap to the pulley. The fastener 1331, such as a screw or bolt, has male threads 1332 at one end and a head 1333 at an opposite end with a tool receiver. The tool receiver in the head receives a tool to rotate the fastener. The tool receiver may be a slot, a hex socket, a cross, other type of indentation in the head, or the shape of the head itself, such as a hex head.

The tensioning block 1312 has a cylindrical opening 1335 with female threads 1336 to receive the fastener 1331 and mate with its male threads 1332. In one embodiment of the invention, the female threads 1336 may include a screw-lock helical coil to keep the fastener from rotating and changing the tension. The tensioning block has a limited distance to travel when being tensioned before its back side hits the front stop 1322. This distance between the block 1312 and the front stop 1322 is referred to as the tension travel distance DTT 1321.

The tensioning block 1312 generally includes a rectangularly shaped geometric solid (e.g., rectangular prism) portion at a front end and a cube shaped portion with the threaded opening 1335 at a back end, in one embodiment of the invention. The rectangularly shaped solid portion of the block 1312 further includes a bottom surface and an opposing top surface to couple to a bottom surface of the strap 1310. The width of the block may be substantially similar to the width of the strap.

In a preferred embodiment of the invention, the strap 1310 is a metal strap having one or more layers or plies as discussed previously with reference to FIGS. 9B and 10B. The tensioning block 1302 is also preferably formed of metal so that the strap 1310 may be welded thereto by welding as illustrated by the welds 1314. In other embodiments of the invention, the strap and tensioning block may be coupled together by other means.

To receive the end of the strap 1310, the pulley 1301 includes a recess 1303 in its circumference that is at least as wide as the strap 1310. The recess 1303 becomes progressively deeper until it joins with the pocket 1302. The recess ends at the lip 1305 of the pulley 1301.

In addition to the recess 1303 and pocket 1302, the pulley 1301 has a cutout 1342 to receive the fastener 1331 and allow its head 1333 to rotate therein. In one embodiment of the invention, a clearance between the head 1333 and sides of the cutout 1342 are sufficient to attach a tool, such as a socket, to the head 1333 of the fastener 1331 so that it may be turned. The pulley 1301 further has a cylindrical opening 1340, that is slightly larger in diameter than the fastener 1331, that extends from the cutout 1342 into pocket 1302 to allow the fastener 1331 to pass into the pocket and mate with the threaded opening 1335 in the block 1312.

Without the fastener 1331, the tensioning block 1312 and strap 1310 hook into and unhook from the pocket 1302 through the recess 1303 in the circumference of the pulley 1301, as illustrated by FIG. 13C. This is in contrast to being slid out through a side of the pulley. The recess in the circumference of the pulley allows easier replacement of the belts where sides of the pulley are constrained to a limited area. With the tensioning block 1312 hooked into the pocket 1302 as is illustrated by FIG. 13D, the fastener 1331 may be inserted into the cutout 1342 and opening 1340 to mate with the threaded opening 1335 of the tensioning block 1312. To release the strap from the pulley, the fastener 1331 is first unscrewed from the block 1312. The tensioning block can then be unhooked from the pocket 1302.

Figure 13A:
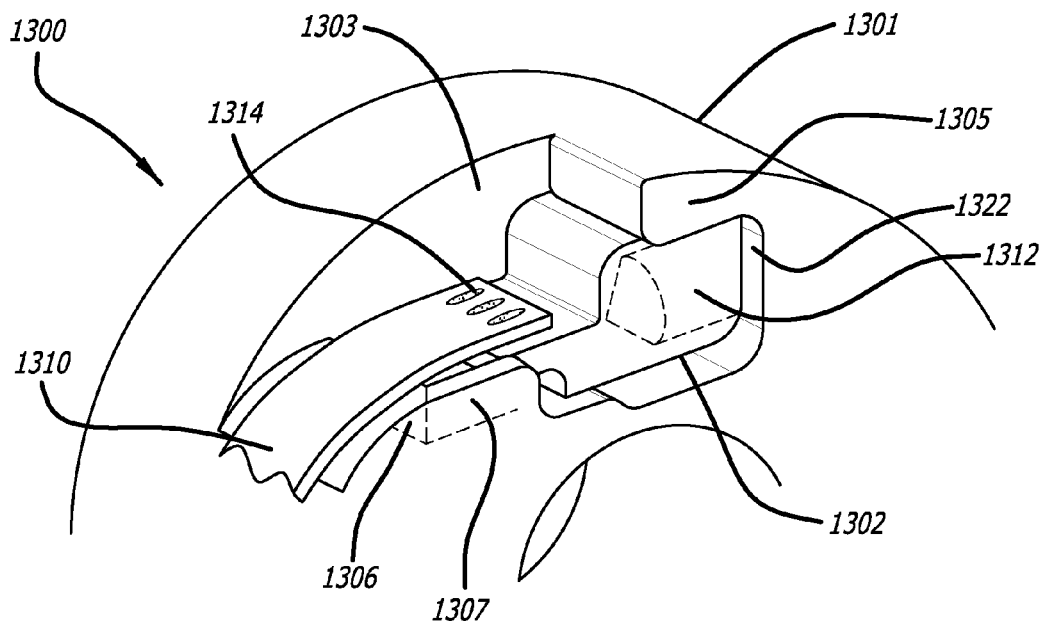
Figure 13B:
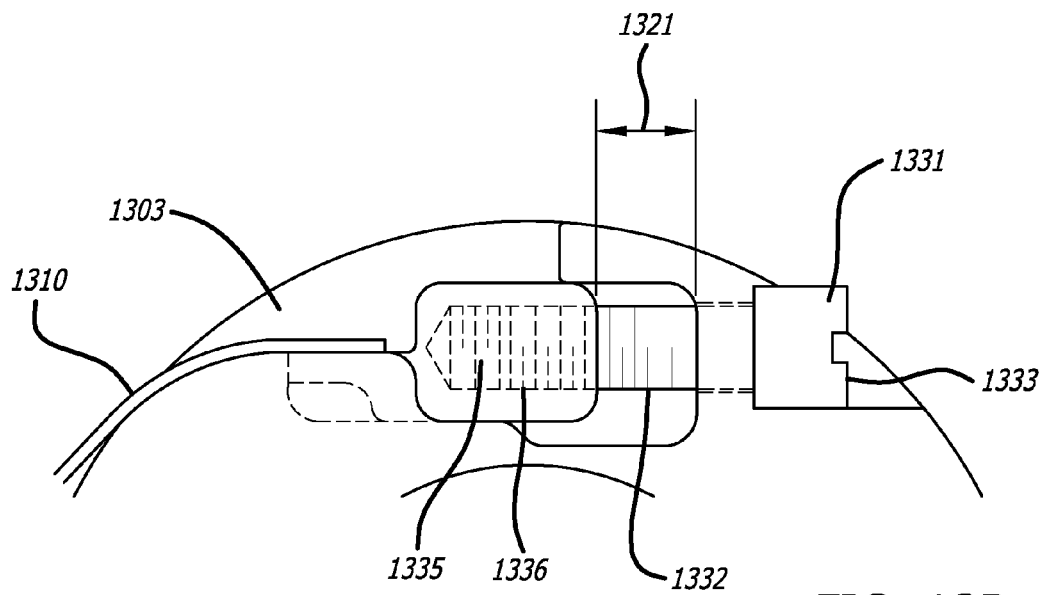

With the block 1312 in the pocket 1302 and the strap under tension, there is a gap between a back stop 1306 of the pocket 1302 and the block 1312, as illustrated in FIG. 13B. This gap and the tension travel distance 1321 allow a maintenance person to hook and unhook the strap to the pulley 1301. The tensioning block 1312 and strap 1310 hooks into and unhooks from the pocket 1302 similar to how the tab 1112 and strap 1110 hook and unhooks from the pocket 1102 described previously.

To change the tension on the strap 1310, the fastener may be manually turned by a hand tool, such as by a screw driver, socket wrench, or nut driver; or an automated tool, such as a speed driving drill with a torque clutch. To increase the tension on the strap 1310, the fastener 1331 is tightened by turning clockwise for standard threads and counter clockwise for reverse threads. This pulls on the tensioning block 1312 in the pocket to increase the tension on the strap. To decrease the tension on the strap 1310, the fastener 1331 loosened by turning counter clockwise for standard threads and clockwise for reverse threads. This pushes on the tensioning block 1312 in the pocket to release the tension in the strap. The tension is set using a sonic tension meter, which measures the transverse frequency of vibration of the straps, when strummed. The screw 1331 is adjusted until the frequency that corresponds to the desired tension is achieved. This is substantially similar to using a sonic frequency guitar tuner to set the desired tension of guitar strings.

Figure 14:
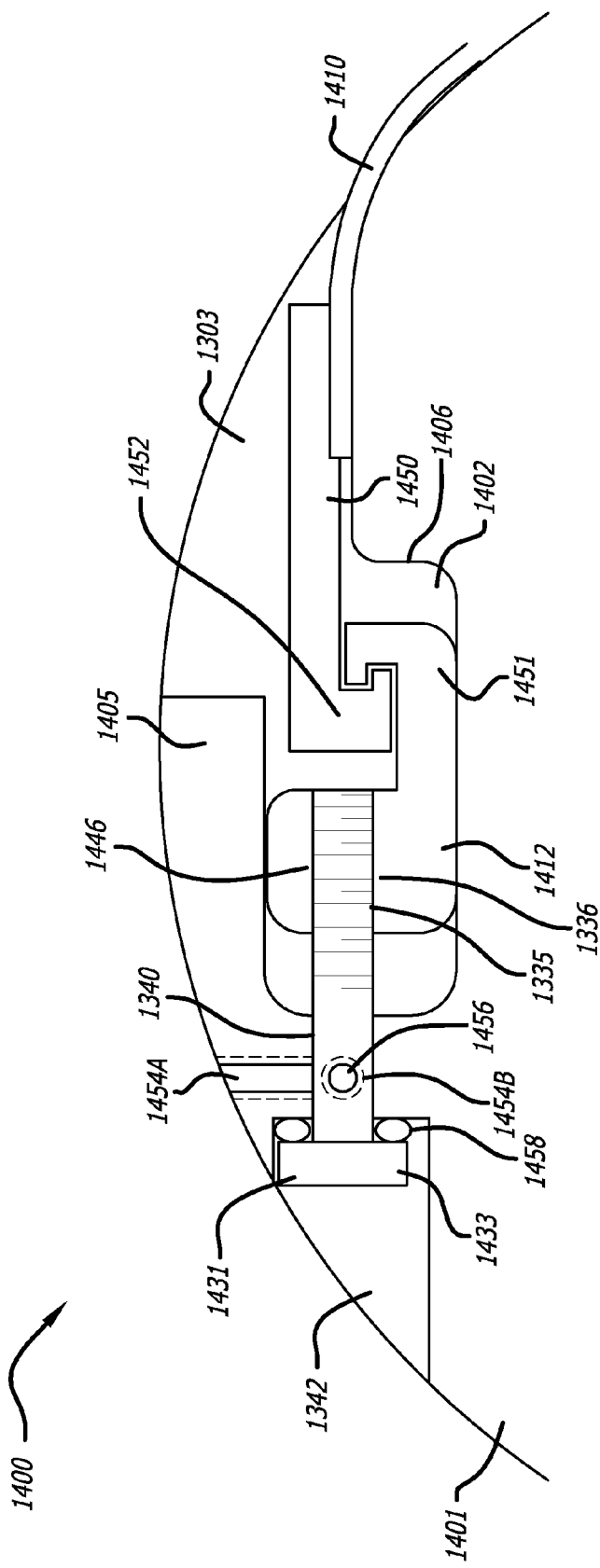
FIG. 14 illustrate a magnified view of a third tensioning system that may be used to couple and tension the straps to the pulleys in the links of the robotic surgical arm.

Referring now to FIG. 14, a strap tensioning system 1400 is illustrated that generally includes a pulley 1401 having a pocket 1402 to receive a tensioning block 1412 with a first hook 1451, and a strap 1410 with a hooked tab 1450 with a second hook 1452 coupled at an end of the strap. The strap tensioning system 1400 is somewhat similar to the strap tensioning system 1300 in operation but has a few more elements. Those elements that are identical use the same reference number and their description is incorporated here by reference. Moreover, one or more of the different elements of strap tensioning system 1400 may be incorporated into the strap tensioning system 1300, such as a screw lock helical coil or a set screw.

In FIG. 14, the pocket 1402 in the pulley 1401 is shaped to receive the tensioning block 1412 and the hook 1452 coupled to the strap 1410. The pocket 1402 includes a lip 1405 extending from a back side to retain the block 1412 therein against longitudinal forces (i.e., the tension) placed on the strap. The pulley 1401 further has an opening 1340 and a cutout 1342 to receive the tensioning fastener 1431 as is illustrated in FIG. 14.

As the tension on the strap 1410 may be insufficient to keep the tensioning fastener 1431 from backing out on its own and reducing the tension, the system 1400 may include a locking fastener coupled to the tensioning fastener 1431. In this case to receive the locking fastener, the pulley 1401 includes an opening 1454A starting at its circumference or an opening 1454B starting from a side down to the opening 1340. In either case, the opening 1454A,1454B is threaded to receive a locking fastener 1456, such as a puck or set screw. A distal end of the fastener 1456 couples against the tensioning fastener 1431 to lock it and keep it from rotating and altering the tension in the strap 1410. The locking fastener 1456 may be formed of brass, such as a brass tip set screw or a brass puck.

The hook 1451 of the tensioning block 1412 mates with the hook 1452 of the end tab 1450. The end tab 1450 is preferably welded to the strap 1410. With the strap under tension, the end tab 1450 is captured within the pocket 1402. Additionally, as was previously discussed in greater detail, without any tension a spring force in the metal strap 1410 may keep the hooks 1451-1452 mated together within the pocket so that they cannot be readily unhooked from each other. In the event that the tensioning fastener fails due to overloading of the arm and the strap is completely slackened, the hooks 1451-1452 may remain mated together so that the robotic surgical arm does not completely collapse and wildly move a surgical tool and injure a patient. The pocket further includes a stop 1406 at the front of the pocket 1402.

As previously mentioned, the strap tensioning system 1400 includes the tensioning fastener 1431 to tension the strap 1410. The tensioning fastener 1431, such as a screw or bolt, has male threads 1432 at one end and a head 1433 at an opposite end with a tool receiver. The tool receiver in the head receives a tool to rotate the fastener. The tool receiver may be a slot, a hex socket, a cross, other type of indentation in the head, or the shape of the head itself, such as a hex head. The tensioning fastener 1431 has significant forces applied to it from tensioning and coupling the strap to the pulley. The first fastener, the tensioning fastener 1431, may be a silver plated fastener, such as a silver plated screw, to minimize galling that might otherwise be caused by dissimilar metals.

To keep the tensioning fastener 1431 from rotating and tension changing, use of the locking fastener 1456, such as a set screw, was described previously. In the preferred embodiment of the invention, the tensioning block 1412 and 1312 includes a screw-lock helical coil 1446 in the opening 1335 with its threads 1336 to receive the tensioning fastener 1431, 1331. The screw-lock helical coil 1446 includes a couple of straight segments to squeeze on the screw and hold it in position. This increases the torque required to rotate the fastener 1431,1331 and screw it in or out of the opening 1335 in the block 1412,1312. This increased torque prohibits the tensioning fastener 1431,1331 from rotating on its own and changing the tension in the strap.

A washer 1458 may be inserted on the tensioning fastener 1431. The washer may be a star washer or a lock washer to further hold the position of the tensioning fastener 1431 when set.

Failsafe Strap Tensioning

The tensioning systems 1300 and 1400 each have a failsafe mechanism in case of failure of the fastener 1331, 1441. That is, if the tensioning fastener 1331,1431 breaks, the strap will not become free from the pulley 1301. The tensioner blocks 1312,142 are captive in their respective pockets 1302,1402 in which they reside by a moment generated by the metal strap which was discussed previously with respect to the tab 1112. If the tensioning fastener 1331,1431 breaks free from the blocks, the block and strap will only move a small distance to the back stop 1306,1406 in the pocket, such as the fail distance 1352 illustrated in FIG. 13D. The blocks 1312,1412 will not unhook out of their respective pockets 1302,1402 on their own. This allows for the end of the strap 1310 to be directly welded to the tensioning block 1312 as indicated by the welds 1314 in the system 1300.

Remote Center Adjustment with Strap Tensioners

Figure 18B:
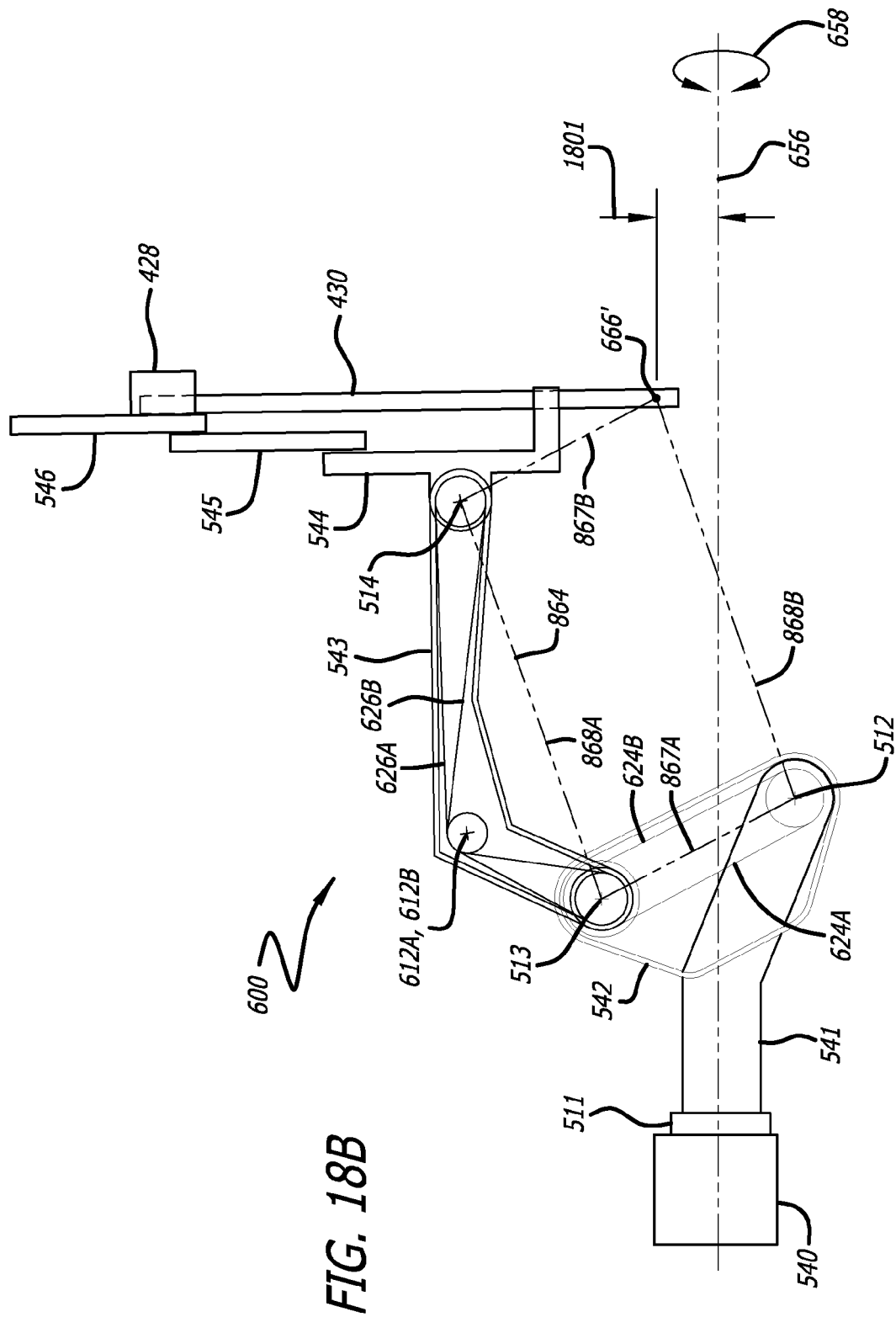
Figure 18C:
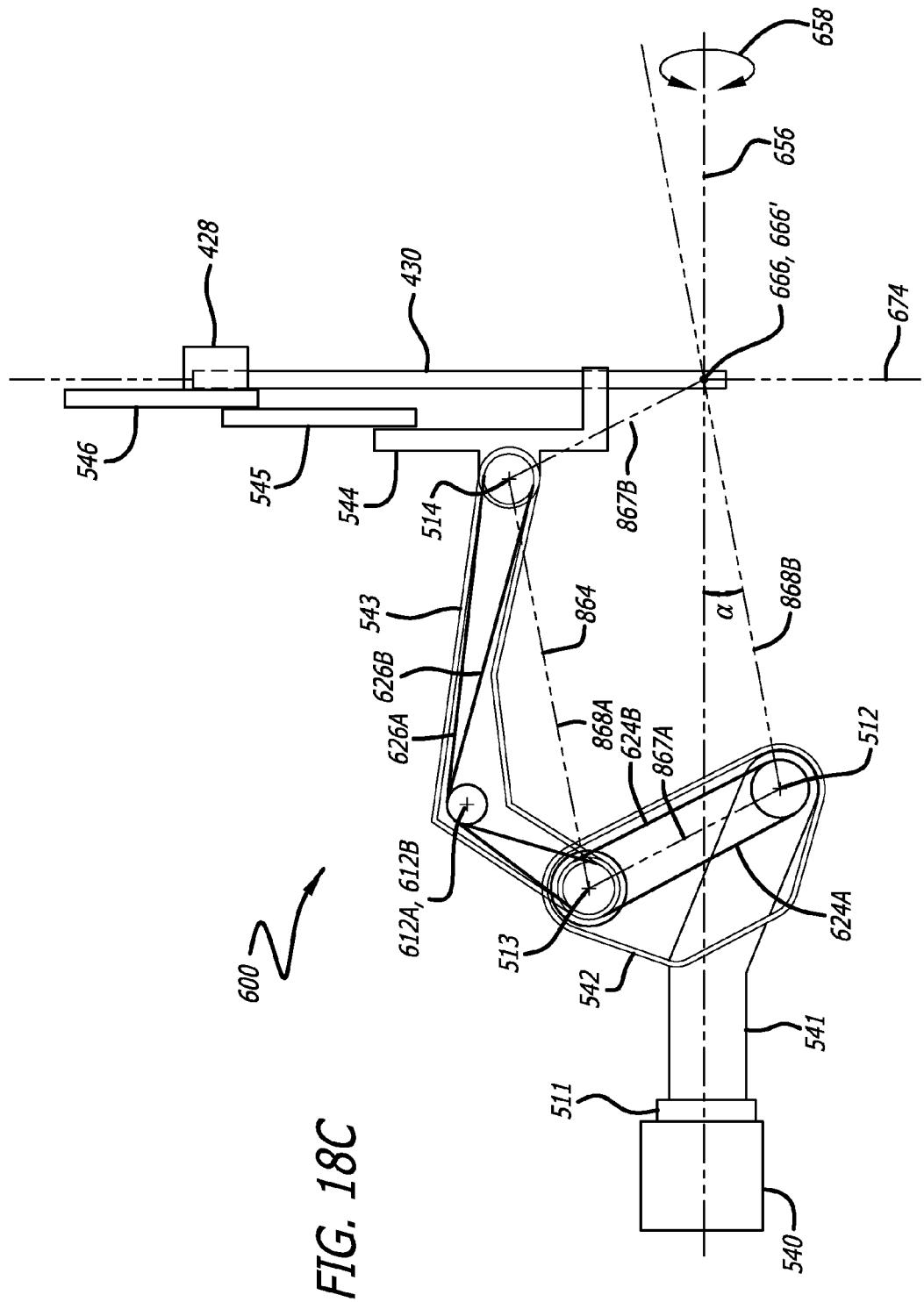

Referring momentarily to FIG. 18C, in order for the robotic surgical arm to have proper kinematics, the position of the remote center 666 is adjusted to achieve the parallelogram 864. Additionally, the pitch remote center 666' shown in FIG. 18B must lie on the yaw axis 656 for proper kinematics, and be coincident with the remote center 666. The dimension of the long side 868B of the parallelogram 864 may be controlled in part by the straps inside the third link (Link 3) 543. Referring momentarily to FIG. 18B, the remote center error 1801 is defined as the distance between the pitch remote center 666' and the yaw axis 656. This remote center error 1801 may be controlled in part by the straps inside the second link (Link 2) 542. Due to tolerances of manufactured components and deflection, the position of the remote center 666 must be calibrated during assembly and may be calibrated periodically during maintenance in the field. Referring to FIG. 11A, small adjustments to the pitch remote center position 666' can be accomplished by adjusting the tensioning blocks of the tensioning systems 1300,1400 for the straps of the second link 542 and the third link 543.

Figure 19:
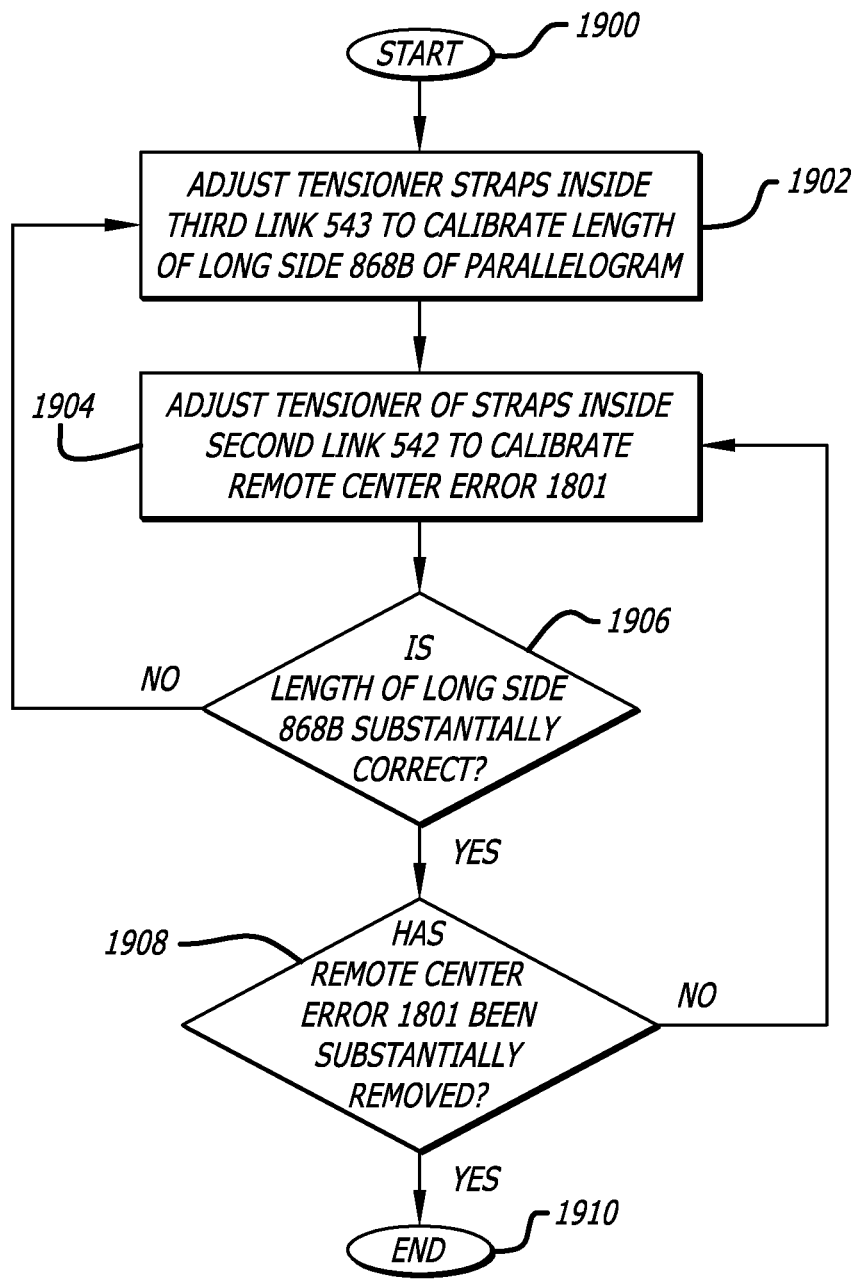
FIG. 19 is a flow chart describing how an offset robotic surgical arm is adjusted to the remote center using the tension adjusting system disclosed herein It will be appreciated that all the drawings of Figures provide for herein are for illustrative purposes only and do not necessarily reflect the actual shape, size, or dimensions of the elements being illustrated

FIGS. 18A-18C illustrate a method of one embodiment of the invention to calibrate the remote center 666 with strap tensioners. FIG. 19 is a flowchart that further illustrates this method. The calibration method starts at block 1900 and jumps to block 1902.

At block 1902, the tensioners of straps inside the third link 543 are adjusted to calibrate the length of the long side 868B of the parallelogram. To calibrate the length of the long side 868 of the parallelogram 864, the tensioning system of straps in the third link 543 can be adjusted. Tensioning blocks for strap 626A and strap 626B can adjusted in opposite directions to calibrate the length of the long side 868, in the case of a two strap system in the third link 543. In the case of a three strap system in the third link 543, Tensioning blocks for strap 626A and strap 627 or 628 may be adjusted in opposite directions to calibrate the length of the long side 868. This slightly rotates the fourth link (Link 4) 544 about the fourth joint 514 to achieve the desired length in the long side 868B of the parallelogram 864. That is, the tensioning blocks in the third link 543 can be adjusted to set the desired length of the long side 868B from the second joint 512 to the remote center 666.

If, for example, long side 868B is too long, as illustrated by erroneous long side 868B' in FIG. 18A, then the fourth link 544 needs to be rotated clockwise about the axis of rotation at joint 514, relative to the figure. The tensioning screw 1331 in the tensioner block 1312 at end of strap 626A is loosened, effectively lengthening strap 626A. The tensioning screw 1331 in the tensioner block 1312 at end of strap 626B is tightened, effectively shortening strap 626B. This calibration is completed with the long side 868B of the parallelogram 864 set to the correct length, as shown in FIG. 18B.

FIG. 18B further shows an example of remote center error 1801, where the pitch remote center 666' is above the yaw axis 656.

At block 1904, the tensioners of straps inside the second link 542 are adjusted to calibrate the remote center error. In this case, the third link 543 needs to be rotated clockwise about the axis of rotation at joint 513, relative to FIG. 18B. For this example, the tensioning screw 1331 in the tensioner block 1312 at end of strap 624A is loosened, effectively lengthening strap 624A. The tensioning screw 1331 in the tensioner block 1312 at end of strap 624B is tightened, effectively shortening strap 624B. This calibration is completed and the remote center error 1801 has been substantially eliminated, when the pitch remote center 666' lays on the yaw axis 656, as shown in FIG. 18C.

As discussed previously, the second link 542 and the fourth link 544 are kept from rotating relative to each other by straps 626A, 626B. Thus, when adjustment to remote center error 1801 is made, the parallelogram 864 is maintained and the length of long side 868B is not affected. Regardless, the length of the long side 868B of the parallelogram is verified after the remote center error has been removed.

At block, 1906, a determination is made if the length of the long side 868B of the parallelogram is correct. If not, the method returns to block 1902 and the length of the long side 868B of the parallelogram is calibrated again. If so, the method goes to block 1908.

At block 1908, a determination is made if the remote center error 1801 has been substantially removed. If not, the method returns to block 1904 and the remote center error is calibrated out once again. If the remote center error 1801 has been substantially removed, the method of calibration ends at block 1910.

Strap Guide Bearing System

In a situation where straps or belts span long distances and pass over idler pulleys, they must be controlled laterally so that they do not wander off of pulleys. Due to variation in manufacturing tolerances of the straps, pulleys and other components, they sometimes wander off of a pulley that is not sufficiently wide enough to handle the variation.

To provide a compact and narrow robotic surgical arm to avoid collisions with other equipment, it is desirable to use narrow idler pulleys. With narrow idler pulleys, proper tracking of straps over idler pulleys is key to avoid strap failure. To keep straps properly tracking on narrow pulleys, a strap guide bearing system may be used.

Figure 15:
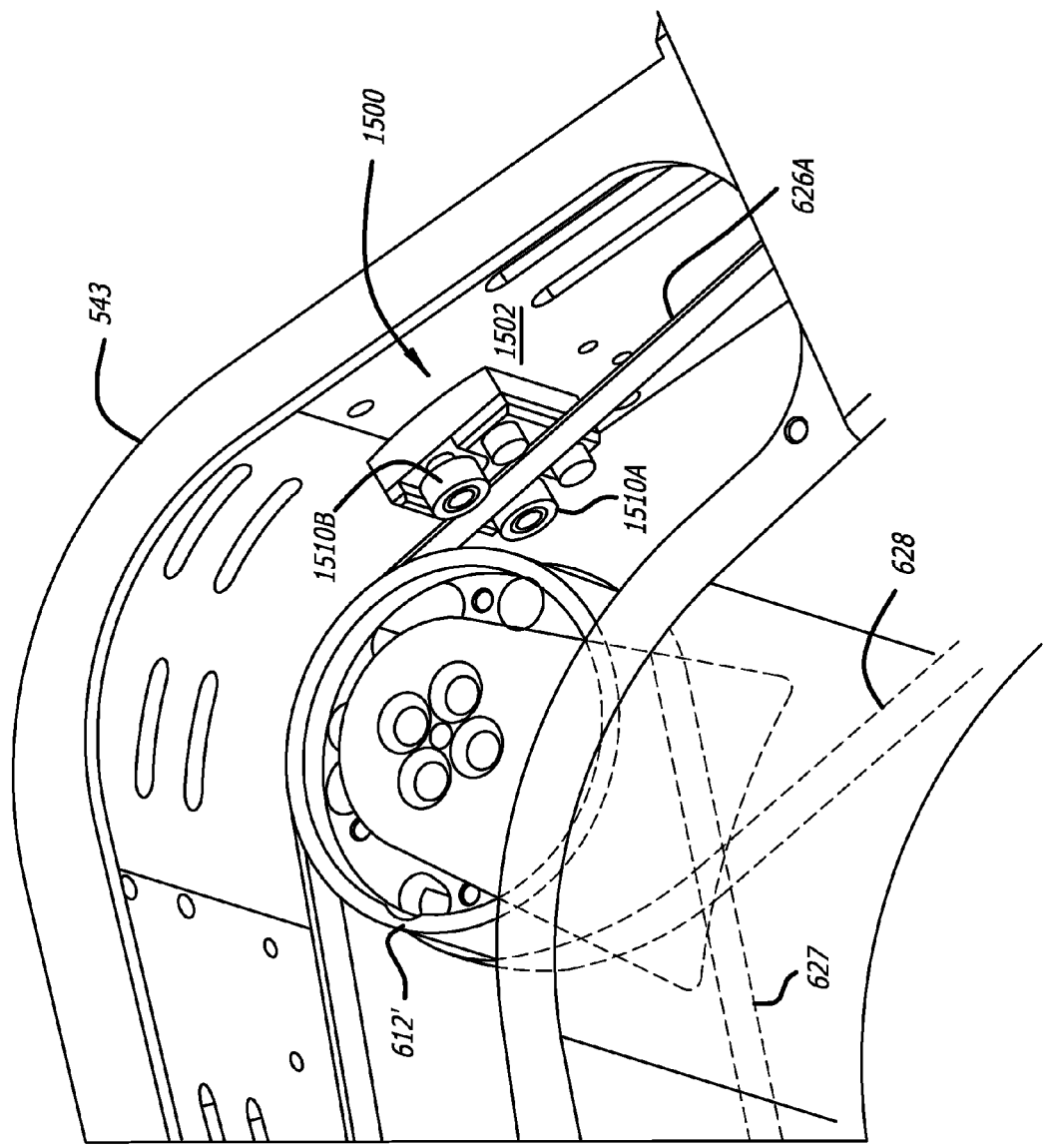
FIG. 15 illustrates a perspective view of a strap guide system in the third link of the robotic surgical arm to track the strap onto the idler pulley.

Referring now to FIG. 15, the third link 543 of the robotic surgical arm is illustrated with a three-belt system. Strap 626A extends a long distance between joint pulley 608B and joint pulley 610. In contrast, straps 627 and 628 are constrained laterally by their attachment to the idler pulley 612', and a strap guide system is unnecessary. To keep strap 626A properly tracking on the idler pulley 612', a strap guide system 1500 is provided in link 543. The strap guide system 1500 is mounted inside the housing of link 543 to an inside surface 1502 over a strap 626A such that a pair of spaced apart pulleys or roller bearings 1510A and 1510B straddle the strap 626A. In this manner, the sides of the strap 626A are laterally guided by the roller bearings 1510A-1510B to maintain proper tracking on pulley 612'.

Figure 16A:
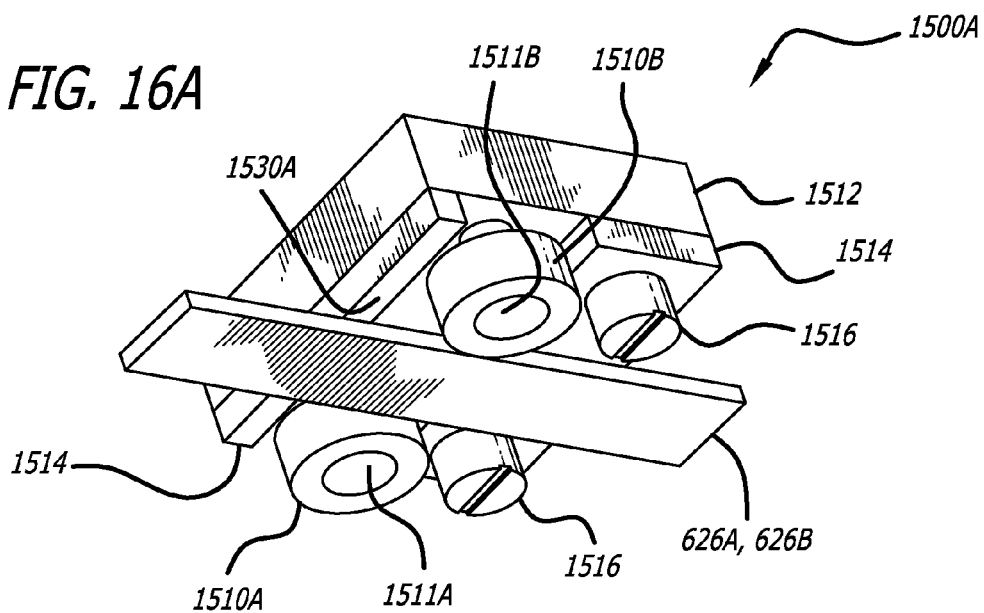
FIGS. 16A-16B illustrate alternate embodiment of the a strap guide bearing that may be used in FIG. 15.
Figure 16B:
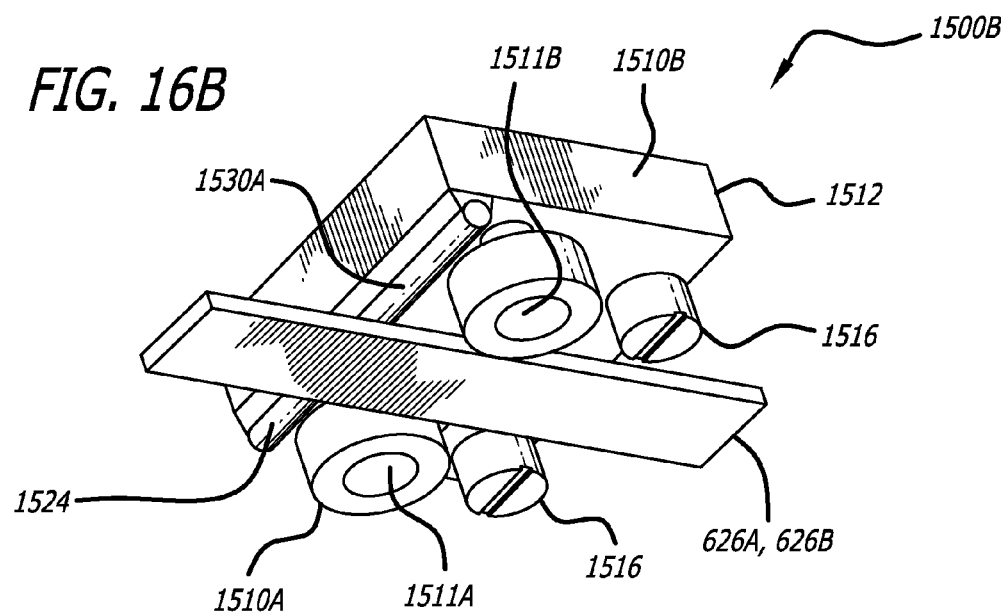

FIGS. 16A-16B illustrate alternate embodiments of the strap guide system 1500.

Referring now to FIG. 16A, a magnified prospective view of a strap guide system 1500A is illustrated. The strap guide system 1500A includes the roller bearings 1510A-1510B, mounting block 1512, an anti-friction pad 1514, dowel pins 1511A-1511B, and one or more fasteners 1516. The one or more fasteners 1516 are used to hold the strap guide system mounted against the surface 1502 of the third link 543.

The anti-friction pad 1514 is coupled up against the mounting block 1512 by the fasteners 1516. The anti-friction pad 1514 reduces abrasion of strap 626A and any flat flex cables and ground straps riding thereon by keeping them all from puffing up too much over the idle pulley 612' when they are under stress. The length of the anti-friction pad 1514 is substantially parallel to the length of the belt. The anti-friction or anti-abrasion pad 1514 may be a PTFE pad, a Teflon pad, or a material having a surface with a low coefficient of friction. The flat flex cables and ground straps riding on strap 626A through the third link is more fully described in U.S. provisional patent application Ser. No. 60/752,788 entitled "FLAT ELECTRICAL CONDUCTORS OVER PULLEYS IN A STRAP DRIVE-TRAIN OF A ROBOTIC SURGICAL ARM", filed on Dec. 21, 2005 by Todd Solomon.

Ordinarily the metal belts 626A, 626B do not ride up against the anti-friction pad 1514. Normally there is a gap 1530A between the anti-friction pad 1514 and the metal strap 626A, 626B. However if there is slack in a strap, the gap 1530A may become zero and the anti-friction pad 1514 may press back on the strap.

As mentioned previously, in the three strap system of link three 543, only one strap guide system 1500 is needed for strap 626A. In the two strap system of link three 543, two strap guide systems 1500 are utilized as both straps cover a long distance between pulleys. One strap guide system 1500 is provided for strap 626A and a second strap guide system 1500 is provided for strap 626B.

The mounting block 1512 is formed of aluminum in one embodiment of the invention. The rollers 1510A-1510B are ball bearings or roller bearings in one embodiment of the invention. The dowel pins 1511A-1511B are press fit and/or glued into the center race of the bearings to rotatably couple the rollers 1510A-1510B to the mounting block 1512. Alternately, the dowel pins could be an integral part of the rollers 1510A-1510B.

Referring now to FIG. 16B, an alternate strap guide system 1500B is illustrated. Strap guide system 1500B is similar to strap guide system 1500A of FIG. 16A. There are a number of duplicate elements having the same reference numbers and their description is incorporated here by reference. However, instead of an anti-friction pad 1514, a roller 1524 parallel to the width of the metal belt 626A, 626B is used to push down on them if they or any other strap puffs up near the idler pulley 612' that might be riding on top of the metal belt. Ordinarily, the metal belt 626A, 626B does not ride up against the roller 1524. Instead there is a gap 1530B between the metal belt 626A, 626B, and the roller 1524.

The belt guide bearing system 1500 is compact and reliably keeps the straps tracking on the narrow idler pulley or pulleys. The belt guide bearing system 1500 may also be used to control the tracking of flat flex cables and a beryllium copper ground strap along with the tensioned metal straps in a robotic surgical arm, as is more fully discussed in U.S. provisional patent application Ser. No. 60/752,788 entitled "FLAT ELECTRICAL CONDUCTORS OVER PULLEYS IN A STRAP DRIVE-TRAIN OF A ROBOTIC SURGICAL ARM", filed on Dec. 21, 2005 by Todd Solomon.

Camber Adjustment Pulley

Instead of or in addition to using a strap guide system to keep the straps tracking on the idler pulleys, a camber adjustment system may be used. The camber adjustment system provides means of adjusting the camber angle of the idler pulleys in order to keep the belts tracking.

Figures 17B, 17C:
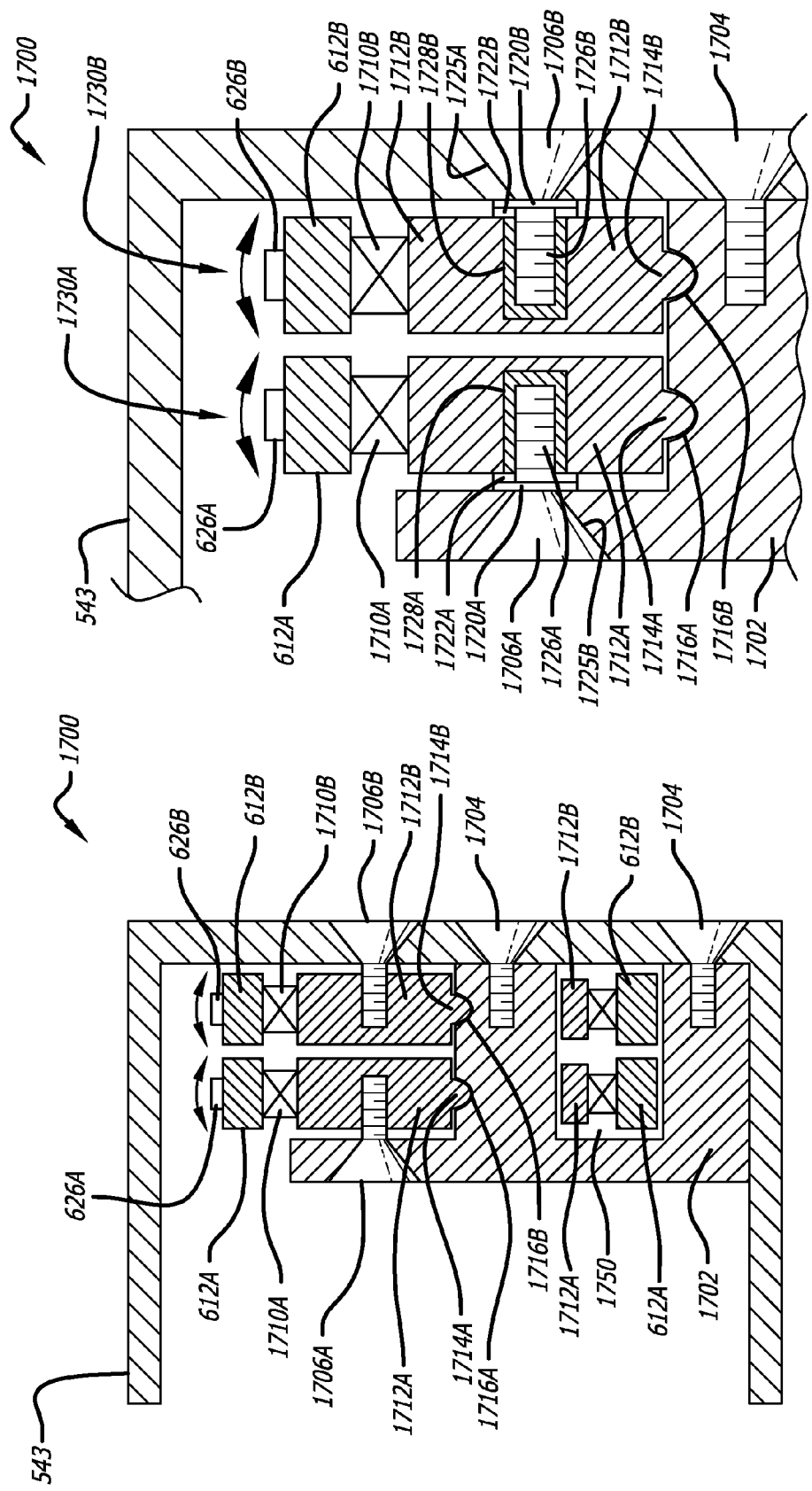
Figure 17D:
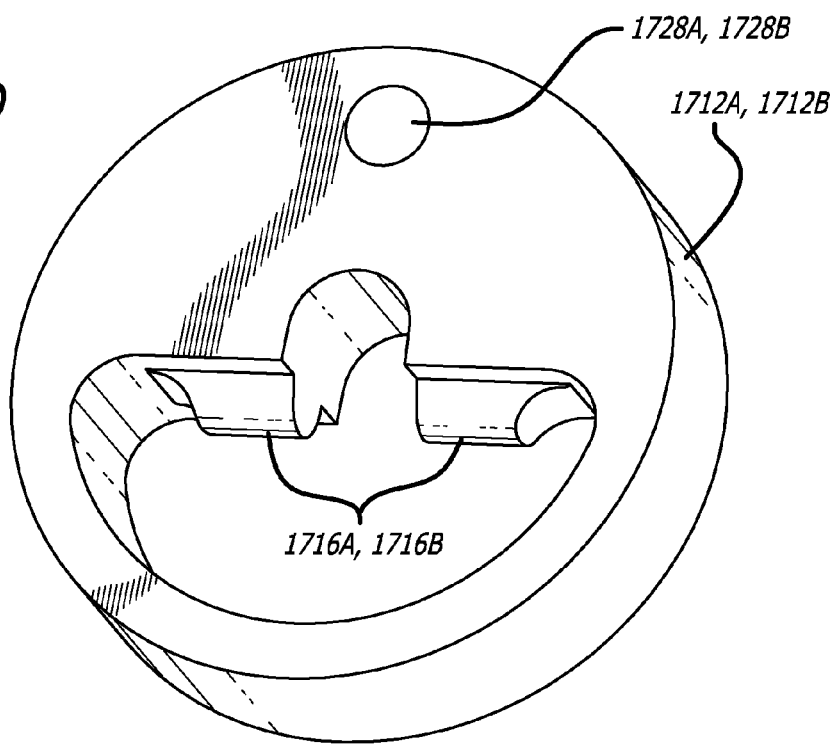
Figure 17E:
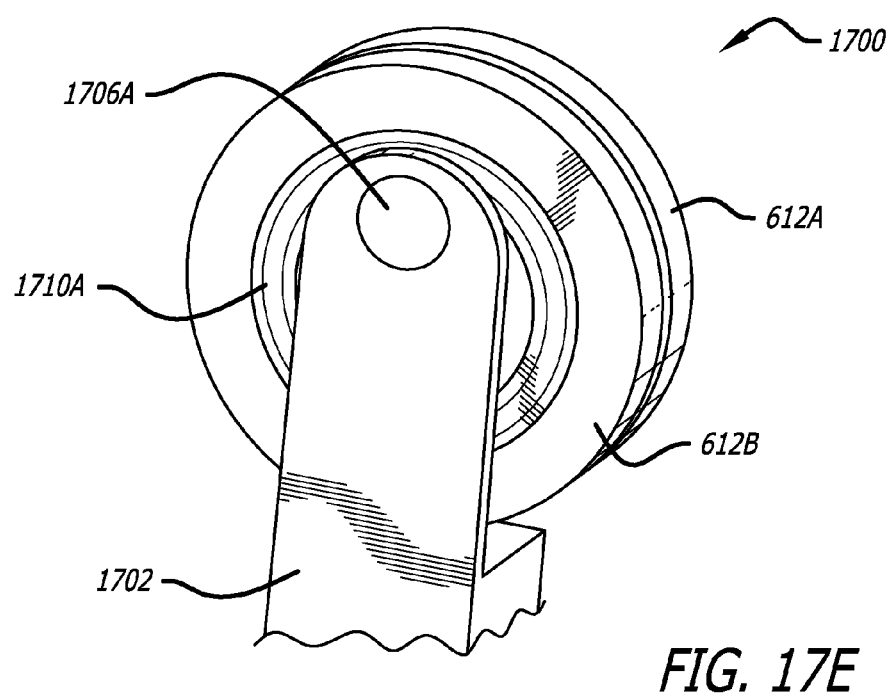

Referring now to FIGS. 17A-17E, a camber adjustable pulley system 1700 is illustrated and now described. One or a pair of pulleys 612A-612B may be provided in the camber adjustable pulley system 1700 to properly guide a one or a pair of straps 626A-626B, respectively. The camber adjustment pulley system 1700 is mounted to the third link 543 by a bracket 1702 and fasteners 1704 as illustrated in FIG. 17B.

To adjust the camber of each pulley 612A, 612B, pivoting or camber adjustment screws 1706A, 1706B are provided. Each of the idler pulleys 612A, 612B are respectively supported by bearings 1710A, 1710B and pivotable pulley mounts 1712A, 1712B. Each of the pivotable pulley mounts 1712A, 1712B include a pair of pivot points 1714A, 1714B, near a center of the pulley axis of each pulley 1612A, 1612B. Bracket 1702 has a pair of pivot valleys 1716A, 1716B to receive the pair of pivot points 1714A, 1714B, respectively. As illustrated, the pair of pivot valleys 1716A, 1716B are spaced apart to provide sufficient space in the bracket for the pair of straps, the pair of pulleys, the pair of pivotable pulley mounts, the pair of bearings, and the camber adjustment range, FIG. 17D better shows the pair of pivot points 1714A, 1714B in each of the pivotable pulley mounts 1712A, 1712B.

An open region 1750 illustrated in FIGS. 17A-17B allows the pulleys 625A-625B and bearings 1710A-1710B to rotate around the pivotable pulley mounts 1712A, 1712B and the bracket 1702.

Referring now to FIG. 17C, a magnified view of a portion of the cross-section better illustrates the camber adjustment screws 1706A, 1706B to adjust the pulley mounts 1712A, 1712B at the bracket 1702 and the third link 543. Arrows 1730A and 1730B illustrate the camber range of motion in each of the pulleys 612A, 612B in response to the camber adjustment screws 1706A, 1706B. Accordingly, the rotational axis of the pulleys 612A, 612B are tilted independently by the camber adjustment screws 1706A, 1706B.

The camber adjustment screw 1706B is allowed to turn in a non-threaded opening 1725A in the third link 543. Camber adjustment screw 1706A is allowed to turn a non-threaded opening 1725B in bracket 1702. As a result, each camber adjustment screw 1706A, 1706B has a snap ring 1720A, 1720B to retain the head of the screws within the respective openings 1725A, 1725B.

Additionally, each of the camber adjustment screws 1706A, 1706B are preloaded by a spring washer 1722A, 1722B coupled between the pivoting pulley mount 1712B and the third link 543, in between the bracket 1702 in the pivoting pulley mount 1712A. The spring washers 1722A, 1722B apply pressure to the pivoting pulley mounts 1712A and 1712B to force them away from bracket 1702 and the link 543 respectively. Additionally, the spring washers 1722A, 1722B apply a pressure between the screw threads 1726A, 1726B and the female thread of threaded openings 1728A, 1728B in the pulley mounts 1712A, 1712B so as to deter the screws 1706A, 1706B from turning freely. That is, the camber settings of the pulleys 626A,626B are maintained by deterring movement in the camber adjustment screws 1706A, 1706B.

Conclusion

The elements previously described of a strap drive train system in a robotic surgical arm provide a number of advantages. The strap drive train provides a reduction in friction of pitch movement of the robotic surgical arm so as to reduce the required motor power and improve back-drive-ability. The strap drive train provides a high degree of stiffness in the robotic surgical arm to reduce vibrations and deflections thereof. The strap drive train provides a high degree of strength in the robotic surgical arm high to increase safety to patients and assistants around the arm. The strap drive train allows easy adjustment of remote center of in the robotic surgical arm to reduce manufacturing and maintenance costs. The strap drive train provides a light and compact robot surgical arm that increases the range of motion and makes it easier to set up and use.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art after reading this disclosure. For example, the embodiments of the invention have been described with reference to a robotic surgical arm. However, the embodiments of the invention are equally applicable to other types of robotic arms and not just robotic surgical arms. Instead, the embodiments of the invention should be construed according to the claims that follow below.

What is claimed is:

1. A robotic arm comprising:
   a linkage assembly including a plurality of links pivotally coupled in series together at one or more joints to slidingly support a tool along an insertion axis, the plurality of links including a first pulley and a second pulley;
   at least one strap coupled between the first pulley and the second pulley to drive the linkage assembly; and
   a strap tensioning system coupled to the at least one strap, the strap tensioning system to tension the at least one strap;

wherein the strap tensioning system includes
the first pulley having a first pocket;
the second pulley having a second pocket; and
the at least one strap including
a tab coupled to a first end of the at least one strap, the tab to hook into the first pocket of the first pulley to couple the first end of the at least one strap thereto, and
a tensioning block coupled to a second end of the at least one strap, the tensioning block to hook into the second pocket of the second pulley to couple the second end of the at least one strap thereto;
wherein the first pulley further has a first recess in a portion of its circumference joining the first pocket to receive the first end of the at least one strap, a first stop at a front of the first pocket to couple to a front side of the tab, a first side restraining protrusion extending from the first stop to retain the tab in the first pocket, and a first lip at the back of the first pocket to further retain the tab in the first pocket; and
wherein the second pulley further has a second recess in a portion of its circumference joining the second pocket to receive the second end of the at least one strap, a second stop at a front of the second pocket to couple to a front side of the tensioning block, a second side restraining protrusion extending from the second stop to retain the tensioning block in the second pocket, and a second lip at the back of the second pocket to further retain the tensioning block in the second pocket.

2. The robotic arm of claim 1, wherein the strap tensioning system further includes
a tensioning fastener to tension the at least one strap, and wherein
the tensioning block has an opening with threads, and
the second pulley further has a cutout and an opening into the second pocket to receive the tensioning fastener and allow the tensioning fastener to mate with the threaded opening in the tensioning block.

3. The robotic arm of claim 2, wherein the strap tensioning system further includes
a screw-lock helical coil in the threaded opening of the tensioning block to keep the tensioning fastener from rotating and changing tension on the at least one strap.

4. The robotic arm of claim 2, wherein the strap tensioning system further includes
a locking fastener to keep the tensioning fastener from backing out on its own and reducing the tension on the at least one strap, and
the second pulley further has a threaded opening to receive the locking fastener and couple it against the tensioning fastener.

5. The robotic arm of claim 1, wherein
the at least one strap is formed of multiple plies of metal generating a spring force to keep the tab locked into the first pocket of the first pulley and the tensioning block locked into the second pocket of the second pulley to avoid complete collapse of the arm if the at least one strap is slackened.

* * * * *